United States Patent
Takada et al.

(10) Patent No.: US 9,193,747 B2
(45) Date of Patent: Nov. 24, 2015

(54) ORGANIC ELECTROLUMINESCENT DEVICE

(75) Inventors: Saki Takada, Ashigarakami-gun (JP); Kazunari Yagi, Minami-Ashigara (JP); Takeshi Murakami, Minami-Ashigara (JP); Eiji Fukuzaki, Ashigarakami-gun (JP)

(73) Assignee: UDC Ireland Limited, Dublin (IE)

( * ) Notice: Subject to any disclaimer, the term of this patent is extended or adjusted under 35 U.S.C. 154(b) by 896 days.

(21) Appl. No.: 12/683,178

(22) Filed: Jan. 6, 2010

(65) Prior Publication Data

US 2010/0171111 A1     Jul. 8, 2010

(30) Foreign Application Priority Data

| Jan. 7, 2009 | (JP) | 2009-002056 |
| Aug. 11, 2009 | (JP) | 2009-186893 |
| Aug. 31, 2009 | (JP) | 2009-201156 |

(51) Int. Cl.

| H01L 51/54 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ............ C07F 15/0086 (2013.01); C09K 11/06 (2013.01); H01L 51/0087 (2013.01); C09K 2211/1029 (2013.01); C09K 2211/185 (2013.01); H01L 51/5016 (2013.01)

(58) Field of Classification Search
None
See application file for complete search history.

(56) References Cited

U.S. PATENT DOCUMENTS

| 7,947,383 B2 * | 5/2011 | Ise et al. ................... 428/690 |
| 2005/0158578 A1 * | 7/2005 | Iwakuma et al. ........... 428/690 |
| 2005/0249970 A1 * | 11/2005 | Suzuri et al. ............... 428/690 |
| 2009/0261721 A1 * | 10/2009 | Murakami et al. .......... 313/504 |

FOREIGN PATENT DOCUMENTS

| JP | 2006-093665 A | 4/2006 |
| JP | 2006-261623 A | 9/2006 |
| JP | 2007-019462 A | 1/2007 |
| WO | WO 2006/033440 A1 * | 3/2006 |

* cited by examiner

*Primary Examiner* — Marie R. Yamnitzky
(74) *Attorney, Agent, or Firm* — Riverside Law LLP

(57) ABSTRACT

An organic electroluminescent device is provided and includes: a pair of electrodes; and a light emitting layer between the electrodes. The organic electroluminescent device has a layer containing a compound represented by formula (I).

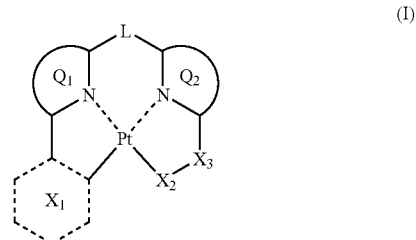

(I)

L represents a divalent linking group, $Q_1$ and $Q_2$ each independently represents an aromatic or aliphatic heterocycle coordinated to Pt through a nitrogen atom, $X_1$ represents a 6-membered ring containing one or more nitrogen atoms, $Q_1$, $Q_2$, and $X_1$ each independently may have a substituent, $X_2$ represents a sulfur atom, a phosphorus atom, an oxygen atom, or a nitrogen atom, and $X_3$ represents a carbon atom, a sulfur atom, or a phosphorus atom.

23 Claims, 1 Drawing Sheet

ORGANIC ELECTROLUMINESCENT DEVICE

This application is based on and claims priority under 35 U.S.C. §119 from Japanese Patent Application Nos. 2009-002056, 2009-186893, and 2009-201156, filed Jan. 7, 2009 and Aug. 11, 2009, and Aug. 31, 2009 respectively, the entire disclosures of which are herein incorporated by reference.

BACKGROUND OF THE INVENTION

1. Field of the Invention

The present invention relates to an organic electroluminescent device (which may hereinafter be called "organic EL device"), an organometallic complex compound used therefor, and a light emitting apparatus and an illumination apparatus using the device.

2. Background Art

Research and development are being vigorously made on organic electroluminescent devices because they can emit light with a high luminance even by low voltage driving. In general, organic EL devices each has one or more organic layers including a light emitting layer and a pair of electrodes sandwiching them therebetween. For light emission, they utilize energy of an exciton generated as a result of recombination, in the light emitting layer, of electrons injected from a cathode and holes injected from an anode.

Using phosphorescent materials contributes to efficiency improvement of the device. As the phosphorescent materials, iridium complexes and platinum complexes are known. There are reports on platinum complex light emitting materials capable of emitting blue to green light (refer to, for example, Japanese Patent Laid-Open Nos. 2007-19462, 2006-261623, and 2006-93665). The light emitting layer of an organic electroluminescent device using phosphorescence is formed by adding a phosphorescent material to a material (host material) involved in charge transport.

Phosphorescent materials however require a wider energy gap than fluorescent materials in principle. This means that due to an increase in IP and decrease in Ea, an injection barrier between an adjacent layer on the cathode side and LUMO level rises, which usually results in such a problem that drive voltage increases.

An increase in the drive voltage causes a reduction in power efficiency per amount of luminescence. In addition, a large electric field load is applied to the device so that the device inevitably has reduced durability. These problems have not yet been solved even by the use of the organic EL devices described in, for example, Japanese Patent Laid-Open Nos. 2006-261623 and 2006-93665.

SUMMARY OF THE INVENTION

An object of an illustrative, non-limiting embodiment of the invention is to provide an organic electroluminescent device that has achieved both reduction in drive voltage and excellent emission properties; and an organometallic complex compound to be used for the device.

Another object of an illustrative, non-limiting embodiment of the invention is to provide a light emitting apparatus and an illumination apparatus using the device.

According to an aspect of the invention, there are provided the following means.

[1] An organic electroluminescent device comprising:
a pair of electrodes; and
a light emitting layer between the electrodes,
wherein the organic electroluminescent device has a layer containing a compound represented by formula (I):

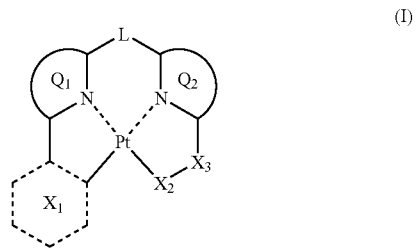

(I)

wherein L represents a divalent linking group, $Q_1$ and $Q_2$ each independently represents an aromatic or aliphatic heterocycle coordinated to Pt through a nitrogen atom, $X_1$ represents a 6-membered ring containing one or more nitrogen atoms, $Q_1$, $Q_2$, and $X_1$ each independently may have a substituent, $X_2$ represents a sulfur atom, a phosphorus atom, an oxygen atom, or a nitrogen atom, and $X_3$ represents a carbon atom, a sulfur atom, or a phosphorus atom.

[2] The organic electroluminescent device as described in [1], wherein the compound represented by formula (I) is a compound represented by formula (II):

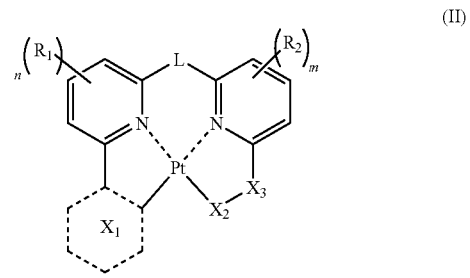

(II)

wherein L, $X_1$, $X_2$, and $X_3$ have the same meanings as in formula (I), $R_1$ and $R_2$ each independently represents a substituent, and m and n each independently represents an integer from 0 to 3.

[3] The organic electroluminescent device as described in [1], wherein the compound represented by formula (I) is a compound represented by formula (III):

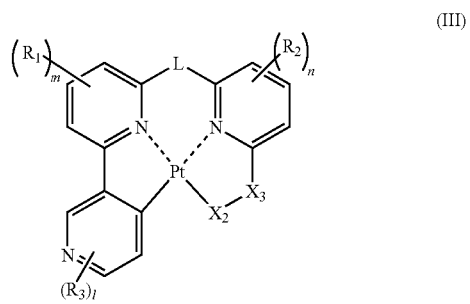

(III)

wherein L, $X_2$, and $X_3$ have the same meanings as in formula (I), $R_1$, $R_2$, and $R_3$ each independently represents a substituent, and m, n, and l each independently represents an integer from 0 to 3.

[4] The organic electroluminescent device as described in [1], wherein the compound represented by formula (I) is a compound represented by formula (IV):

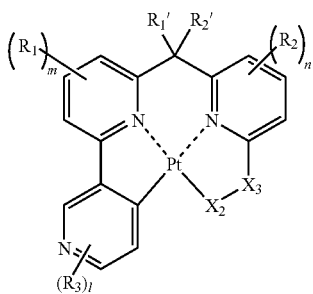

wherein $X_2$ and $X_3$ have the same meanings as in formula (I), $R_1$, $R_2$, and $R_3$ each independently represents a substituent, m, n, and l each independently represents an integer from 0 to 3, and $R_1'$ and $R_2'$ each independently represents a hydrogen atom or a substituent.

[5] The organic electroluminescent device as described in any one of [1] to [4], wherein the layer containing the compound represented by formula (I) is the light emitting layer.

[6] The organic electroluminescent device as described in any one of [1] to [5], wherein the light emitting layer contains a host material.

[7] The organic electroluminescent device as described in [6], wherein the host material is a compound represented by formula (V):

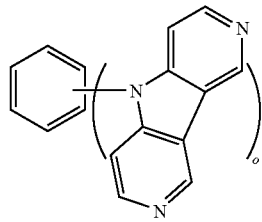

wherein o stands for an integer from 1 to 3.

[8] The organic electroluminescent device as described in any one of [1] to [7], wherein the light emitting layer contains a compound represented by formula (VI):

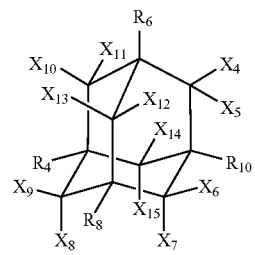

wherein $R_4$, $R_6$, $R_8$, $R_{10}$, and $X_4$ to $X_{15}$ each independently represents a hydrogen atom, an alkyl group, or an aryl group.

[9] The organic electroluminescent device as described in any one of [3] and [5] to [8], wherein the L represents an alkylene group, an arylene group, a heteroarylene group, an imino group, an oxy group, a thio group, a phosphinidene group, or a silylene group.

[10] The organic electroluminescent device as described in any one of [3] and [5] to [8], wherein L represents an arylimino group or —$CR_1'R_2'$—, wherein $R_1'$ and $R_2'$ each represents an alkyl group, an alkyl halide group, or an aryl group.

[11] The organic electroluminescent device as described in any one of [3] and [5] to [9], wherein L represents a phenylimino group, a 3,5-di-tert-butylphenylimino group, or —$CR_1'R_2'$—, wherein $R_1'$ and $R_2'$ each represents an alkyl group, an alkyl halide group, or an aryl group.

[12] The organic electroluminescent device as described in any one of [3] to [11], wherein $R_1$ and the $R_2$ each independently represents a halogen atom, an alkylamino group, an aryl group, or an alkyl group.

[13] The organic electroluminescence device as described in any one of [3] to [12], wherein $R_3$ represents a halogen atom.

[14] A compound represented by formula (III):

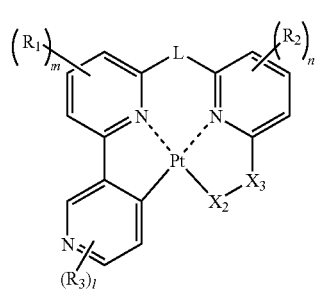

wherein L represents a divalent linking group, $X_2$ represents a sulfur atom, a phosphorus atom, an oxygen atom, or a nitrogen atom, $X_3$ represents a carbon atom, a sulfur atom, or a phosphorus atom, $R_1$, $R_2$, and $R_3$ each independently represents a substituent, and m, n, and l each independently stands for an integer from 0 to 3.

[15] The compound as described in [14], wherein the compound represented by formula (III) is represented by formula (IV):

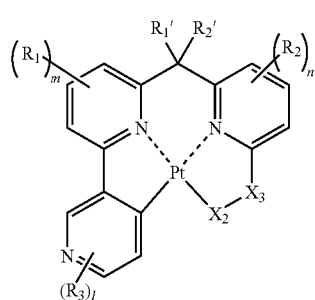

wherein $X_2$ represents a sulfur atom, a phosphorus atom, an oxygen atom, or a nitrogen atom, $X_3$ represents a carbon atom, a sulfur atom, or a phosphorus atom, $R_1$, $R_2$, and $R_3$ each independently represents a substituent, m, n, and l each independently stands for an integer from 0 to 3, and $R_1'$ and $R_2'$ each independently represents a hydrogen atom or a substituent.

[16] The compound as described in [14] or [15], wherein L represents an alkylene group, an arylene group, a heteroarylene group, an imino group, an oxy group, a thio group, a phosphinidene group, or a silylene group.

[17] The compound as described in [14] or [15], wherein L represents an arylimino group or —CR$_1$'R$_2$'—, wherein R$_1$' and R$_2$' each represents an alkyl group, an alkyl halide group, or an aryl group.

[18] The compound as described in [14] or [15], wherein L represents a phenylimino group, a 3,5-di-tert-butylphenylimino group, or —CR$_1$'R$_2$'—, wherein R$_1$' and R$_2$' each represents an alkyl group, an alkyl halide group, or an aryl group.

[19] The compound as described in any one of [14] to [18], wherein R$_1$ and the R$_2$ each independently represents a halogen atom, an alkylamino group, an aryl group, or an alkyl group.

[20] The compound as described in any one of [14] to [19], wherein R$_3$ represents a halogen atom.

[21] A light emitting material comprising a compound as described in [14] or [15].

[22] A light emitting layer comprising a compound a described in [14] or [15] as a light emitting material.

[23] A light emitting apparatus comprising an organic electroluminescent device as described in any one of [1] to [13].

[24] An illumination apparatus comprising an organic electroluminescent device as described in any one of [1] to [13].

[25] The organic electroluminescent device as described in any one of [1] to [13], wherein at least one layer between the pair of electrodes is manufactured by a coating method.

BRIEF DESCRIPTION OF THE DRAWINGS

The features of the invention will appear more fully upon consideration of the exemplary embodiments of the inventions, which are schematically set forth in the drawings, in which.

DETAILED DESCRIPTION OF THE EXEMPLARY EMBODIMENTS

Figure 1:
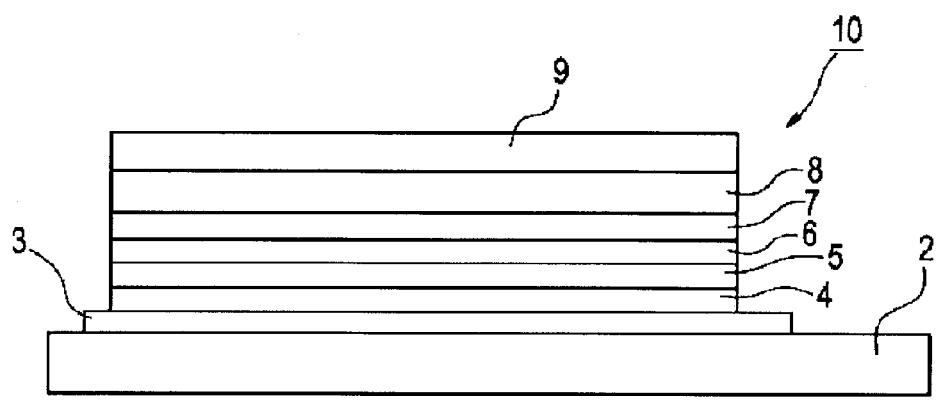
FIG. 1 is a schematic cross-sectional view illustrating an exemplary embodiment of a layer constitution of an organic electroluminescent device of the invention.

The invention makes it possible to provide an organic electroluminescent device that has achieved both excellent emission properties and reduction in drive voltage. In an organic electroluminescent device of the invention, a HOMO-LUMO level is greater than expected and is stabilized by causing high-polarity partial structures containing a hetero atom to exist asymmetrically and as a result, reduction in drive voltage can be achieved. It is particularly effective when the energy cap is large. Specifically, it has a great effect when used in a blue electroluminescent device.

An organometallic complex compound of the invention can provide an organic electroluminescent device having the above-described excellent effect.

A light emitting apparatus and illumination apparatus according to the invention each exhibits excellent emission properties at a low drive voltage because they use the organic electroluminescent device having the above-described excellent effect.

Exemplary embodiments of the invention will be described. In the present invention, "$C_{k-1}$ group" means that the number of carbon atoms in the group is from k to 1.

In the secification, the substituent groups A and B will be defined as described below.

(Substituent Group A)

Substituent group A includes alkyl groups (preferably $C_{1-30}$, more preferably $C_{1-20}$, especially preferably $C_{1-10}$ alkyl groups such as methyl, ethyl, isopropyl, iso-butyl, tert-butyl, n-octyl, n-decyl, n-hexadecyl, cyclopropyl, cyclopentyl, and cyclohexyl), alkenyl groups (preferably $C_{2-30}$, more preferably $C_{2-20}$, especially preferably $C_{2-10}$ alkenyl groups such as vinyl, allyl, 2-butenyl, and 3-pentenyl), alkynyl groups (preferably $C_{2-30}$, more preferably $C_{2-20}$, especially preferably $C_{2-10}$ alkynyl groups such as propargyl and 3-pentynyl), aryl groups (preferably $C_{6-30}$, more preferably $C_{6-20}$, especially preferably $C_{6-12}$ aryl groups such as phenyl, p-methylphenyl, naphthyl, and anthranyl), amino groups (preferably $C_{0-30}$, more preferably $C_{0-20}$, especially preferably $C_{0-10}$ amino groups such as amino, methylamino, dimethylamino, diethylamino, dibenzylamino, diphenylamino, ditolylamino, and pyrrolidinyl), alkoxy groups (preferably $C_{1-30}$, more preferably $C_{1-20}$, especially preferably $C_{1-10}$ alkoxy groups such as methoxy, ethoxy, butoxy, and 2-ethylhexyloxy), aryloxy groups (preferably $C_{6-30}$, more preferably $C_{6-20}$, especially preferably $C_{6-12}$ aryloxy groups such as phenyloxy, 1-naphthyloxy, and 2-naphthyloxy), heterocyclic oxy groups (preferably $C_{1-30}$, more preferably $C_{1-20}$, especially preferably $C_{1-12}$ heterocyclic oxy groups such as pyridyloxy, pyrazyloxy, pyrimidyloxy, and quinolyloxy), acyl groups (preferably $C_{1-30}$, more preferably $C_{1-20}$, especially preferably $C_{1-12}$ acyl groups such as acetyl, benzoyl, formyl, and pivaloyl), alkoxycarbonyl groups (preferably $C_{2-30}$, more preferably $C_{2-20}$, especially preferably $C_{2-12}$ alkoxycarbonyl groups such as methoxycarbonyl and ethoxycarbonyl), aryloxycarbonyl groups (preferably $C_{7-30}$, more preferably $C_{7-20}$, especially preferably $C_{7-12}$ aryloxycarbonyl groups such as phenyloxycarbonyl), acyloxy groups (preferably $C_{2-30}$, more preferably $C_{2-20}$, especially preferably $C_{2-10}$ acyloxy groups such as acetoxy and benzoyloxy), acylamino groups (preferably $C_{2-30}$, more preferably $C_{2-20}$, especially preferably $C_{2-10}$ acylamino groups such as acetylamino and benzoylamino), alkoxycarbonylamino groups (preferably $C_{2-30}$, more preferably $C_{2-20}$, especially preferably $C_{2-12}$ alkoxycarbonylamino groups such as methoxycarbonylamino), aryloxycarbonylamino groups (preferably $C_{7-30}$, more preferably $C_{7-20}$, especially preferably $C_{7-12}$ aryloxycarbonylamino groups such as phenyloxycarbonylamino), sulfonylamino groups (preferably $C_{1-30}$, more preferably $C_{1-20}$, especially preferably $C_{1-12}$ sulfonylamino groups such as methanesulfonylamino and benzenesulfonylamino), sulfamoyl groups (preferably $C_{0-30}$, more preferably $C_{0-20}$, especially preferably $C_{0-12}$ sulfamoyl groups such as sulfamoyl, methylsulfamoyl, dimethylsulfamoyl, and phenylsulfamoyl), carbamoyl groups (preferably $C_{1-30}$, more preferably $C_{1-20}$, especially preferably $C_{1-12}$ carbamoyl groups such as carbamoyl, methylcarbamoyl, diethylcarbamoyl, and phenylcarbamoyl), alkylthio groups (preferably $C_{1-30}$, more preferably $C_{1-20}$, especially preferably $C_{1-12}$ alkylthio groups such as methylthio and ethylthio), arylthio groups (preferably $C_{6-30}$, more preferably $C_{6-20}$, especially preferably $C_{6-12}$ arylthio groups such as phenylthio), heterocyclic thio groups (preferably $C_{1-30}$, more preferably $C_{1-20}$, especially preferably $C_{1-12}$ heterocyclic thio groups such as pyridylthio, 2-benzimidazolylthio, 2-benzoxazolylthio, and 2-benzthiazolylthio), sulfonyl groups (preferably $C_{1-30}$, more preferably $C_{1-20}$, especially preferably $C_{1-12}$ sulfonyl groups such as mesyl and tosyl), sulfinyl groups (preferably $C_{1-30}$, more preferably $C_{1-20}$, especially preferably $C_{1-12}$ sulfinyl groups such as methanesulfinyl and benzenesulfinyl), ureido groups (preferably $C_{1-30}$, more preferably $C_{1-20}$, especially preferably $C_{1-12}$ ureido groups such as ureido, methylureido, and phenylureido), phosphoric acid amide groups (preferably $C_{1-30}$, more preferably $C_{1-20}$, especially preferably $C_{1-12}$ phosphoric acid amide groups such as diethylphosphoric acid amide and phenylphosphoric acid amide), a hydroxy group, a mercapto group, halogen atoms (such as fluorine, chlorine, bromine, and iodine atoms), a cyano group, a sulfo group, a carboxyl group, a nitro group, a hydroxamic acid group, a sulfino group, a hydrazino group, an imino group, heterocyclic (heteroaryl) groups (that are preferably $C_{1-30}$, more preferably $C_{1-12}$ heterocyclic groups having, as a heteroatom, a nitrogen atom, an oxygen atom, a sulfur atom, a phosphorus atom, a silicon atom, a selenium atom, or a tellurium atom and specifically include pyridyl, pyrazinyl, pyrimidyl (pyrimidinyl), pyridazinyl, pyrrolyl, pyrazolyl, triazolyl, imidazolyl, oxazolyl, thiazolyl, isoxazolyl, isothiazolyl, quinolyl, furyl, thienyl, selenienyl, tellurienyl, piperidyl, piperidino, morpholino, pyrrolidyl, pyrrolidino, benzoxazolyl, benzimidazolyl, benzothiazolyl, carbazolyl, azepinyl, and silolyl), silyl groups (preferably $C_{3-40}$, more preferably $C_{3-30}$, especially preferably $C_{3-24}$ silyl groups such as trimethylsilyl and triphenylsilyl), silyloxy groups (preferably $C_{3-40}$, more preferably $C_{3-30}$, especially preferably $C_{3-24}$ silyloxy groups such as trimethylsilyloxy and triphenylsilyloxy), and phosphoryl groups (such as diphenylphosphoryl and dimethylphosphoryl).
(Substituent Group B)

Substituent group B includes alkyl groups (preferably $C_{1-30}$, more preferably $C_{1-20}$, especially preferably $C_{1-10}$ alkyl groups such as methyl, ethyl, isopropyl, tert-butyl, n-octyl, n-decyl, n-hexadecyl, cyclopropyl, cyclopentyl, and cyclohexyl), alkenyl groups (preferably $C_{2-30}$, more preferably $C_{2-20}$, especially preferably $C_{2-10}$ alkenyl groups such as vinyl, allyl, 2-butenyl, and 3-pentenyl), alkynyl groups (preferably $C_{2-30}$, more preferably $C_{2-20}$, especially preferably $C_{2-10}$ alkynyl groups such as propargyl and 3-pentynyl), aryl groups (preferably $C_{6-30}$, more preferably $C_{6-20}$, especially preferably $C_{6-12}$ aryl groups such as phenyl, p-methylphenyl, naphthyl, and anthranyl), a cyano group, heterocyclic groups (that include aromatic heterocyclic groups, are preferably $C_{1-30}$, more preferably $C_{1-12}$ heterocyclic groups having, as a heteroatom, a nitrogen atom, an oxygen atom, a sulfur atom, a phosphorus atom, a silicon atom, a selenium atom, or a tellurium atom, and specifically include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenienyl, tellurienyl, piperidyl, piperidino, morpholino, pyrrolidyl, pyrrolidino, benzoxazolyl, benzimidazolyl, benzothiazolyl, carbazolyl, azepinyl, and silolyl).

These substituents may be substituted further with another substituent and as the another substituent, those selected from the above-described substituent groups may be employed.

In the invention, the number of carbon atoms of the substituent such as alkyl group includes the number of carbon atoms of another substituent in the case where the substituent such as alkyl group may be substituted with the another substituent.

An organic electroluminescent device of the invention has a light emitting layer between a pair of electrodes and it has a layer containing a compound represented by the following formula (I).

In the description of the following formulae (I), (II), (III), (IV), and (V), a hydrogen atom embraces an isotope thereof (such as deuterium atom) and also an atom constituting the substituent embraces an isotope of the atom.

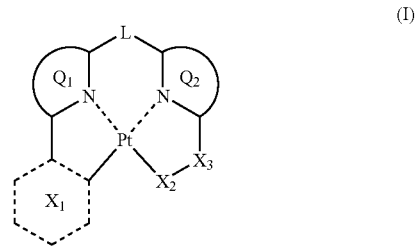

(I)

In the formula (I), L represents a divalent linking group. $Q_1$ and $Q_2$ each independently represents an aromatic or aliphatic heterocycle coordinated to Pt through a nitrogen atom, $X_1$ represents a 6-membered ring containing at least one nitrogen atom. $X_2$ represents a sulfur atom, a phosphorus atom, an oxygen atom or a nitrogen atom. $X_3$ represents a carbon atom, a sulfur atom, or a phosphorus atom.

L represents a divalent linking group. Since all the bonds from platinum in the tetradentate complex of platinum are present on one plane, the complex is apt to have a planar structure. It is therefore known that the complex often forms an associate due to interactions between a π orbit or dipole moment of the ligand and a dz orbit of platinum. The associate has a narrow energy gap so that it deteriorates a sharp emission spectrum or luminous efficiency. L has a strong effect on the polar moment of a molecule. With a decrease in the polar moment of a molecule, associated luminescence of complexes can be suppressed and color purity can be improved.

The divalent linking group represented L has preferably a lower polarity. Examples of it include alkylene groups (such as methylene, ethylene, tetramethylethylene, propylene, and cyclohexanediyl), arylene groups (such as phenylene and naphthalenediyl), heteroarylene groups (such as pyridinediyl, furandiyl, and thiophenediyl), imino groups (—NR—) (such as phenylimino), an oxy group (—O—), a dioxanediyl group, a thio group (—S—), a sulfonyl group (—SO$_2$—), a phosphinidene group (—PR—) (such as phenylphosphinidene), and silylene groups (—SiRR'—) (such as dimethylsilylene, di-iso-propylsilylene, methylphenylsilylene, and diphenylsilylene), and combinations thereof. These linking groups may further have a substituent. Examples of the substituent include those listed in the substituent group A.

Preferred examples of L include alkylene groups (such as methylene, ethylene, tetramethylethylene, propylene, and cyclohexanediyl), arylene groups (such as phenylene and naphthalenediyl), heteroarylene groups (such as pyridinediyl, furandiyl, and thiophenediyl), imino groups (—NR—) (such as an alkylimino group, e.g. methylimino or ethylimino, an arylimino group, e.g., phenylimino, naphthylimino, or 3,5-di-tert-butylphenylimino, a heteroarylimino group, e.g., pyridinylimino, or a methylbenzenesulfonylimino), an oxy group (—O—), a dioxanediyl group, a thio group (—S—), a sulfonyl group (—SO$_2$—), and silylene groups (—SiRR'—) (such as dimethylsilylene, di-iso-propylsilylene, methylphenylsilylene, and diphenylsilylene). Of these, an arylimino group or —CR$_1$'R$_2$'— are more preferred, a phenylimino group, a 3,5-di-tert-butylphenylimino group, and —CR$_1$'R$_2$'— are still more preferred, and —CR$_1$'R$_2$'— is especially preferred. L represents especially preferably —CR$_1$'R$_2$'—.

R$_1$' and R$_2$' each independently represents a hydrogen atom or a substituent. Examples of the substituent include those listed in the substituent group A.

From the standpoint of suppressing a polar moment of the molecule, $R_1'$ and $R_2'$ each represents preferably an alkyl group, an alkyl halide group, or an aryl group, more preferably a methyl group, an ethyl group, an iso-butyl group, a tert-butyl group, a perfluoromethyl group, a phenyl group, a pyridinyl group, or a methylimidazolyl group, with a methyl group, an iso-butyl group, or a phenyl group being still more preferred.

$R_1'$ and $R_2'$ may be coupled together to form a ring. The following (c1) to (c3) are modes of $R_1'$ and $R_2'$ forming a ring. Of these, modes of (c1) and (c3) are preferred.

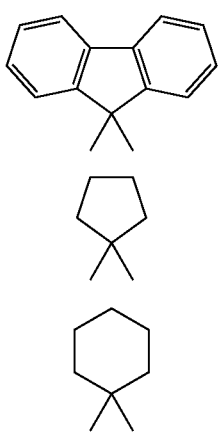

(c1)

(c2)

(c3)

$Q_1$ and $Q_2$ each independently represents an aromatic or aliphatic heterocycle coordinated to Pt through a nitrogen atom. From the standpoint of maintaining a film forming property by vapor deposition, $Q_1$ and $Q_2$ each represents preferably the above heterocycle having 13 or less carbon atoms.

The heterocycle may have a substituent. Examples of the substituent include those listed in the substituent group A. From the standpoint of chemical stability, preferred are halogen atoms, a cyano group, a silyl group, alkylamino groups, arylamino groups, alkyl groups, aryl groups, heteroaryl groups, alkoxy groups, and aryloxy groups, with halogen atoms, a cyano group, alkylamino groups, and alkyl groups being more preferred.

$Q^1$ and $Q^2$ have a great influence mainly on the emission wavelength and the effect of the invention is marked in a blue region so that they are preferably pyridine, pyrimidine, pyrazine, imidazole, or pyrazole having a blue light emitting structure, more preferably pyridine or pyrimidine. Of these, the following structures are still more preferred, with (Ia) being most preferred.

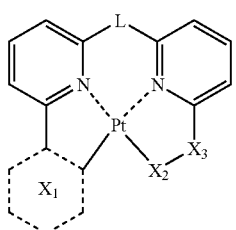

(Ia)

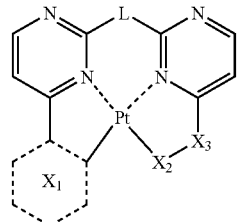

(Ib)

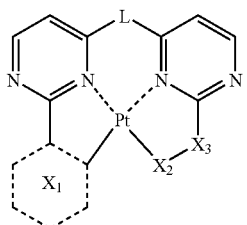

(Ic)

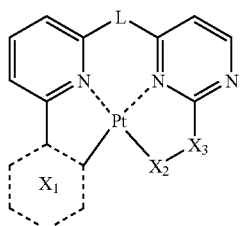

(Id)

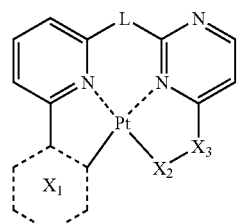

(Ie)

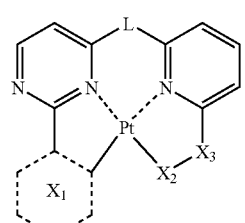

(If)

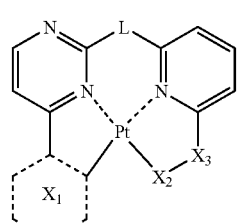

(Ig)

$X_1$ represents a 6-membered ring containing one or more nitrogen atoms. The 6-membered ring may have a substituent. Examples of the substituent include those listed in the substituent group A. From the standpoint of chemical stability, halogen atoms, a cyano group, alkyl groups, aryl groups, heteroaryl groups, a silyl group, alkylamino groups, and arylamino groups are preferred. These substituents may be substituted further with another substituent. Examples of the another substituent include those listed in the substituent group A. The another substituent is preferably a halogen atom, more preferably a fluorine atom. As the substituent of $X_1$, halogen atoms (especially preferably, a fluorine atom), a cyano group, alkyl halide groups (especially preferably, a perfluoromethyl group, a perfluoroethyl group, and a perfluoropropyl group), and alkyl groups are preferred, with a fluorine atom being most preferred.

Examples of $X_1$ include pyridyl, pyrimidinyl, pyrazinyl, and pyridazinyl.

From the standpoint of heat stability, $X_1$ is preferably coordinated to Pt through a carbon atom. From the standpoint of heat stability, $X_1$ is preferably an aromatic ring.

$X_1$ has a great influence mainly on the emission wavelength and the effect of the invention is marked in a blue color region so that it has preferably a blue light emitting structure. The following are specific preferred structures and of these, (Ih) has the most preferred structure.

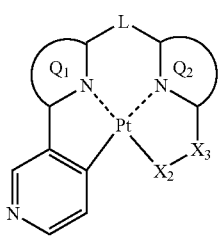

(Ih)

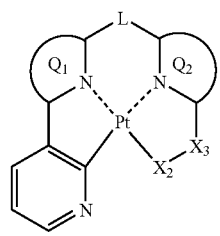

(Ii)

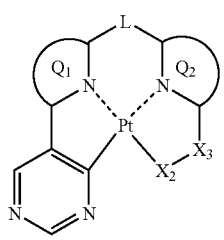

(Ij)

$X_2$ represents a sulfur atom, a phosphorus atom, an oxygen atom, or a nitrogen atom and these atoms may have a substituent.

Examples of the substituent include those listed in the substituent group A. Of these, alkyl groups, aryl groups, arylalkyl groups, acyl groups, alkylsulfonyl groups, arylsulfonyl groups, arylthio groups and heterocyclic groups are preferred, with a methyl group, a perfluoromethyl group, a tert-butyl group, a tert-butyl group substituted with a phenyl group, a phenyl group, a phenylcarboyl group, a phenylthio group, an acetyl group, a perfluoromethanecarbonyl group, a mesyl group, a tosyl group, a perfluoromethanesulfonyl group, a pyridinyl group, a pyrimidinyl group, and the like being more preferred.

$X_2$ is preferably a nitrogen atom or an oxygen atom from the standpoint of binding strength with platinum, with an oxygen atom being more preferred.

$X_3$ represents a carbon atom, a sulfur atom, or a phosphorus atom and these atoms may have a substituent.

Examples of the substituent include those listed in the substituent group A. Of these, alkyl groups, aryl groups, alkoxy groups, and aryloxy groups are preferred. When $X_3$ represents a carbon atom, the carbon atom may form a carbonyl group, an imino group, or a thiocarbonyl group.

When $X_3$ represents a sulfur atom, the sulfur atom may form a sulfonyl group.

When $X_3$ represents a phosphorus atom, it is preferably a pentavalent phosphorus atom from the standpoint of stability. When the phosphorus atom is pentavalent, it may form a substituted or unsubstituted phosphoryl group. When the phosphoryl group has a substituent, examples of the substituent include those listed in the substituent group A. Of these, alkyl groups, aryl groups, alkoxy groups, and aryloxy groups are preferred.

Since the sites of $X_2$ and $X_3$ are exposed to acid and high-temperature conditions as a result of complexation, they are required to be chemically stable against acid and heat. In order that the complex thus obtained forms a rigid bond with a platinum atom, partial structures of $X_2$ and $X_3$ represented by the following formulae (i) to (v) are preferred as a combination of $X_3$ and a substituent thereof.

The following are examples of partial structures of $X_2$ and $X_3$ (the following formulae (i) to (v)) extracted from the formula (I) as the combination of $X_3$ and a substituent thereof.

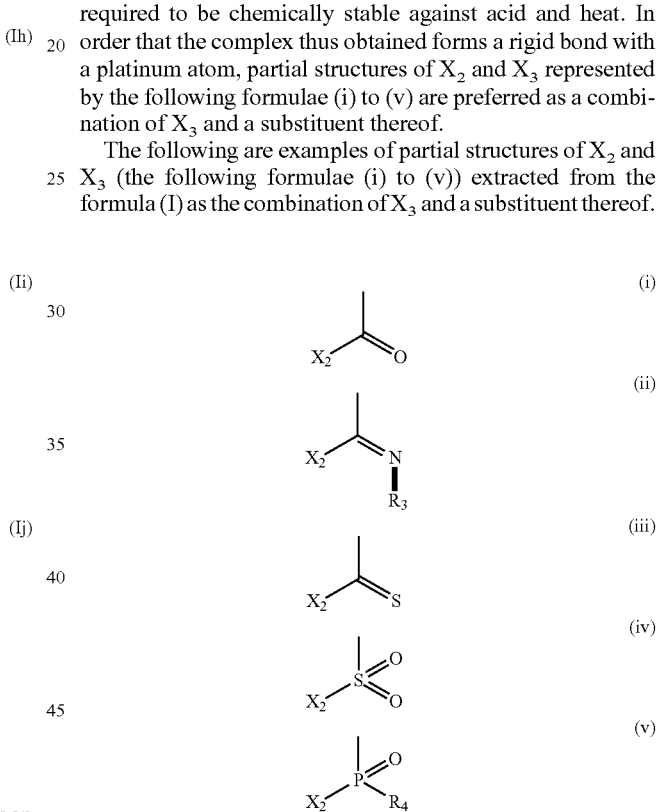

$R_3$ represents a substituent and examples of the substituent include those listed in the substituent group A. Of these, alkyl groups, aryl groups, sulfonyl groups, and sulfinyl groups are preferred, with alkyl groups and aryl groups being more preferred.

$R_4$ represents a substituent and examples of the substituent include those listed in the substituent group A. Of these, alkyl groups, aryl groups, alkoxy groups, aryloxy groups, and heterocyclic groups are preferred, with a methyl group, a tert-butyl group, a phenyl group, a methoxyl group, a phenol group, and a pyidinyl group being more preferred.

$X_3$ is preferably a carbon atom from the standpoint of heat stability and it is most preferred that the carbon atom forms a carbonyl group.

Further, these $X_2$ and $X_3$ do not form a cyclic structure.

Of the formulae (i) to (v), the formulae (i), (iv), and (v) are preferred, with the formula (I) being more preferred.

The followings are specific examples of the formulae (i) to (v), but the invention is not limited by them.

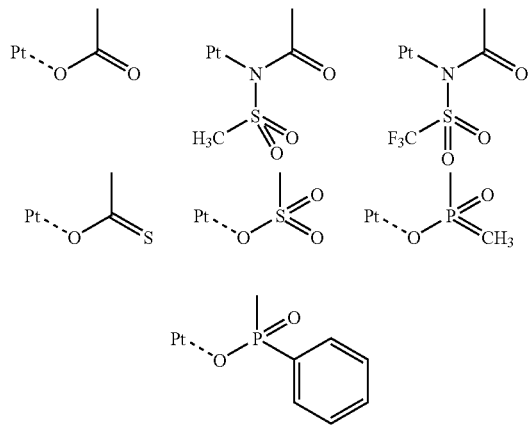

In the invention, the compound represented by the formula (I) is preferably a compound represented by the following formula (II).

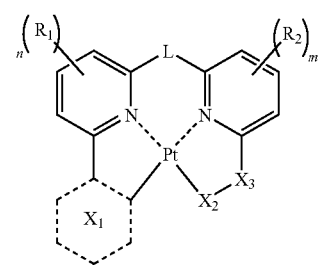

(II)

In the formula (II), L, $X_1$, $X_2$, and $X_3$ have the same meanings as in the formula (I) and the preferred ranges of them are also the same.

$R_1$ and $R_2$ each independently represents a substituent and m and n each independently represents an integer from 0 to 3. When m is an integer of 2 or greater, $R_2$s may be the same or different. When n is an integer of 2 or greater, $R_1$s may be the same or different. Specific examples of $R_1$ and $R_2$ include those listed in the substituent group A. From the standpoint of chemical stability, halogen atoms, a cyano group, silyl groups, alkylamino groups, arylamino groups, alkyl groups, alkyl halide groups, aryl groups, aryl halide groups, heteroaryl groups, alkoxy groups, and aryloxy groups are preferred, of which halogen atoms, a cyano group, alkylamino groups, alkyl groups, aryl groups, alkyl halide groups (especially preferably a trifluoromethyl group), and aryl halide groups (especially preferably a fluorine-substituted phenyl group) are more preferred; halogen atoms (especially preferably, a fluorine atom and a chlorine atom), alkylamino groups (especially preferably a dimethylamino group, a methylphenylamino group, and a pyrrolidinyl group), alkyl groups (especially preferably a methyl group), and aryl groups (especially preferably, a phenyl group, a naphthyl group) are still more preferred; and a fluorine atom, a methyl group, a phenyl group a dimethylamino group, and a pyrrolidinyl group are most preferred. With regard to the binding position and the number of bonds of the substituent, the following structures are preferred.

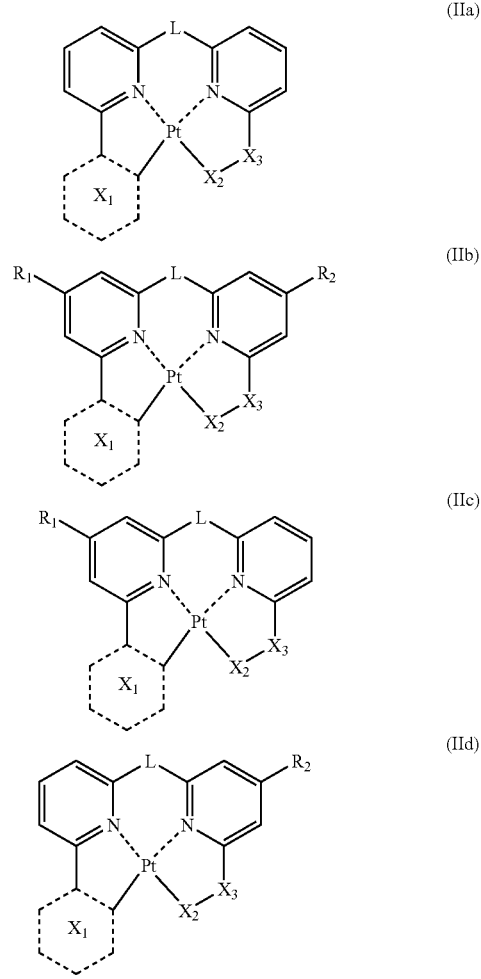

The compound represented by the formula (II) is advantageous because the compound has a short emission wavelength and exhibits the effect of the invention markedly in a blue light emission region compared with the other compounds.

In the invention, the compound represented by the formula (I) is preferably a compound represented by the following formula (III):

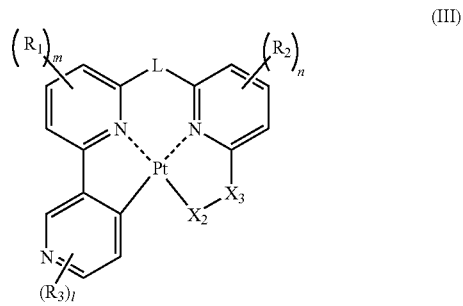

(III)

In the formula (III), L, $X_2$, $X_3$, $R_1$, $R_2$, m, and n have the same meanings as in the formula (II) and the preferred ranges of them are also the same.

$R_3$ represents a substituent and l stands for an integer from 0 to 3. When l stands for an integer of 2 or greater, $R_3$s may be the same or different. Specific examples of $R_3$ include those listed in the substituent group A. From the standpoint of chemical stability, halogen atoms, a cyano group, alkyl groups, alkyl halide groups, aryl groups, heteroaryl groups, silyl groups, alkylamino groups, and arylamino groups are preferred, of which halogen atoms (especially preferably a fluorine atom), a cyano group, alkyl halide groups (especially preferably a perfluoromethyl group, a perfluoroethyl group, and a perfluoropropyl group), alkyl groups are more preferred, halogen atoms are still more preferred, and a fluorine atom being most preferred. With regard to the binding position and the number of bonds of the substituent, the following structures are preferred from the standpoint of synthesis ease.

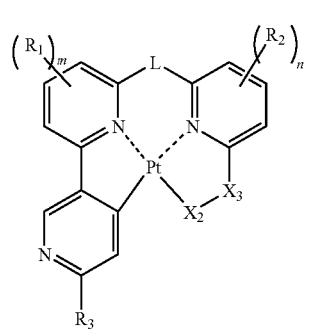
(IIIa)

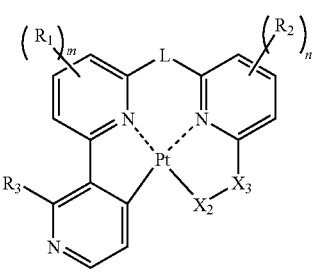
(IIIb)

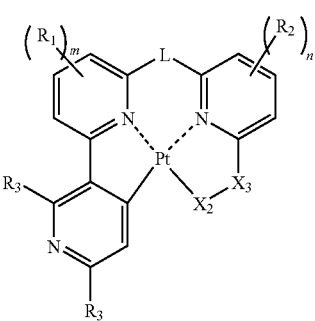
(IIIc)

The following structures are most preferred as a combination of the substitution positions.

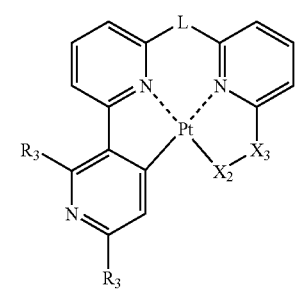
(IIId)

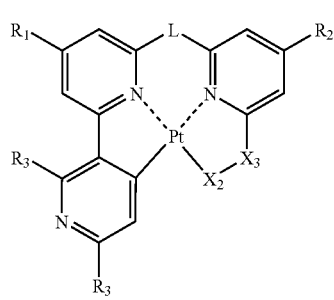
(IIIe)

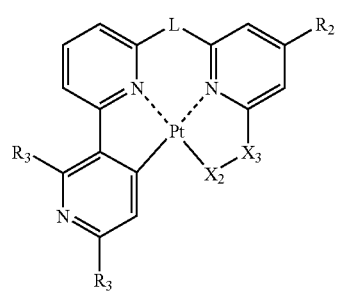
(IIIf)

The compound represented by the formula (III) is advantageous because it has a short emission wavelength and exhibits the effect of the invention in a blue light emission region markedly compared with the other compounds.

In the invention, the compound represented by the formula (I) is preferably a compound represented by the following formula (IV).

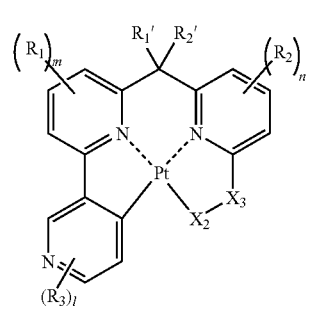
(IV)

In the formula (IV), $X_2$, $X_3$, $R_1$, $R_2$, $R_3$, m, n, and l have the same meanings as in the formula (III) and the preferred ranges of them are also the same, and $R_1'$ and $R_2'$ have the same meanings as in the formula (I) and the preferred ranges of them are also the same.

The molecular weight of the compound represented by the formula (I), (II), (III), or (IV) in the invention is preferably 2000 or less from the standpoints of deposition suitability or solubility, because an organic electroluminescent device is fabricated using a vacuum deposition process or solution application process. It is more preferably 1200 or less, especially preferably 1000 or less. The molecular weight is preferably 250 or greater, more preferably 350 or greater, especially preferably 400 or greater, because from the standpoint of deposition suitability, when the molecular weight is too small, vapor pressure decreases and a change from a gas phase to a solid phase does not occur, making it difficult to form an organic layer.

The function of the compound represented by the formula (I) is not limited and a layer containing the compound represented by the formula (I) is preferably a light emitting layer. When the device has a plurality of organic layers, the compound represented by the formula (I) may be incorporated in any layer other than the layer containing the compound. The compound represented by the formula (I) is contained preferably in a light emitting layer as a light emitting material or a host material, more preferably in a light emitting layer as a light emitting material, especially preferably in a light emitting layer together with at least one host material.

The following are specific examples of the compound represented by the formula (I), (II), (III), or (IV) in the invention, but the invention is not limited to them.

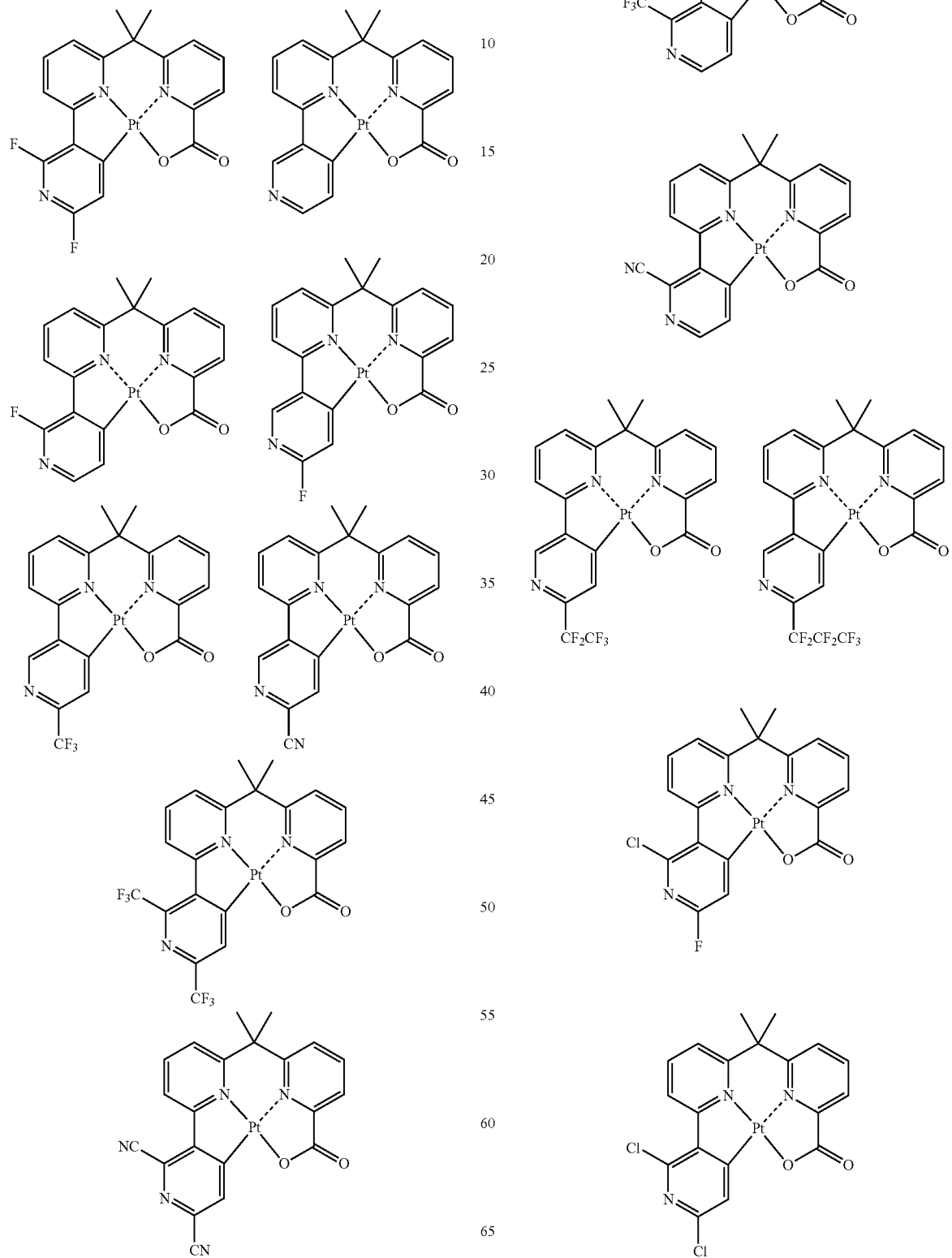

-continued
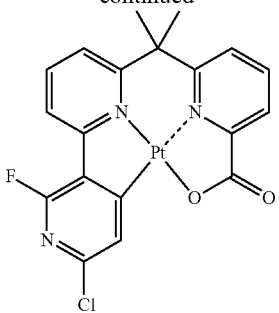
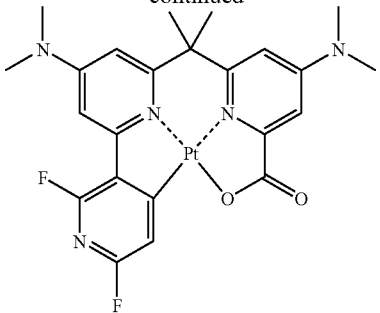
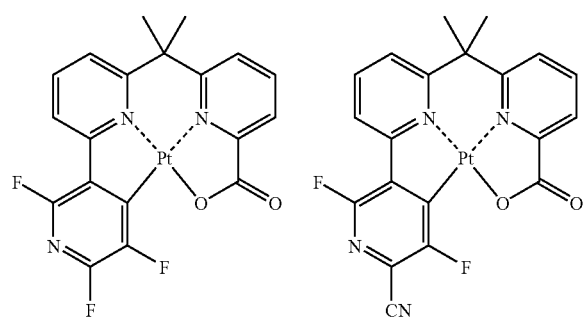
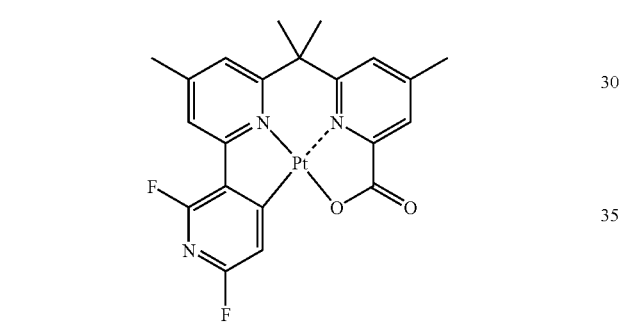
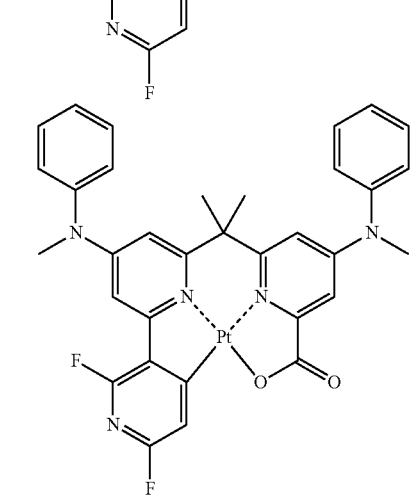
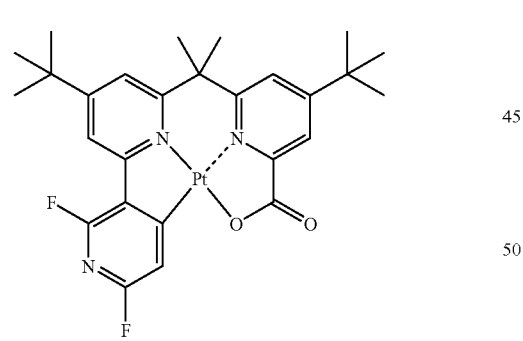
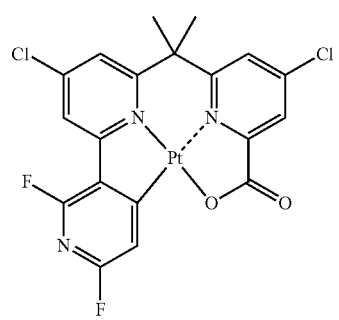
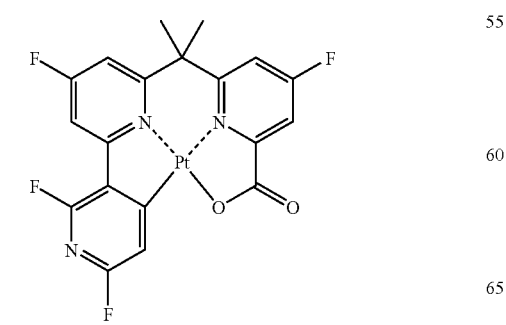
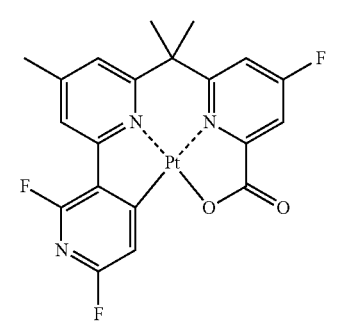

21
-continued
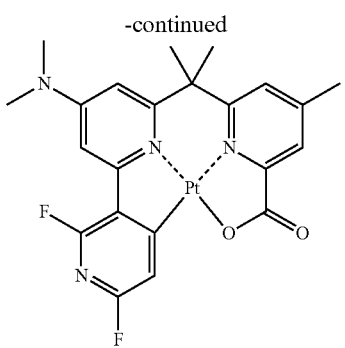
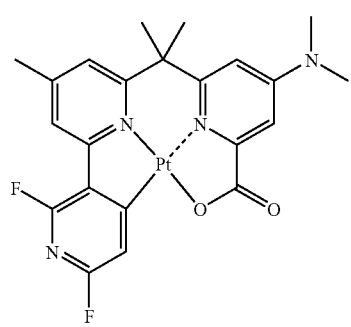
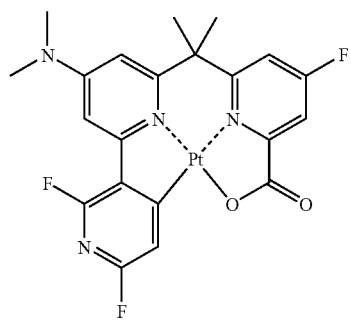
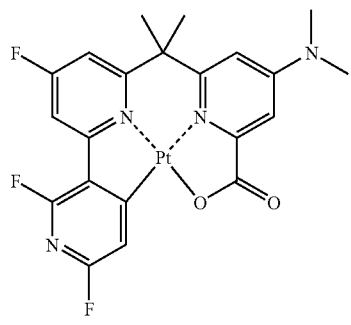
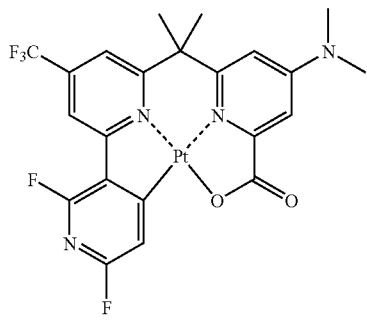
22
-continued
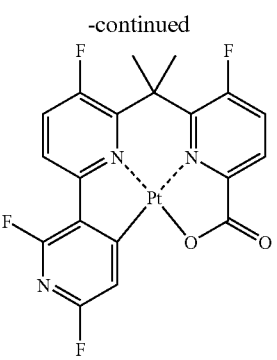
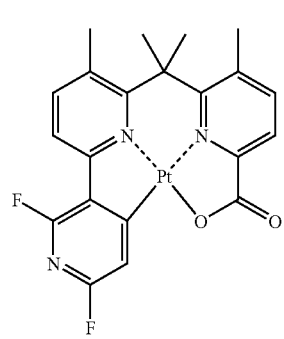
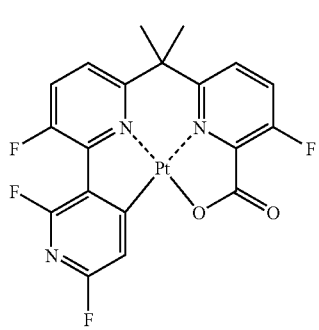
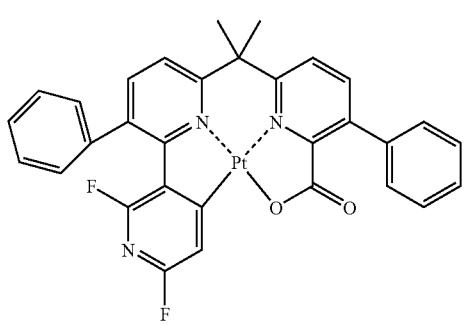
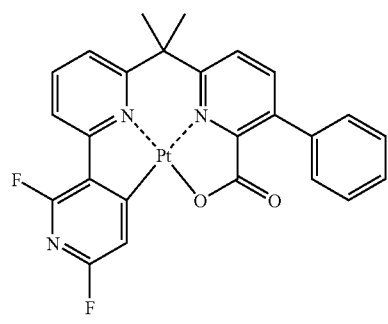

-continued
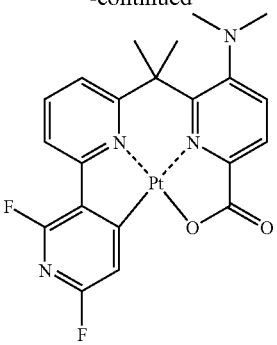
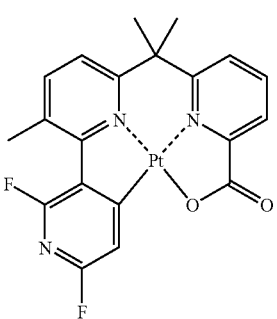
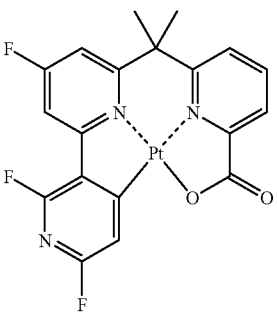
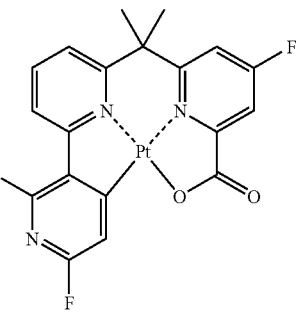
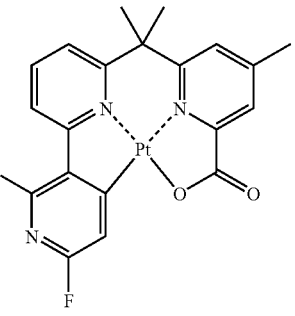
-continued
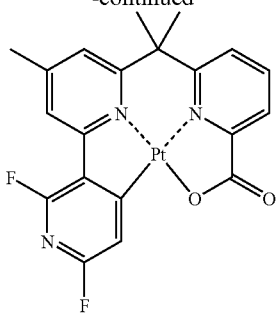
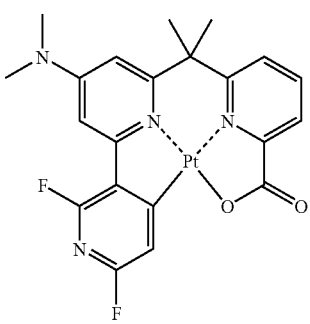
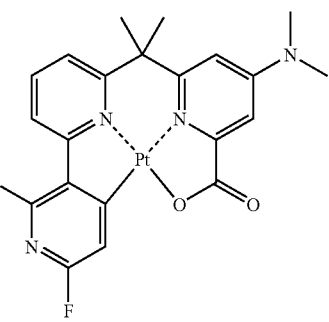
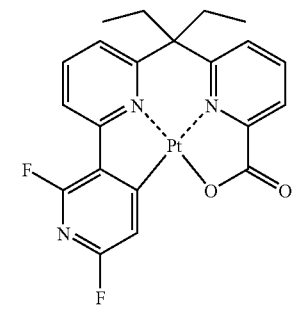
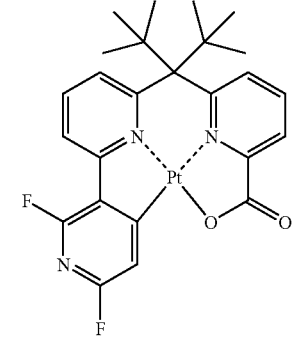

25
-continued
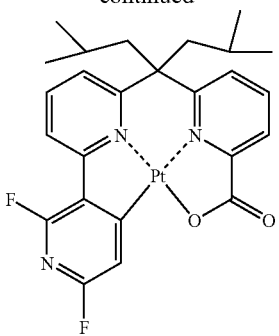
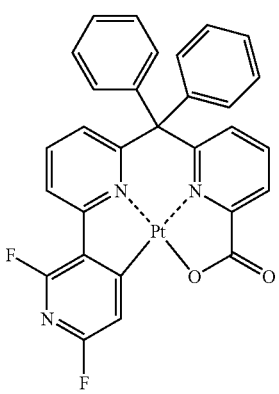
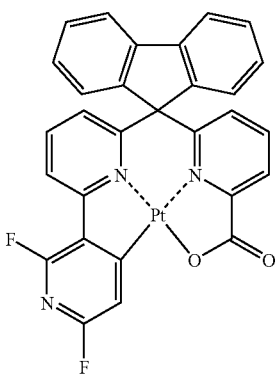
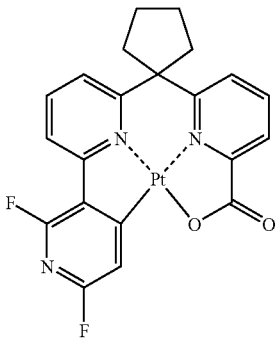
26
-continued
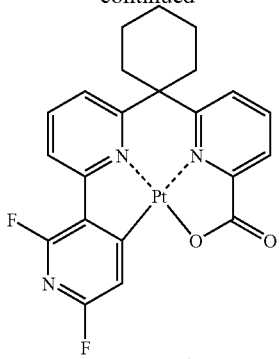
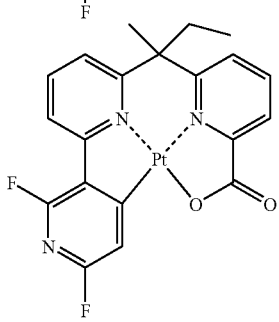
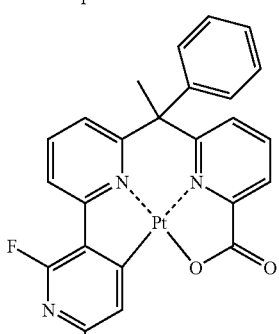
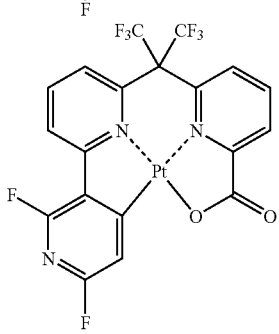
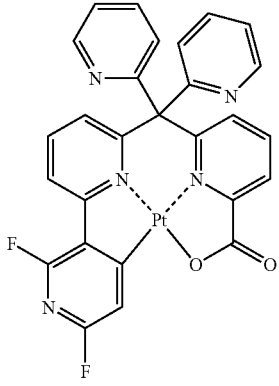

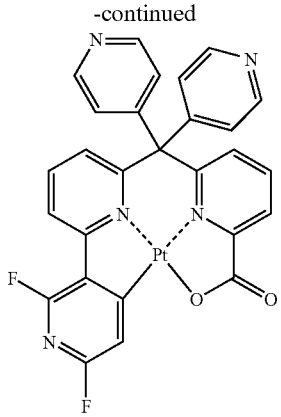
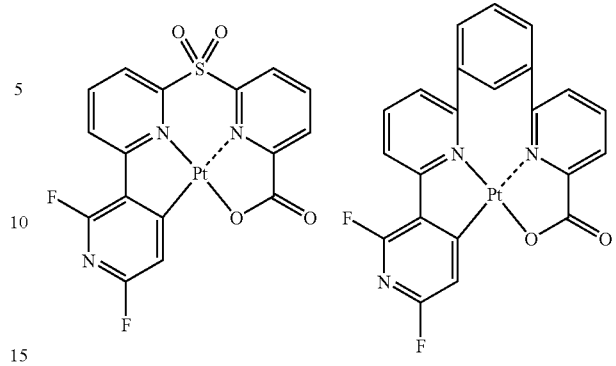
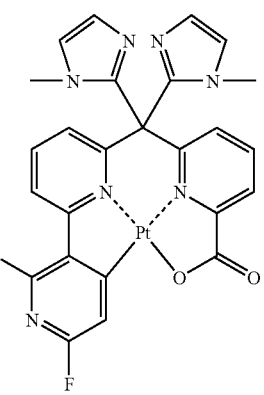
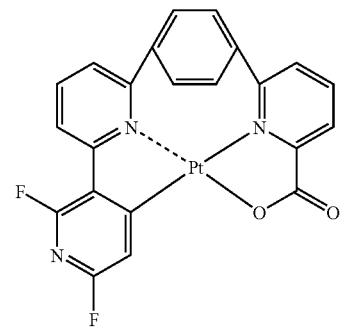
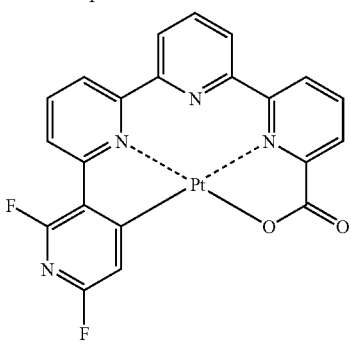
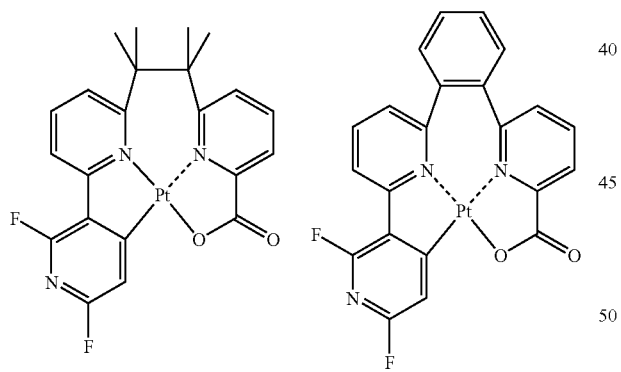
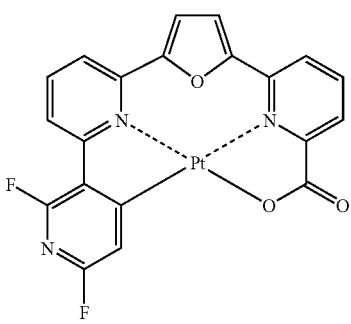
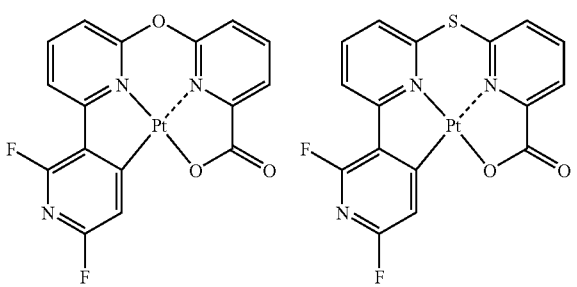
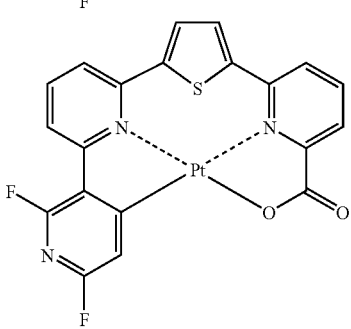

29
-continued
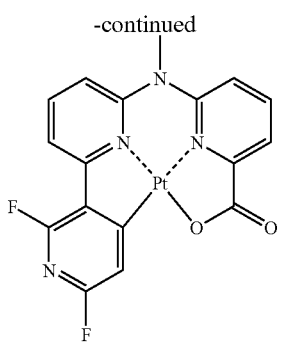
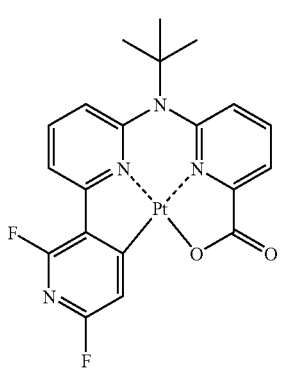
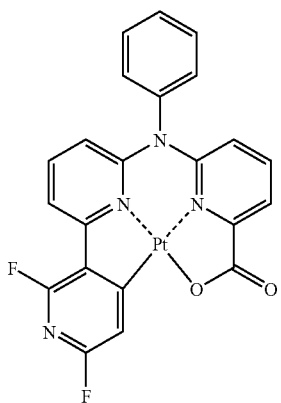
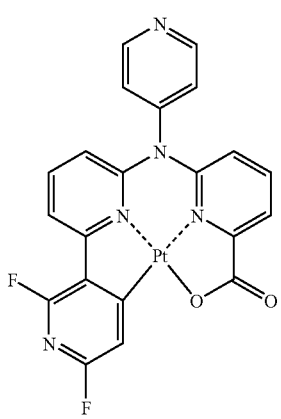
30
-continued
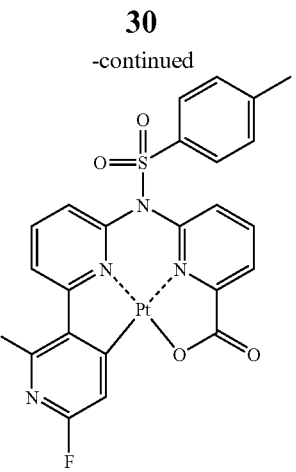
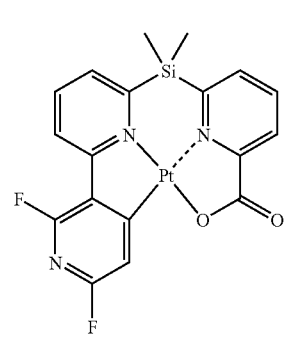
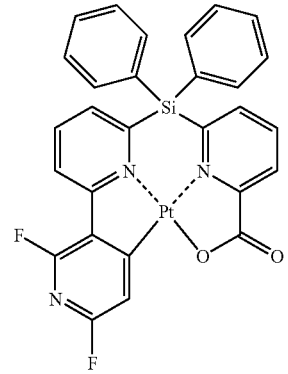
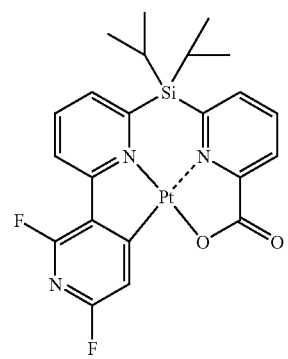

-continued
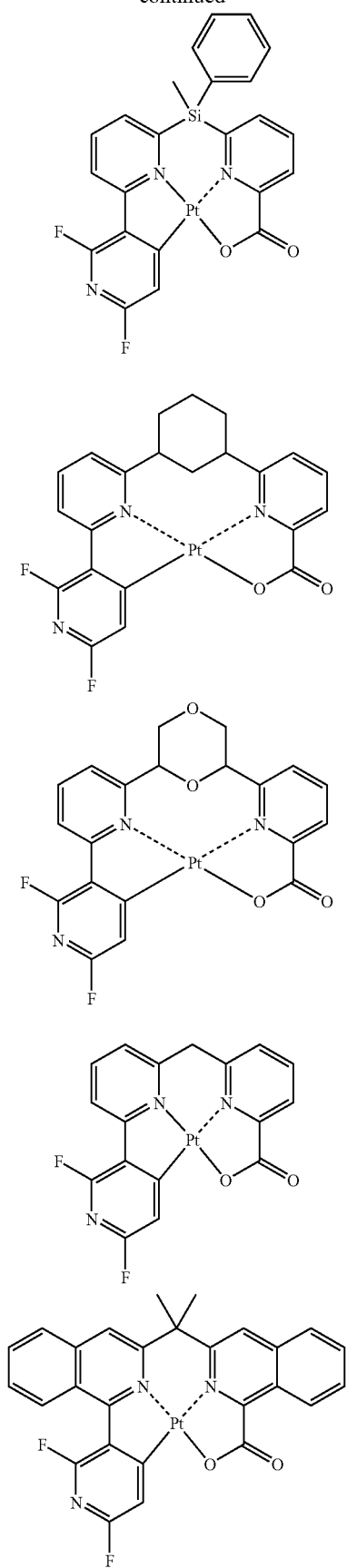
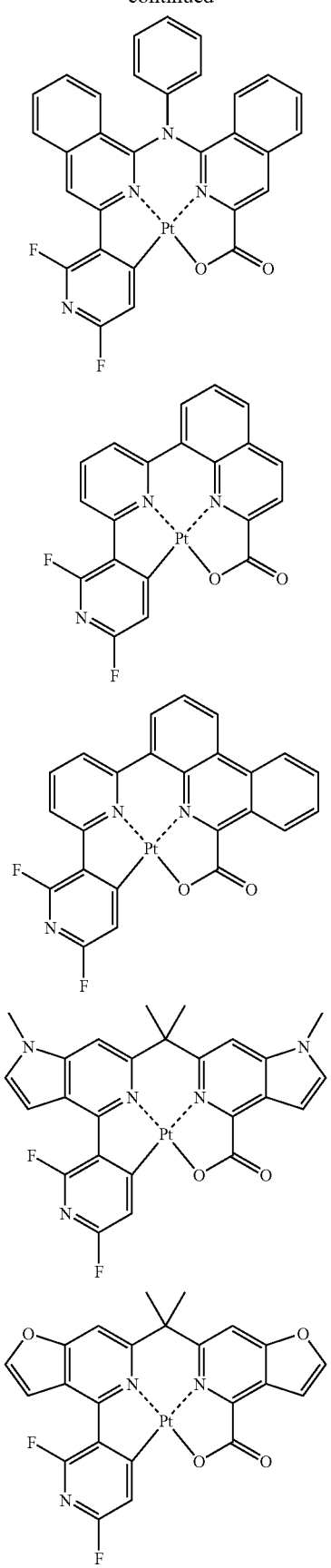

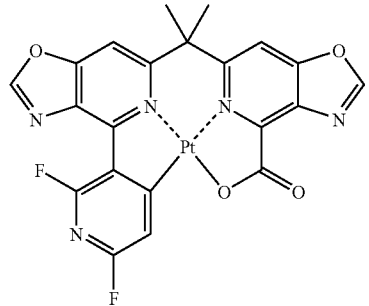
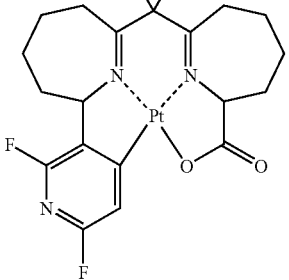
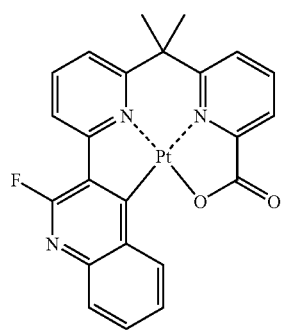
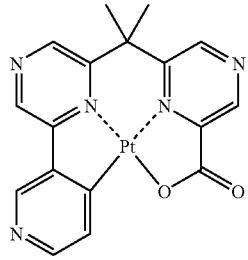
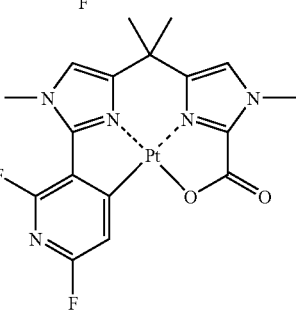
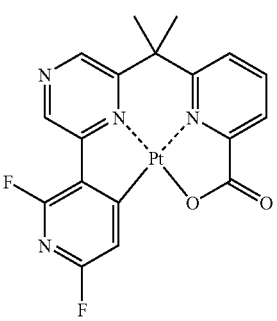
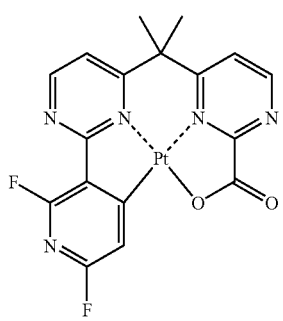
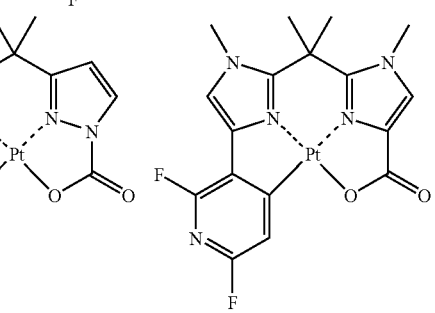
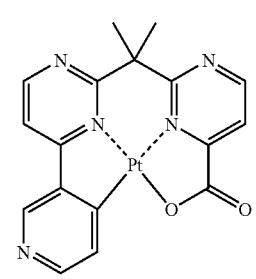
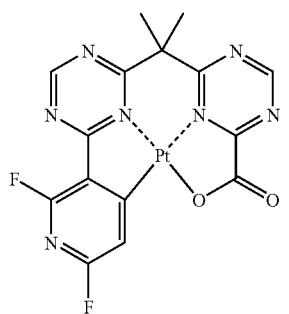
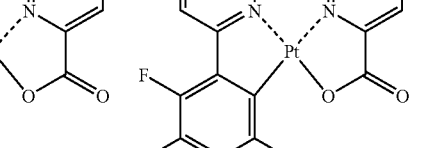
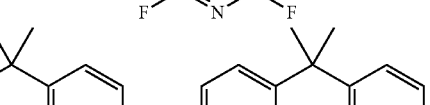
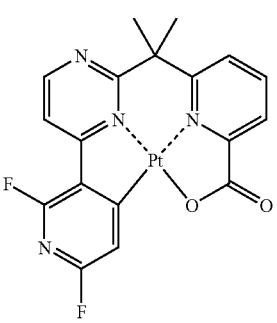
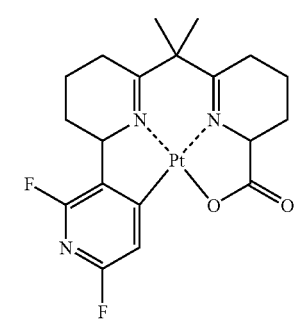
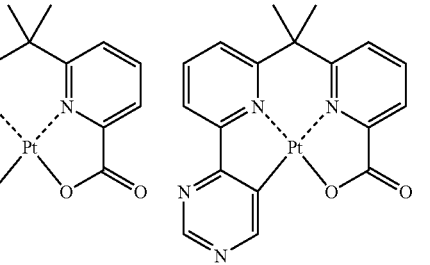

-continued
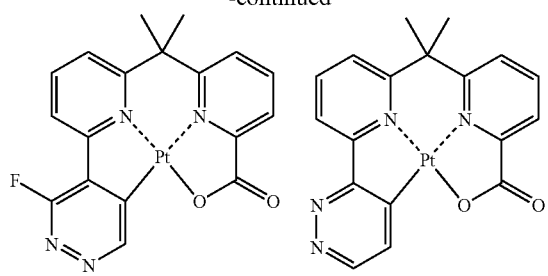
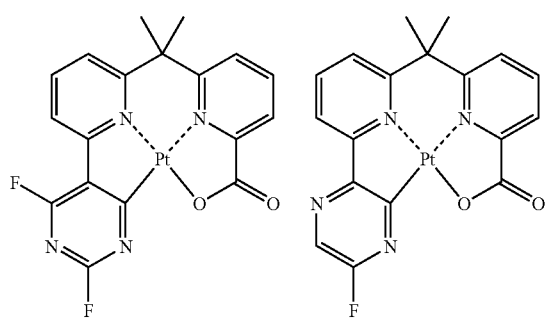
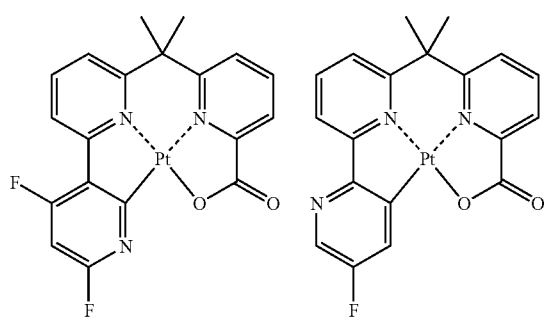
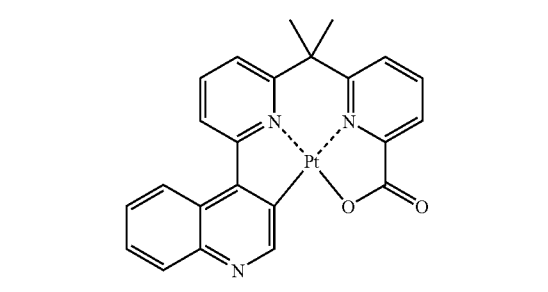
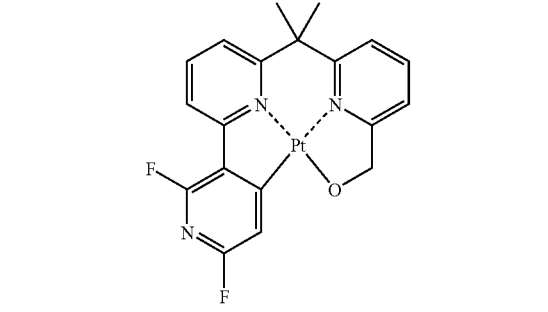
-continued
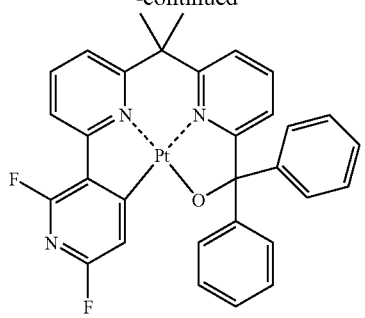
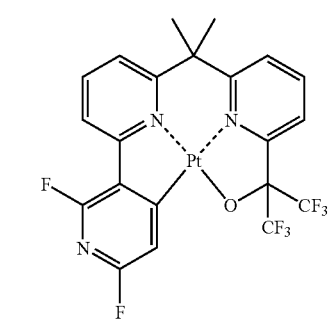
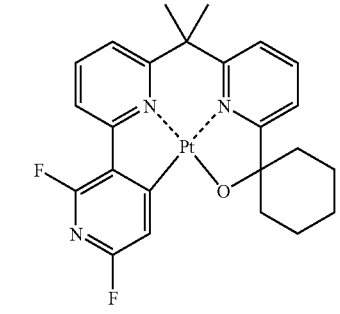
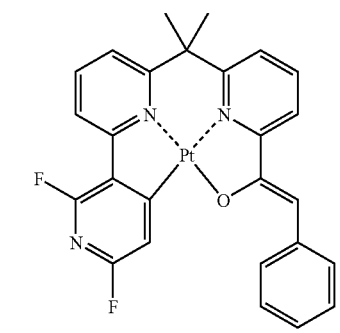
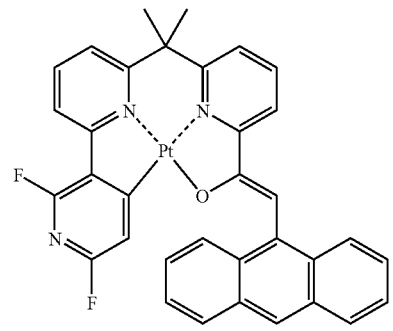

37
-continued
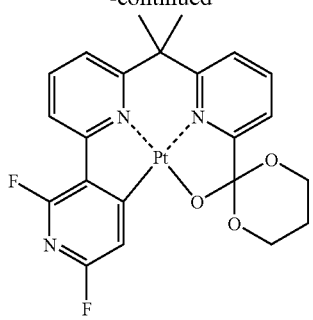
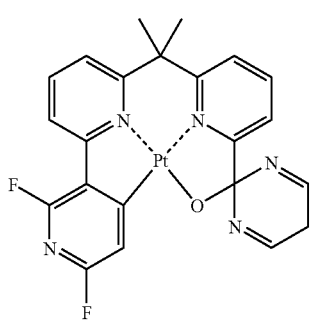
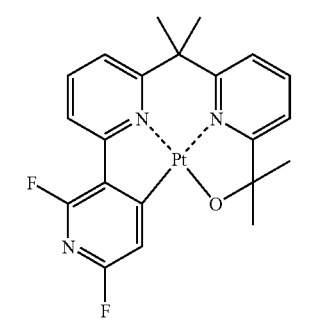
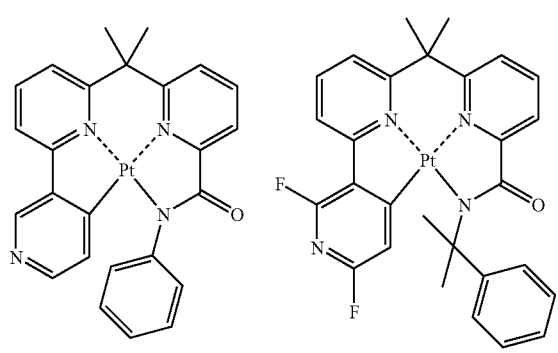
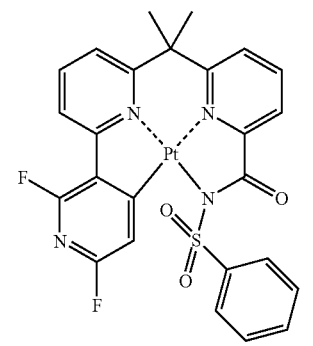
38
-continued
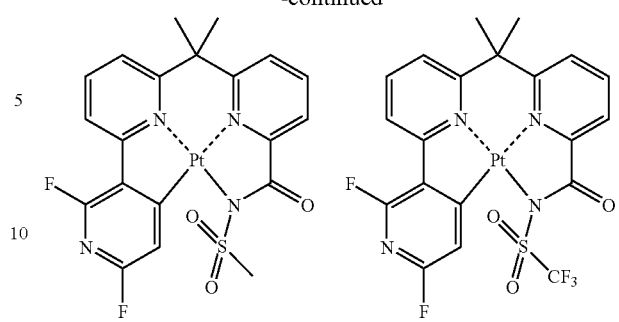
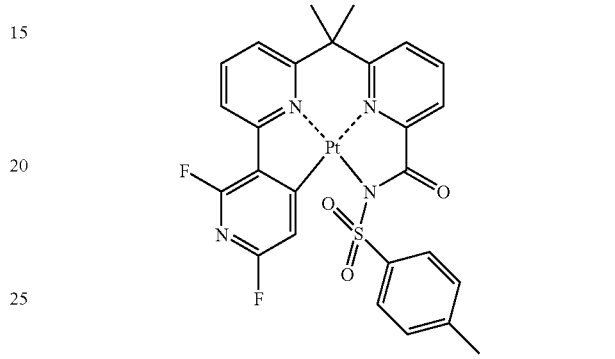
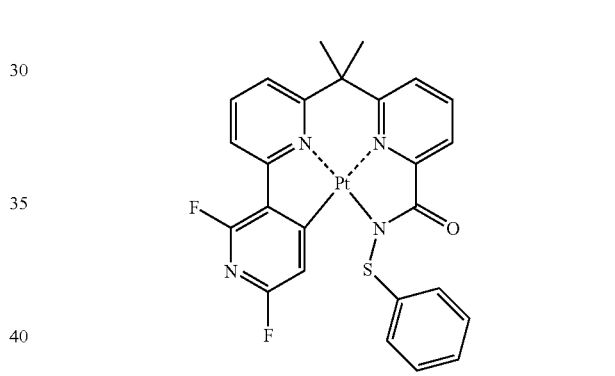
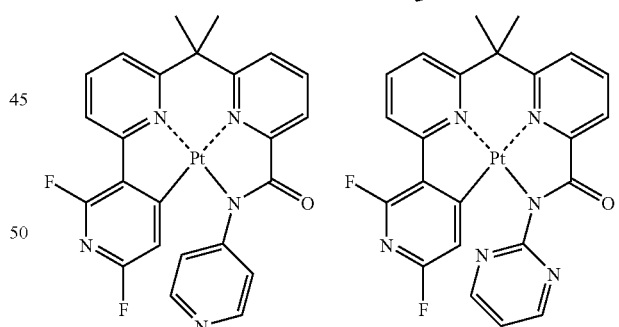
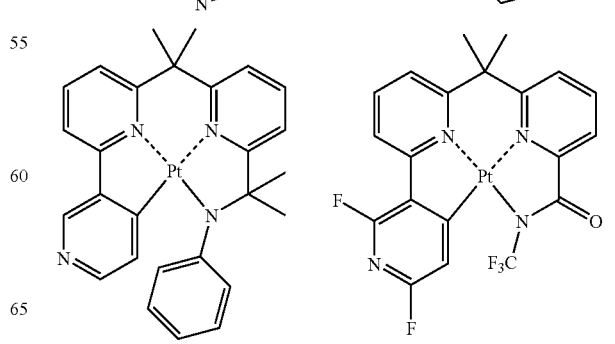

39
-continued
40
-continued
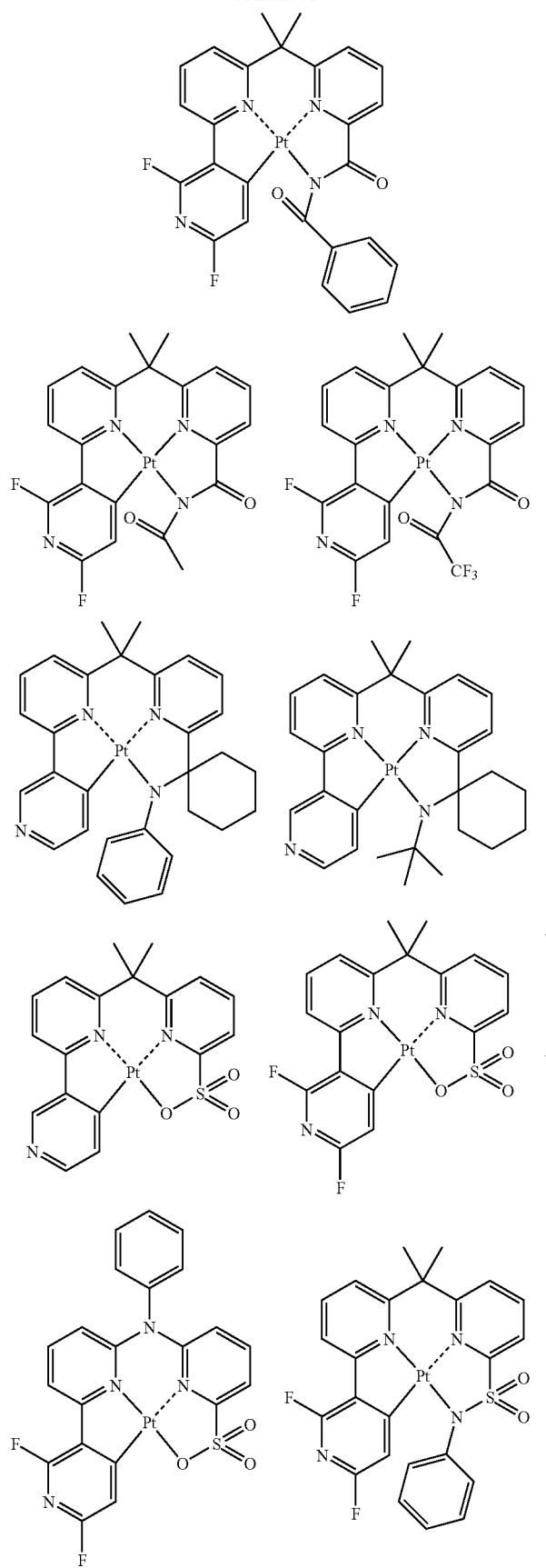
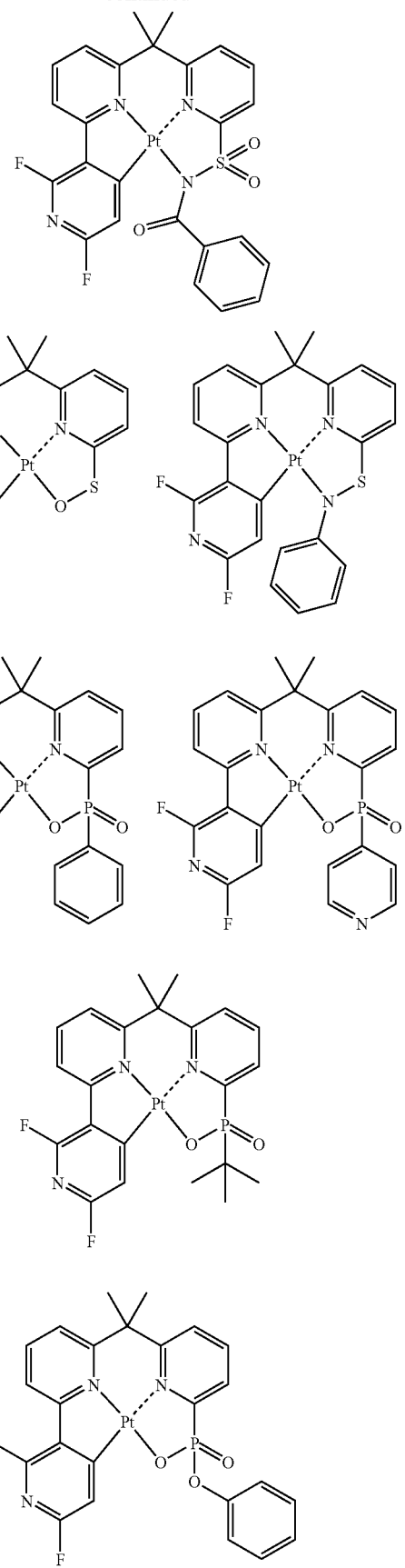

-continued
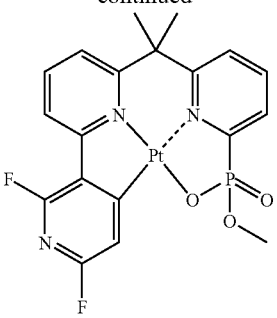
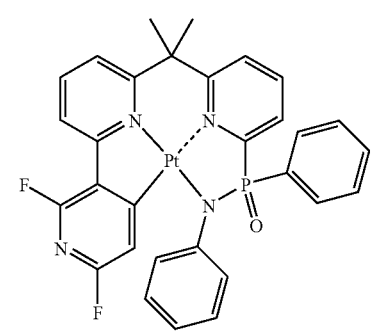
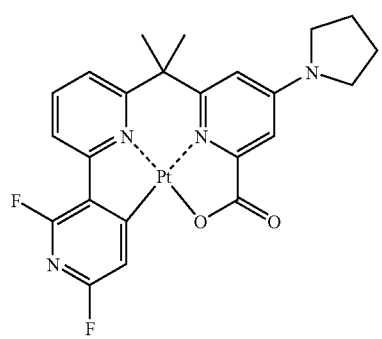
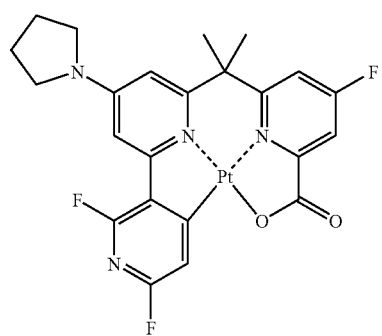
-continued
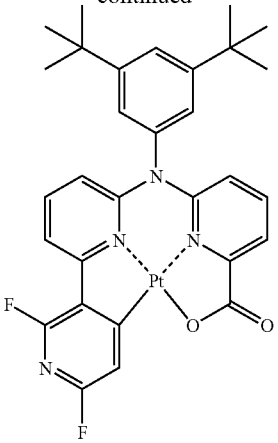
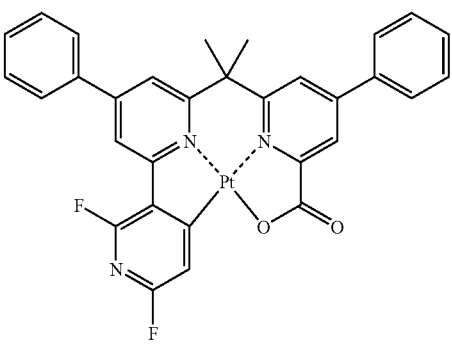
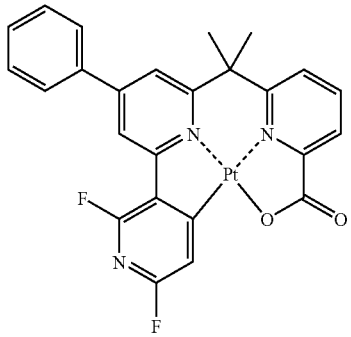
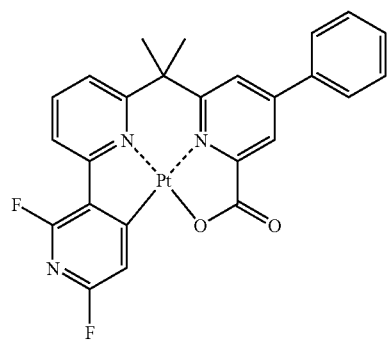

43
-continued
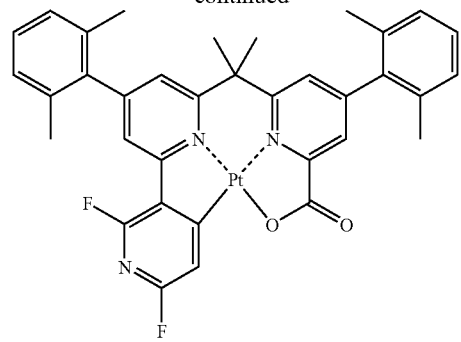
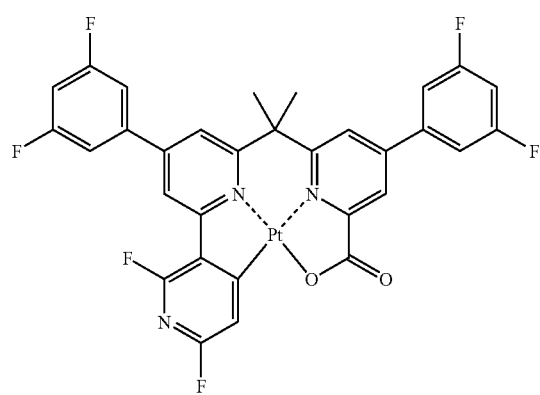
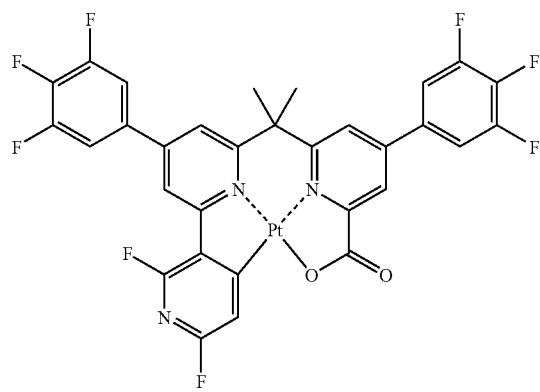
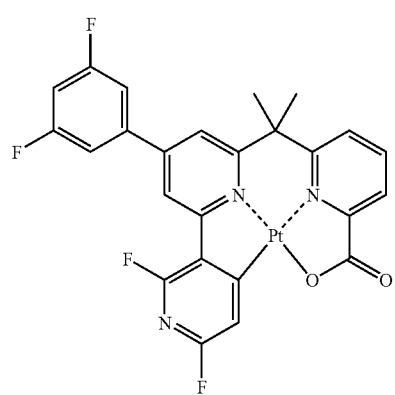
44
-continued
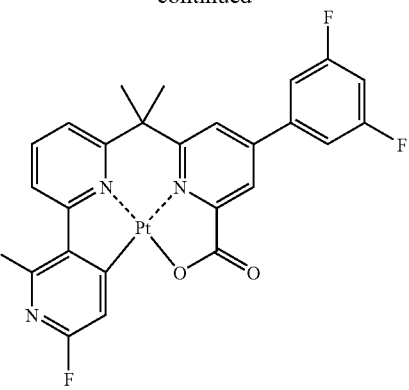
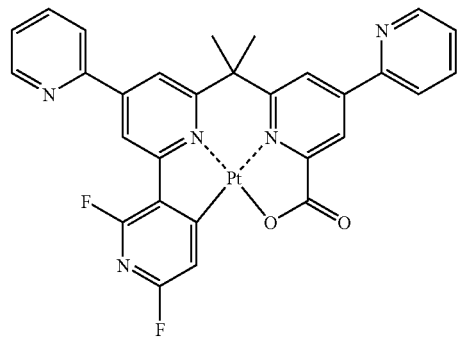
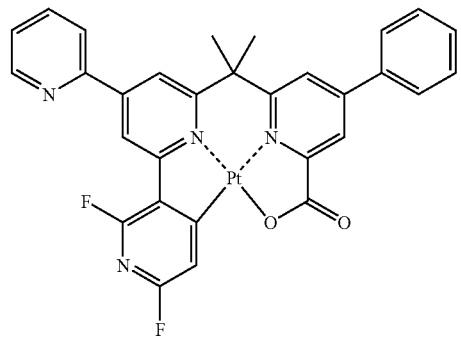
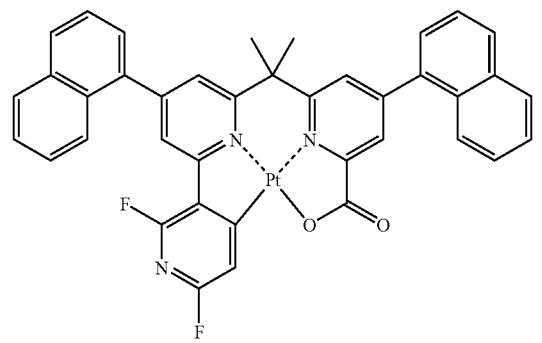
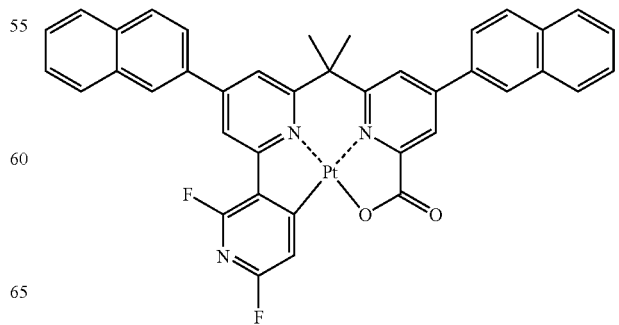

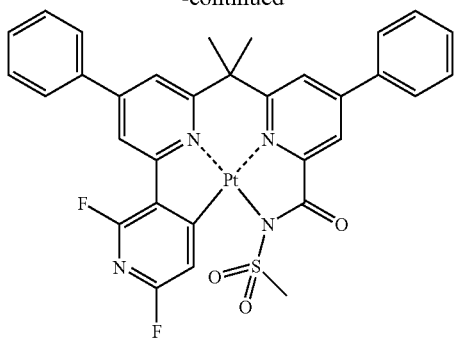

Compounds exemplified as the compound represented by the formula (I) can be prepared, for example, by the following steps.

The above-described metal complex compounds can be synthesized by various processes, for example, the processes described in G. R. Newkome et al. *Journal of Organic Chemistry,* 53, 786(1988), page 789, line 53 of left column to line 7 of right column, page 790, lines 18 to 38 of left column, and page 790, lines 19 to 30 of right column, and combinations of these processes; and the processes described in H. Lexy et al. *Chemische Berichte,* 113, 2749(1980), page 2752, lines 26 to 35.

For example, the metal complex compound can be obtained by placing, under the condition of a temperature not greater than a room temperature or under heating (in addition to ordinary heating, microwave heating is also effective), a ligand or a dissociated product thereof and a metal compound in a solvent (such as halogen-based solvent, alcohol-based solvent, ether-based solvent, ester-based solvent, ketone-based solvent, nitrile-based solvent, amide-based solvent, sulfone-based solvent, sulfoxide-based solvent, or water) or in a solventless manner in the presence of a base (various inorganic and organic bases such as sodium methoxide, t-butoxy potassium, triethylamine, and potassium carbonate) or in the absence of a base.

In the invention, the compound represented by the formula (I) may be used in combination with another platinum (Pt) complex or iridium (Ir) complex.

The another platinum complex or Ir complex may be incorporated in the layer containing the compound represented by the formula (I) or another layer, but incorporation of a phosphorescent material having a higher lowest triplet energy than that of the compound of the invention together with the compound represented by the formula (I) enables to cause emission of the light emitting material at a higher efficiency. When the compound represented by the formula (I) is used as a light emitting material, use of a platinum complex represented by the following formula (C-1) and having a higher lowest triplet energy than that of the compound represented by the formula (I) is highly effective for improving the efficiency and is therefore especially preferred.

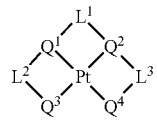

(C-1)

(wherein, $Q^1$, $Q^2$, $Q^3$, and $Q^4$ each independently represents a ligand coordinated to Pt and $L_1$, $L_2$, and $L_3$ each independently represents a single bond or a divalent linking group).

The formula (C-1) will next be described. $Q^1$, $Q^2$, $Q^3$, and $Q^4$ each may be bound to Pt through any of a covalent bond, an ionic bond, and a coordinate bond. As the atom in $Q^1$, $Q^2$, $Q^3$, and $Q^4$ that is bound to Pt, a carbon atom, a nitrogen atom, an oxygen atom, a sulfur atom, and a phosphorus atom are preferred. Preferably, at least one of the atoms in $Q^1$, $Q^2$, $Q^3$, and $Q^4$ bound to Pt is a carbon atom; more preferably, two of them are carbon atoms; and especially preferably, two of them are carbon atoms and two of them are nitrogen atoms.

$Q^1$, $Q^2$, $Q^3$, and $Q^4$ bound to Pt through a carbon atom may be either an anionic ligand or a neutral ligand. Examples of the anionic ligand include a vinyl ligand, aromatic hydrocarbon ring ligands (such as benzene ligand, naphthalene ligand, anthracene ligand, and phenanthrene ligand), and heterocyclic ligands (such as furan ligand, thiophene ligand, pyridine ligand, pyrazine ligand, pyrimidine ligand, pyridazine ligand, triazine ligand, thiazole ligand, oxazole ligand, pyrrole ligand, imidazole ligand, pyrazole ligand, and triazole ligand, and fused ring derivatives containing these ligands (such as quinoline ligand and benzothiazole ligand)). Examples of the neutral ligand include a carbene ligand.

$Q^1$, $Q^2$, $Q^3$, and $Q^4$ bound to Pt through a nitrogen atom may be either a neutral ligand or an anionic ligand. Examples of the neutral ligand include nitrogen-containing aromatic heterocyclic ligands (such as pyridine ligand, pyrazine ligand, pyrimidine ligand, pyridazine ligand, triazine ligand, imidazole ligand, pyrazole ligand, triazole ligand, oxazole ligand, and thiazole ligand, and fused ring derivatives containing these ligands (such as quinoline ligand and benzimidazole ligand)), an amine ligand, a nitrile ligand, and an imine ligand. Examples of the anionic ligand include an amino ligand, an imino ligand, and nitrogen-containing aromatic heterocyclic ligands (such as pyrrole ligand, imidazole ligand, and triazole ligand, and fused ring derivatives containing these ligands (such as indole ligand and benzimidazole ligand)).

$Q^1$, $Q^2$, $Q^3$, and $Q^4$ bound to Pt through an oxygen atom may be either a neutral ligand or an anionic ligand. Examples of the neutral ligand include an ether ligand, a ketone ligand, an ester ligand, an amide ligand, and oxygen-containing heterocyclic ligands (such as furan ligand and oxazole ligand, and fused ring derivatives containing these ligands (such as benzoxazole ligand)). Examples of the anionic ligand include an alkoxy ligand, an aryloxy ligand, a heteroaryloxy ligand, an acyloxy ligand, and a silyloxy ligand.

$Q^1$, $Q^2$, $Q^3$, and $Q^4$ bound to Pt via a sulfur atom may be either a neutral ligand or an anionic ligand. Examples of the neutral ligand include a thioether ligand, a thioketone ligand, a thioester ligand, a thioamide ligand, and sulfur-containing heterocyclic ligands (such as thiophene ligand and thiazole ligand, and fused ring derivatives containing these ligands (such as benzothiazole ligand)). Examples of the anionic ligand include an alkylmercapto ligand, an arylmercapto ligand, and a heteroarylmercapto ligand.

$Q^1$, $Q^2$, $Q^3$, and $Q^4$ bound to Pt via a phosphorus atom may be either a neutral ligand or an anionic ligand. Examples of the neutral ligand include a phosphine ligand, a phosphoric ester ligand, a phosphorous ester ligand, and phosphorus-containing heterocyclic ligands (such as phosphinine ligand). Examples of the anionic ligand include a phosphino ligand, a phosphinyl ligand, and a phosphoryl ligand.

Each of the groups represented by $Q^1$, $Q^2$, $Q^3$, and $Q^4$ may have a substituent. As the substituent, those listed in the substituent group A can be employed as needed. The substituents may be linked to each other (linking $Q^3$ and $Q^4$ yields a Pt complex with a cyclic tetradentate ligand).

The groups represented by $Q^1$, $Q^2$, $Q^3$, and $Q^4$ are each preferably an aromatic hydrocarbon ring ligand bound to Pt through a carbon atom, an aromatic heterocyclic ligand bound to Pt through a carbon atom, a nitrogen-containing aromatic heterocyclic ligand bound to Pt through a nitrogen atom, an acyloxy ligand, an alkyloxy ligand, an aryloxy ligand, a heteroaryloxy ligand, or a silyloxy ligand; more preferably an aromatic hydrocarbon ring ligand bound to Pt through a carbon atom, an aromatic heterocyclic ligand bound to Pt through a carbon atom, a nitrogen-containing aromatic heterocyclic ligand bound to Pt through a nitrogen atom, an acyloxy ligand, or an aryloxy ligand; still more preferably an aromatic hydrocarbon ring ligand bound to Pt through a carbon atom, an aromatic heterocyclic ligand bound to Pt through a carbon atom, a nitrogen-containing aromatic heterocyclic ligand bound to Pt through a nitrogen atom, or an acyloxy ligand.

Each of $L^1$, $L^2$ and $L^3$ represents a single bond or a divalent linking group. Examples of the divalent linking groups represented by $L^1$, $L^2$ and $L^3$ include alkylene groups (such as methylene, ethylene, and propylene), arylene groups (such as phenylene and naphthalenediyl), heteroarylene groups (such as pyridinediyl and thiophenediyl), imino groups (—NR—) (such as phenylimino group), an oxy group (—O—), a thio group (—S—), phosphinidene groups (—PR—) (such as phenylphosphinidene group), and silylene groups (—SiRR'—) (such as dimethylsilylene group and diphenylsilylene group), and combinations thereof. These linking groups may further have a substituent. From the standpoints of stability of the complex and emission quantum efficiency, $L^1$, $L^2$ and $L^3$ each represents preferably a single bond, an alkylene group, an arylene group, a heteroarylene group, an imino group, an oxy group, a thio group, or a silylene group, more preferably a single bond, an alkylene group, an arylene group, or an imino group, still more preferably a single bond, an alkylene group, or an arylene group, still more preferably a single bond, a methylene group, or a phenylene group, still more preferably a single bond or a di-substituted methylene group, still more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, especially preferably a single bond, a dimethylmethylene group, a diphenylmethylene group, or a cyclohexanediyl group.

The platinum complex represented by formula (C-1) is more preferably a platinum complex represented by the following formula (C-2).

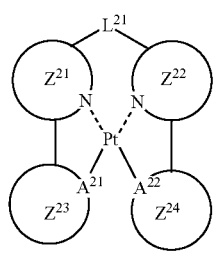

(wherein, $L^{21}$ represents a single bond or a divalent linking group; $A^{21}$ and $A^{22}$ independently represents C or N; $Z^{21}$ and $Z^{22}$ each independently represents a nitrogen-containing aromatic heterocycle, and $Z^{23}$ and $Z^{24}$ each independently represents a benzene ring or an aromatic heterocycle).

The formula (C-2) will next be described. $L^{21}$ has the same meaning as $L^1$ in the formula (C-1) and the preferred range of it is also the same.

$A^{21}$ and $A^{22}$ each independently represents a carbon atom or a nitrogen atom. It is preferred that at least one of $A^{21}$ and $A^{22}$ represents a carbon atom. From the standpoints of stability and emission quantum efficiency of the complex, it is more preferred that both of $A^{21}$ and $A^{22}$ represent carbon atoms.

$Z^{21}$ and $Z^{22}$ each independently represents a nitrogen-containing aromatic heterocycle. Examples of the nitrogen-containing aromatic heterocycle represented by $Z^{21}$ or $Z^{22}$ include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. From the standpoints of stability, emission wavelength control, and emission quantum efficiency of the complex, the ring represented by $Z^{21}$ or $Z^{22}$ is preferably a pyridine ring, a pyrazine ring, an imidazole ring, or a pyrazole ring, more preferably a pyridine ring, an imidazole ring, or a pyrazole ring, still more preferably a pyridine ring or a pyrazole ring, especially preferably a pyridine ring.

The nitrogen-containing aromatic heterocycle represented by $Z^{21}$ and $Z^{22}$ may have a substituent. As the substituent on the carbon atom, those listed in the substituent group A can be employed, while as the substituent on the nitrogen atom, those listed in the substituent group B can be employed. Preferred examples of the substituent on the carbon atom include alkyl groups, polyfluoroalkyl groups, aryl groups, aromatic heterocyclic groups, dialkylamino groups, diarylamino groups, alkoxy groups, a cyano group, and halogen atoms. The substituent is selected as needed for controlling the emission wavelength or potential, but in order to shorten the wavelength, electron donating groups, a fluorine atom, and aromatic cyclic groups are preferred. For example, an alkyl group, a dialkylamino group, an alkoxy group, a fluorine atom, an aryl group, or an aromatic heterocyclic group is selected. In order to prolong the wavelength, electron attracting groups are preferred. For example, a cyano group or a polyfluoroalkyl group is selected. The substituent on N is preferably an alkyl group, an aryl group, or an aromatic heterocyclic group. From the standpoint of the stability of the complex, an alkyl group and an aryl group are preferred. The above-described substituents may be coupled to form a fused ring. Examples of the fused ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring.

$Z^{23}$ and $Z^{24}$ each independently represents a benzene ring or an aromatic heterocycle. Examples of the nitrogen-containing aromatic heterocycle represented by $Z^{23}$ or $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring. From the standpoints of the stability, emission wavelength control, and emission quantum efficiency of the complex, the ring represented by $Z^{23}$ or $Z^{24}$ is preferably a benzene ring, a pyridine ring, a pyrazine ring, an imidazole ring, a pyrazole ring, or a thiophene ring, more preferably a benzene ring, a pyridine ring, or a pyrazole ring, still more preferably a benzene ring or a pyridine ring.

The benzene ring and nitrogen-containing aromatic heterocycle represented by $Z^{23}$ or $Z^{24}$ may have a substituent. As the substituent on the carbon atom, those listed in the substituent group A can be employed, while as the substituent on the nitrogen atom, those listed in the substituent group B can be employed. Preferred examples of the substituent on the carbon atom include alkyl groups, polyfluoroalkyl groups, aryl groups, aromatic heterocyclic groups, dialkylamino groups, diarylamino groups, alkoxy groups, a cyano group, and halogen atoms. The substituent may be selected as needed for controlling the emission wavelength or potential. In order to prolong the wavelength, electron donating groups and aromatic cyclic groups are preferred and for example, an alkyl group, a dialkylamino group, an alkoxy group, an aryl group, or an aromatic heterocyclic group is selected. In order to shorten the wavelength, electron attracting groups are preferred and for example, a fluorine group, a cyano group, or a polyfluoroalkyl group is selected. The substituent on N is preferably an alkyl group, an aryl group, or an aromatic heterocyclic group. From the standpoint of stability of the complex, an alkyl group and an aryl group are preferred. The above-described substituents may be coupled to form a fused ring. Examples of the fused ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring.

One of the more preferred modes of the platinum complex represented by the formula (C-2) is a platinum complex represented by the following formula (C-3):

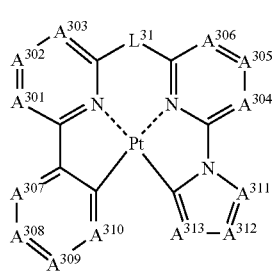

(C-3)

(wherein, $A^{301}$ to $A^{313}$ each independently represents C—R or N in which R represents a hydrogen atom or a substituent, and $L^{31}$ represents a single bond or a divalent linking group).

The formula (C-3) will next be described. $L^{31}$ has the same meaning as $L^{21}$ in the formula (C-2) and the preferred range of it is also the same. $A^{301}$ to $A^{306}$ each independently represents CR— or N in which R represents a hydrogen atom or a substituent. Examples of the substituent represented by R include those listed in the substituent group A.

$A^{301}$ to $A^{306}$ are each preferably C—R and Rs may be coupled to each other to form a ring. When $A^{301}$ to $A^{306}$ each represents C—R, the R of $A^{302}$ and $A^{305}$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, especially preferably a hydrogen atom or a fluorine group. The R of $A^{301}$, $A^{303}$, $A^{304}$, and $A^{306}$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, especially preferably a hydrogen atom. $A^{307}$, $A^{308}$, $A^{309}$, and $A^{310}$ each independently represents C—R or N in which R represents a hydrogen atom or a substituent. Examples of the substituent represented by R include those listed in the substituent group A. When $A^{307}$, $A^{308}$, $A^{309}$, and $A^{310}$ each represents C—R, R is preferably a hydrogen atom, an alkyl group, a polyfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a polyfluoroalkyl group, an aryl group, a dialkylamino group, a cyano group, or a fluorine atom, still more preferably a hydrogen atom, an alkyl group, a trifluoromethyl group, or a fluorine atom. If possible, the substituents may be coupled to each other to form a fused ring structure. When the emission wavelength is shifted to the short wavelength side, $A^{308}$ is preferably an N atom.

When $A^{307}$ to $A^{310}$ are selected as described above, examples of a 6-membered ring formed of two carbon atoms, $A^{307}$, $A^{308}$, $A^{309}$, and $A^{310}$ include a benzene ring, a pyridine ring, a pyrazine ring, a pyrimidine ring, a pyridazine ring, and a triazine ring, more preferably a benzene ring, a pyridine ring, a pyrazine ring, a pyrimidine ring, and a pyridazine ring, especially preferably a benzene ring and a pyridine ring. It is advantageous that the 6-membered ring is a pyridine ring, a pyrazine ring, a pyrimidine ring, or a pyridazine ring (especially preferably, a pyridine ring) because compared with the case where the 6-membered ring is a benzene ring, improvement in the acidity of the hydrogen atom present at a metal-carbon bond forming position facilitates formation of a metal complex.

$A^{311}$, $A^{312}$, and $A^{313}$ each independently represents C—R or N in which R represents a hydrogen atom or a substituent. Examples of the substituent represented by R include those listed in the substituent group A. When $A^{311}$, $A^{312}$, and $A^{313}$ each represents C—R, R is preferably a hydrogen atom, an alkyl group, a polyfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a polyfluoroalkyl group, an aryl group, a dialkylamino group, a cyano group, or a fluorine atom, still more preferably a hydrogen atom, an alkyl group, a trifluoromethyl group, or a fluorine atom. If possible, the substituents may be coupled to each other to form a fused ring structure. Preferably at least one of $A^{311}$, $A^{312}$, and $A^{313}$ represents N and especially preferably $A^{311}$ represents N.

One of the more preferred modes of the platinum complex represented by the formula (C-2) is a platinum complex represented by the following formula (C-4):

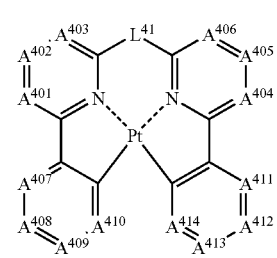

(C-4)

(in the formula (C-4), $A^{401}$ to $A^{414}$ each independently represents C—R or N in which R represents a hydrogen atom or a substituent, and $L^{41}$ represents a single bond or a divalent linking group).

The formula (C-4) will next be described.

$A^{401}$ to $A^{414}$ each independently represents C—R or N in which R represents a hydrogen atom or a substituent. $A^{401}$ to $A^{406}$ and $L^{41}$ have the same meanings as $A^{301}$ to $A^{306}$ and $L^{31}$ in the formula (C-3) and the preferred ranges of them are also the same.

With respect to $A^{407}$ to $A^{414}$, the number of N (nitrogen atoms) in $A^{407}$ to $A^{410}$ and $A^{411}$ to $A^{414}$ is preferably from 0 to 2, more preferably from 0 to 1. When the emission wavelength is shifted to the short wavelength side, preferably at least one of $A^{408}$ and $A^{412}$ is an N atom and more preferably both of $A^{408}$ and $A^{412}$ are N atoms.

When $A^{407}$ to $A^{414}$ each represents C—R, the R of $A^{408}$ and $A^{412}$ is preferably a hydrogen atom, an alkyl group, a polyfluoroalkyl group, an aryl group, an amino group, an alkoxy group, an aryloxy group, a fluorine group, or a cyano group, more preferably a hydrogen atom, a polyfluoroalkyl group, an alkyl group, an aryl group, a fluorine atom, or a cyano group, especially preferably a hydrogen atom, a phenyl group, a polyfluoroalkyl group, or a cyano group. The R of $A^{407}$, $A^{409}$, $A^{411}$, and $A^{413}$ is preferably a hydrogen atom, an alkyl group, a polyfluoroalkyl group, an aryl group, an amino group, an alkoxy group, an aryloxy group, a fluorine group, or a cyano group, more preferably a hydrogen atom, a polyfluoroalkyl group, a fluorine group, or a cyano group, especially preferably a hydrogen atom, a phenyl group, or a fluorine group. The R of $A^{410}$ and $A^{414}$ is preferably a hydrogen atom or a fluorine group, more preferably a hydrogen atom. When any one of $A^{407}$ to $A^{409}$ and $A^{411}$ to $A^{413}$ represents C—R, Rs may be coupled to each other to form a ring.

One of the more preferred modes of the platinum complex represented by the formula (C-2) is a platinum complex represented by the following formula (C-5):

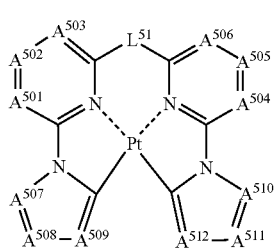

(C-5)

(in the formula (C-5), $A^{501}$ to $A^{512}$ each independently represents C—R or N in which R represents a hydrogen atom or a substituent, and $L^{51}$ represents a single bond or a divalent linking group).

The formula (C-5) will next be described. $A^{501}$ to $A^{506}$ and $L^{51}$ have the same meanings as $A^{301}$ to $A^{306}$ and $L^{31}$ in the formula (C-3) and the preferred ranges of them are also the same.

$A^{507}$, $A^{508}$, and $A^{509}$ and $A^{510}$, $A^{511}$, and $A^{512}$ have the same meanings as $A^{311}$, $A^{312}$, and $A^{313}$ in the formula (C-3), respectively, and the preferred ranges of them are also the same.

Another preferred mode of the platinum complex represented by the formula (C-1) is a platinum complex represented by the following formula (C-6):

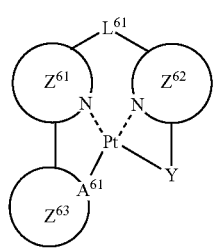

(C-6)

(wherein, $L^{61}$ represents a single bond or a divalent linking group, $A^{61}$s each independently represents C or N, $Z^{61}$ and $Z^{62}$ each independently represents a nitrogen-containing aromatic heterocycle, $Z^{63}$s each independently represents a benzene ring or an aromatic heterocycle, and Y represents an anionic non-cyclic ligand bound to Pt).

The formula (C-6) will next be described. $L^{61}$ has the same meaning as $L^1$ in the formula (C-1) and the preferred range of it is also the same.

$A^{61}$ represents C or N. From the standpoints of the stability and emission quantum efficiency of the complex, $A^{61}$ is preferably C.

$Z^{61}$ and $Z^{62}$ have the same meanings as $Z^{21}$ and $Z^{22}$ in the formula (C-2), respectively and the preferred ranges of them are also the same. $Z^{63}$ has the same meaning as $Z^{23}$ in the formula (C-2) and the preferred range of it is also the same.

Y represents an anionic non-cyclic ligand bound to Pt. The term "non-cyclic ligand" means a ligand whose atom bound to Pt does not form a ring. The atom bound to Pt in Y is preferably a carbon atom, a nitrogen atom, an oxygen atom, or a sulfur atom, more preferably a nitrogen atom or an oxygen atom, most preferably an oxygen atom. Y bound to Pt through a carbon atom is, for example, a vinyl ligand. Y bound to Pt through a nitrogen atom is, for example, an amino ligand or imino ligand. Y bound to Pt through an oxygen atom is, for example, an alkoxy ligand, an aryloxy ligand, a heteroaryloxy ligand, an acyloxy ligand, a silyloxy ligand, a carboxyl ligand, a phosphoric acid ligand, or a sulfonic acid ligand. Y bound to Pt through a sulfur atom is, for example, an alkylmercapto ligand, an arylmercapto ligand, a heteroarylmercapto ligand, or a thiocarboxylic acid ligand.

The ligand represented by Y may have a substituent and as the substituent, those listed in the substituent group A can be employed. In addition, the substituents may be coupled to each other.

The ligand represented by Y is preferably a ligand bound to Pt through an oxygen atom, more preferably an acyloxy ligand, an alkyloxy ligand, an aryloxy ligand, a heteroaryloxy ligand, or a silyloxy ligand, more preferably an acyloxy ligand.

One of the more preferred modes of the platinum complex represented by the formula (C-6) is a platinum complex represented by the following formula (C-7):

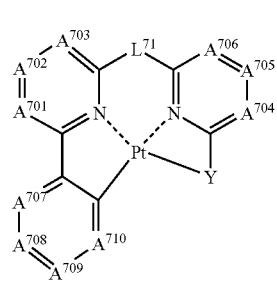

(C-7)

(wherein, $A^{701}$ to $A^{710}$ each independently represents C—R or N in which R represents a hydrogen atom or a substituent, $L^{71}$ represents a single bond or a divalent linking group, and Y represents an anionic non-cyclic ligand bound to Pt).

The formula (C-7) will next be described. $L^{71}$ has the same meaning as $L^{61}$ in the formula (C-6) and the preferred range of it is also the same. $A^{701}$ to $A^{710}$ have the same meanings as $A^{301}$ to $A^{310}$ in the formula (C-3) and the preferred ranges of them are also the same. Y has the same meaning as that in the formula (C-6) and the preferred range of it is also the same.

Specific examples of the platinum complex represented by the formula (C-1) include the compounds described in [0143]

to [0152], [0157] to [0158], and [0162] to [0168] in Japanese Patent Laid-Open No. 2005-310733, the compounds described in [0065] to [0083] in Japanese Patent Laid-Open No. 2006-256999, the compounds described in [0065] to [0090] in Japanese Patent Laid-Open No. 2006-93542, the compounds described in [0063] to [0071] in Japanese Patent Laid-Open No. 2007-73891, the compounds described in [0079] to [0083] in Japanese Patent Laid-Open No. 2007-324309, the compounds described in [0065] to [0090] in Japanese Patent Laid-Open No. 2006-93542, the compounds described in [0055] to [0071] in Japanese Patent Laid-Open No. 2007-96255, and the compounds described in [0043] to [0046] in Japanese Patent Laid-Open No. 2006-313796. Additional examples include platinum complexes exemplified below.

1-1

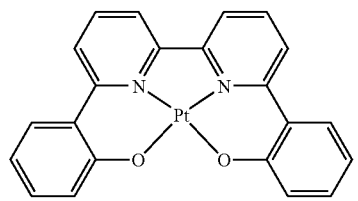

1-2

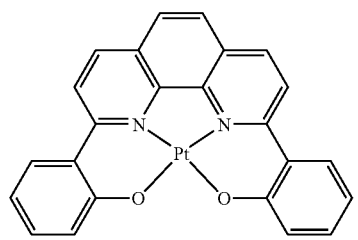

1-3

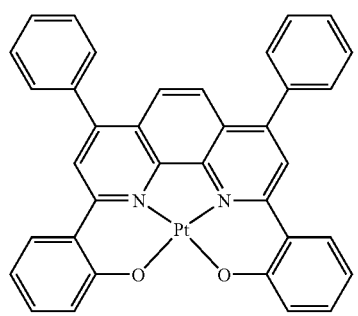

2-1

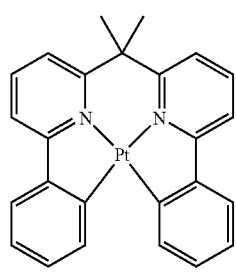

-continued 2-2

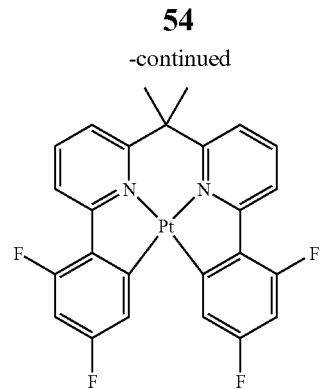

2-3

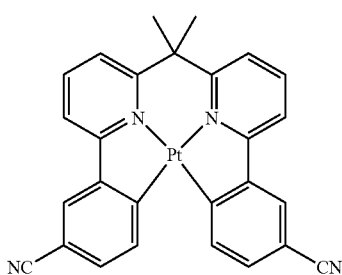

2-4

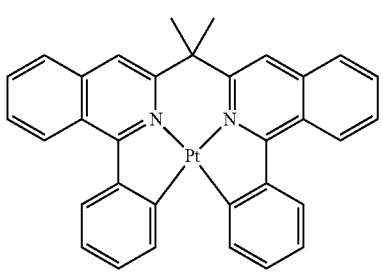

2-5

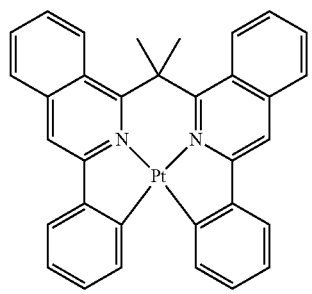

2-6

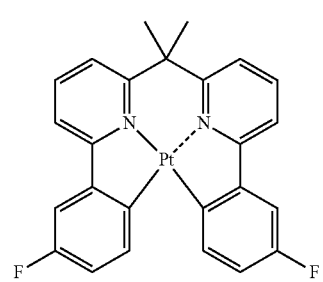

2-7
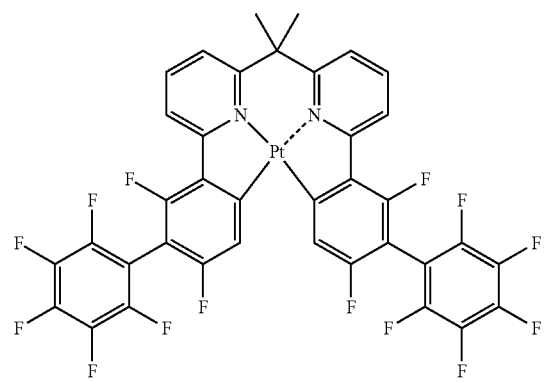
2-8
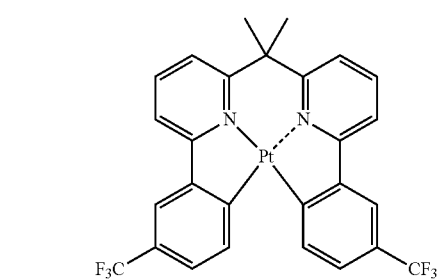
2-9
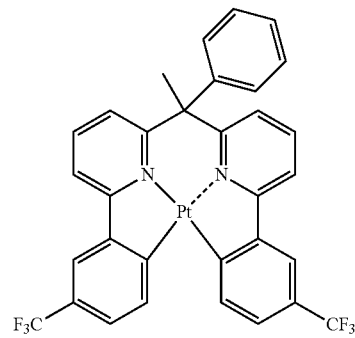
2-10
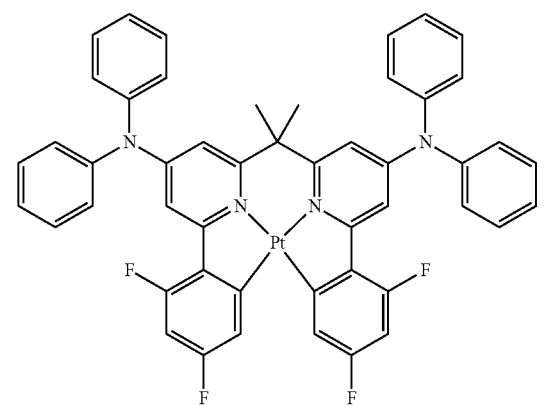
2-11
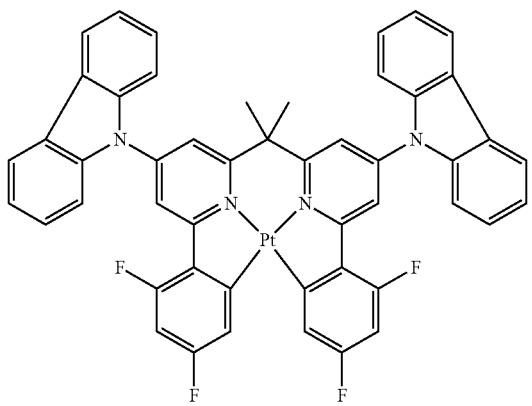
2-12
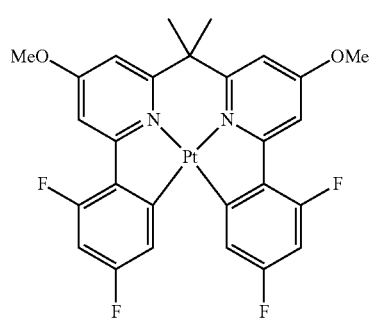
2-13
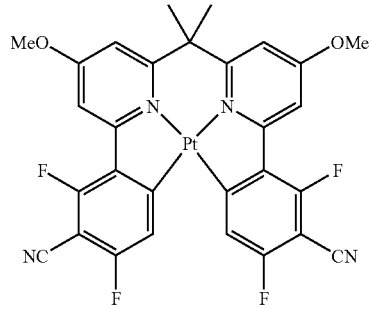
3-1
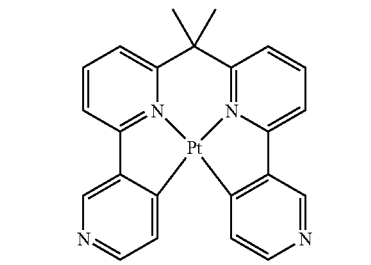
3-2
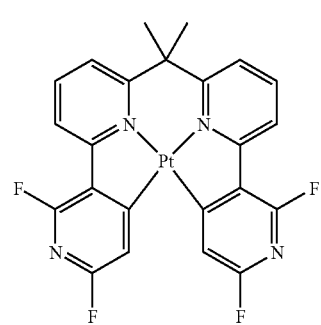

-continued
3-3
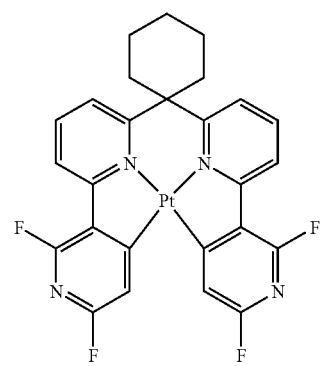
3-4
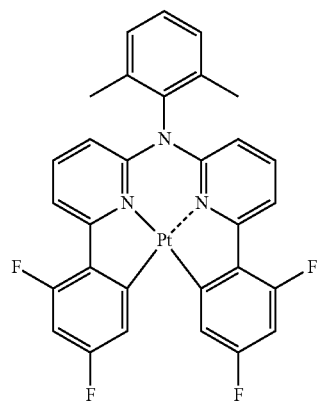
3-5
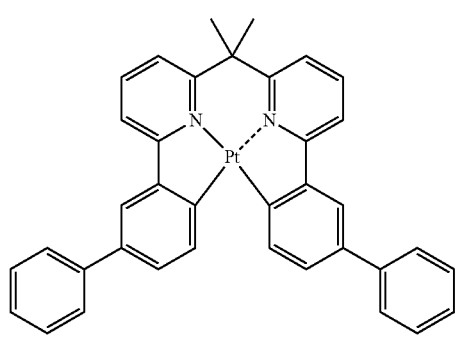
4-1
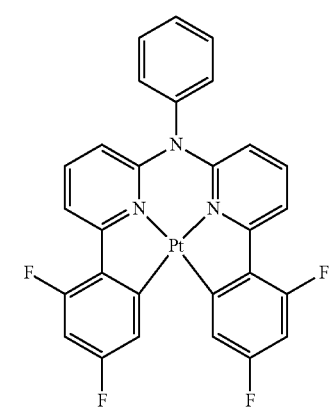
-continued
4-2
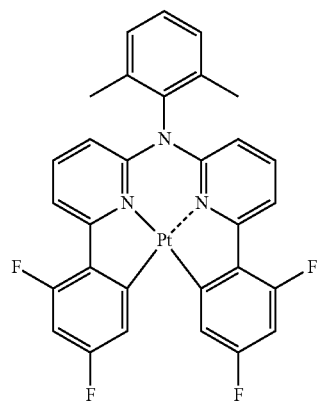
4-3
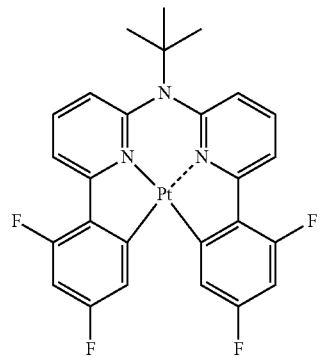
4-4
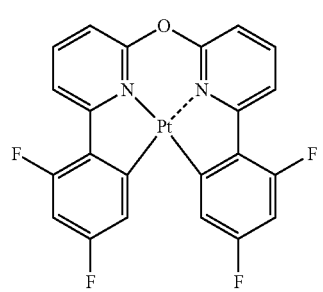
4-5

-continued
5-1
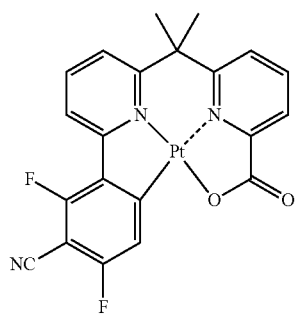
5-2
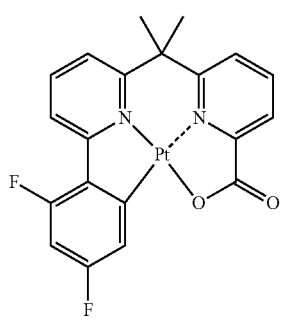
5-3
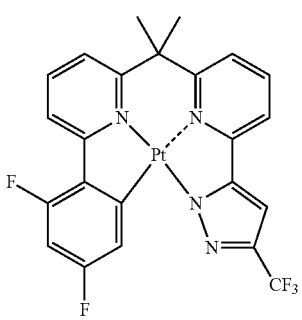
5-4
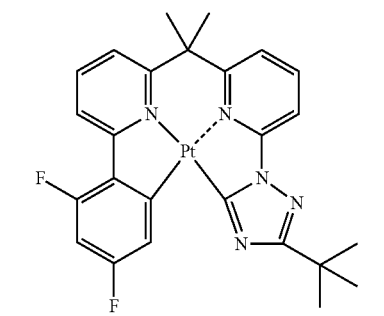
6-1
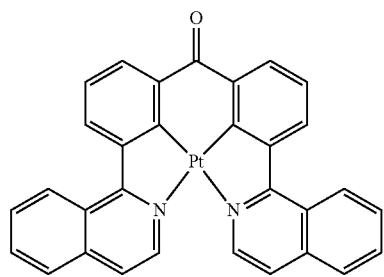
-continued
6-2
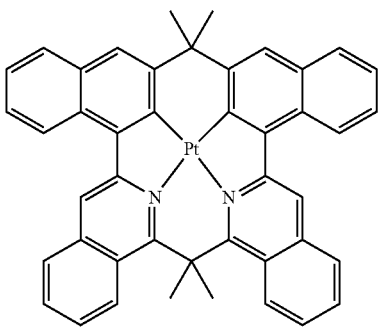
6-3
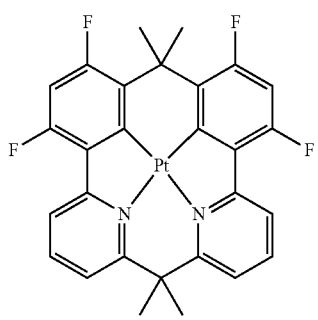
6-4
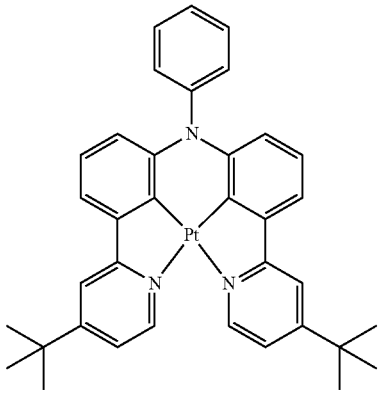
6-6
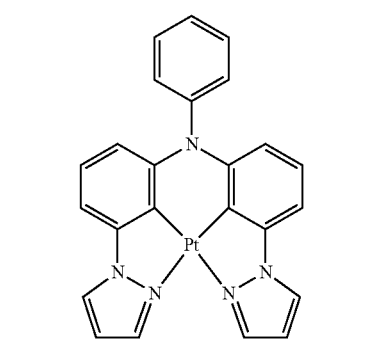

7-1 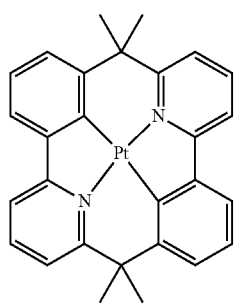
7-2 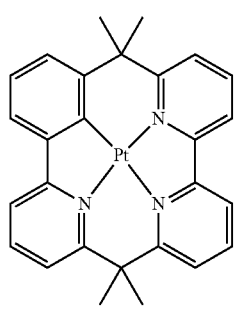
7-3 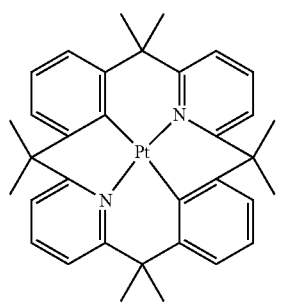
7-4 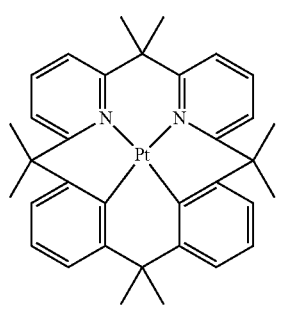
7-5 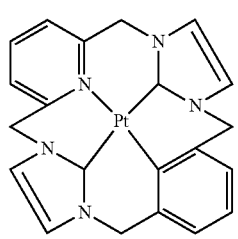
8-1 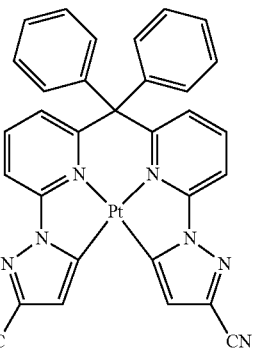
8-2 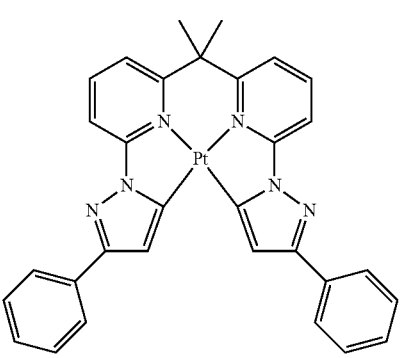
8-3 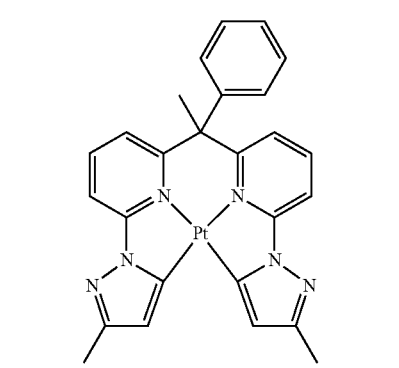
8-4 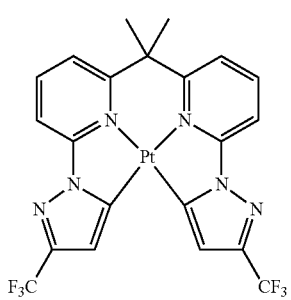

-continued
8-5
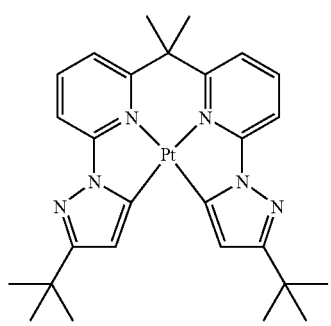
8-6
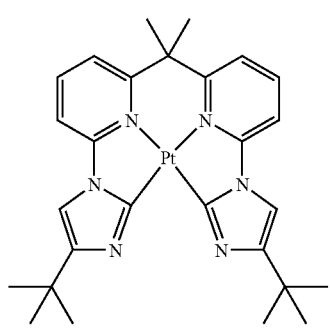
8-8
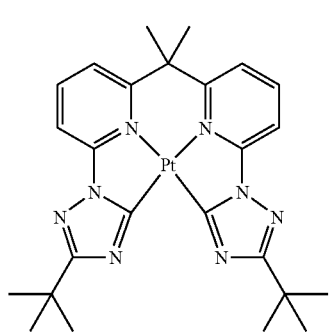
8-9
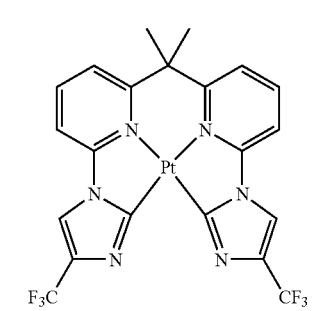
8-10
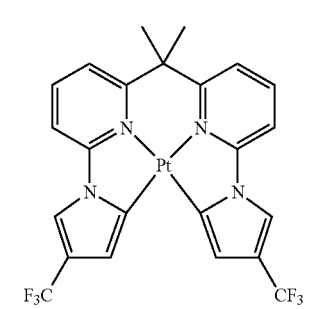
-continued
8-11
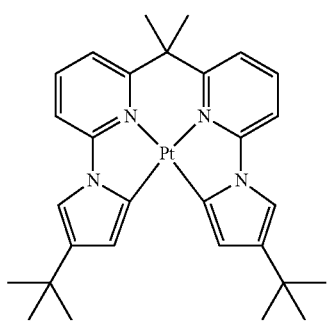
9-1
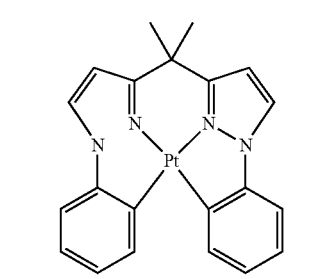
9-2
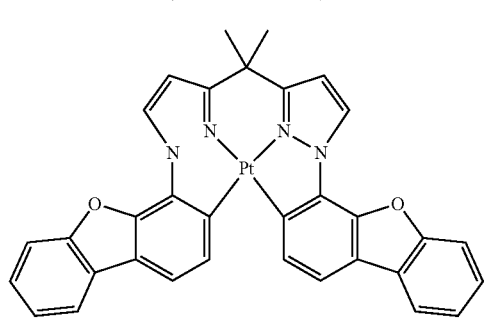
9-3
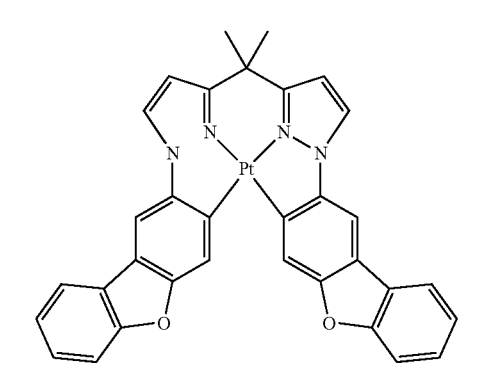
9-4
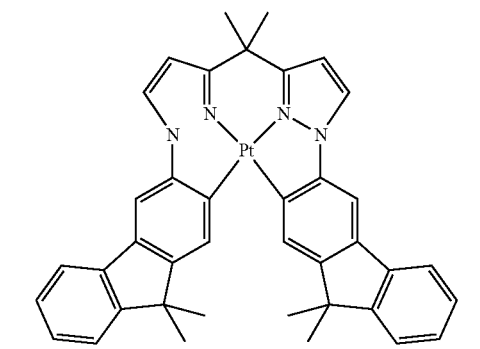

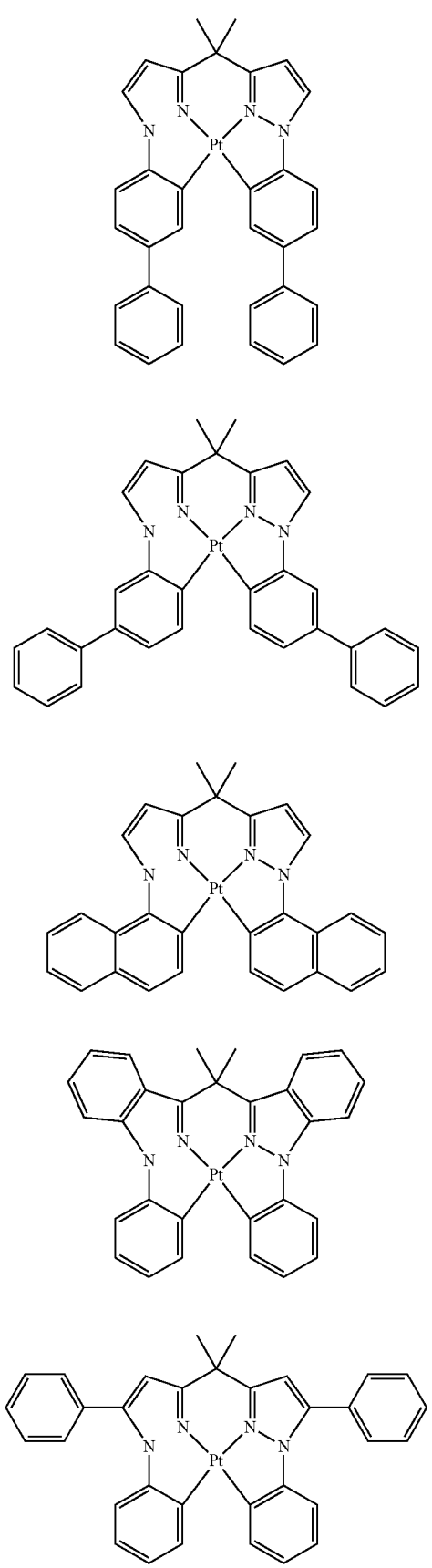
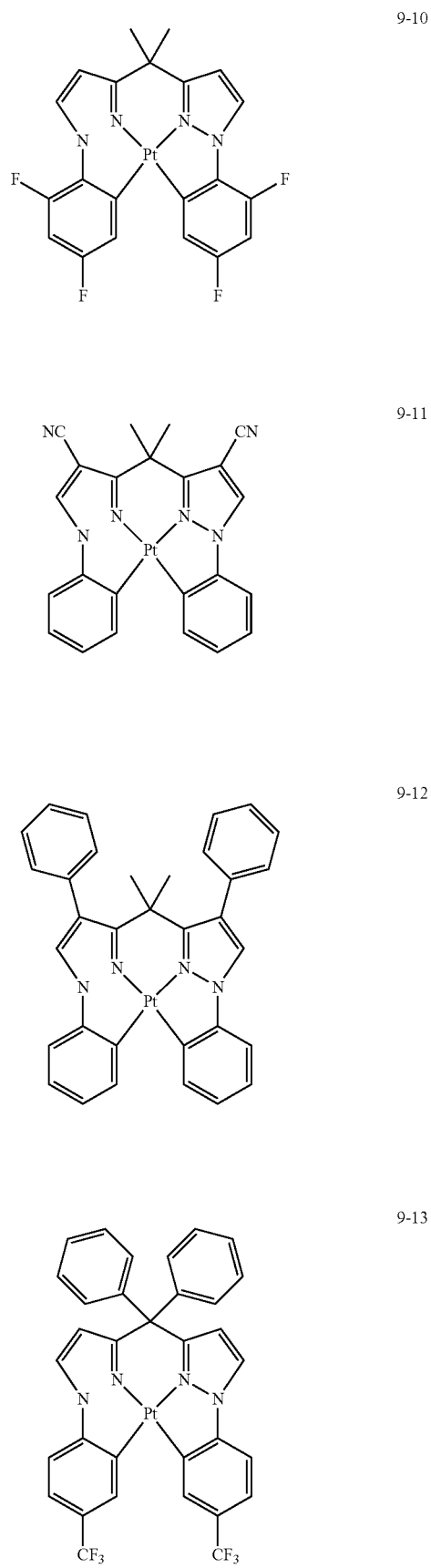

9-14

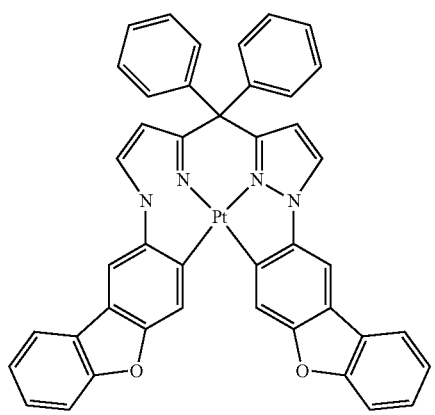

9-15

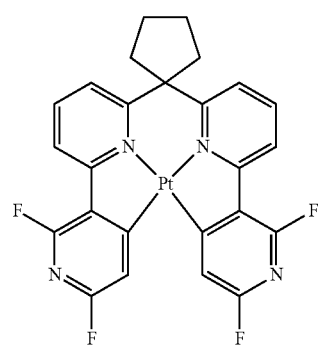

9-16

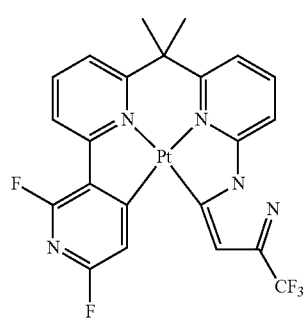

9-17

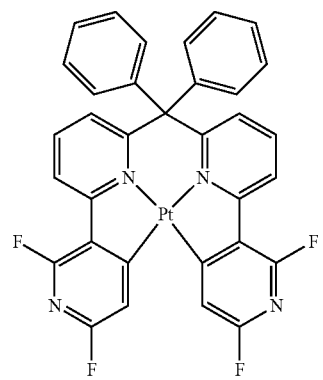

9-18

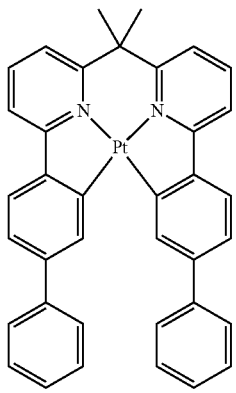

The platinum complex compounds represented by the formula (C-1) can be synthesized by various processes, for example, the processes described in G. R. Newkome et al. *Journal of Organic Chemistry*, 53, 786, (1988), page 789, line 53 of left column to line 7 of right column, page 790, lines 18 to 38 of left column, and page 790, lines 19 to 30 of right column, and combinations of these processes; and the processes described in H. Lexy et al. *Chemische Berichte*, 113, 2749, (1980), page 2752, lines 26 to 35.

For example, they can be obtained by placing, under the condition of a temperature not greater than a room temperature or under heating (in addition to ordinary heating, microwave heating is also effective), a ligand or a dissociated product thereof and a metal compound in a solvent (such as halogen-based solvent, alcohol-based solvent, ether-based solvent, ester-based solvent, ketone-based solvent, nitrile-based solvent, amide-based solvent, sulfone-based solvent, sulfoxide-based solvent, or water) or in a solventless manner in the presence of a base (examples include various inorganic and organic bases such as sodium methoxide, t-butoxy potassium, triethylamine, and potassium carbonate) or in the absence of a base.

When in the invention, the compound represented by the formula (C-1) is contained in the light emitting layer, its content in the light emitting layer is preferably from 1 to 30 mass %, more preferably from 3 to 25 mass %, still more preferably from 5 to 20 mass %.

In the invention, the iridium (Ir) complex to be used in combination is preferably a compound represented by the following formula (PQ-1).

The compound represented by the formula (PQ-1) will next be described.

(PQ-1)

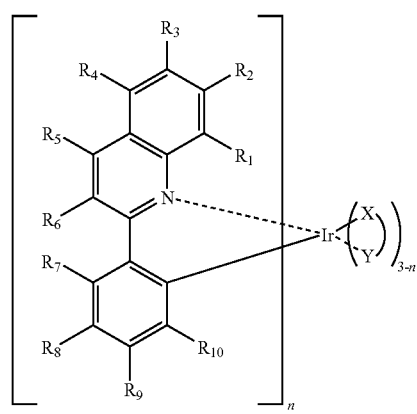

(in the formula PQ-1, $R_1$ to $R_{10}$ each represents a hydrogen atom or a substituent with the proviso that the substituents may be coupled to each other to form a ring, X—Y represents a monoanionic bidentate ligand, and n stands for an integer from 1 to 3).

Examples of the substituent represented by $R_1$ to $R_{10}$ include those listed in the substituent group A. $R_1$ to $R_{10}$ are each preferably a hydrogen atom, an alkyl group, an aryl group, an amino group, an alkoxy group, an aryloxy group, a heterocyclic oxy group, a cyano group, a heterocyclic group, a silyl group, a silyloxy group, or a fluoro group; more preferably, a hydrogen atom, an alkyl group, an aryl group, an amino group, an alkoxy group, a cyano group, a silyl group, or a fluoro group; still more preferably a hydrogen atom, an alkyl group, or an aryl group, still more preferably a hydrogen atom, a methyl group, an ethyl group, an isopropyl group, a t-butyl group, a neopentyl group, an isobutyl group, a phenyl group, a naphthyl group, a phenanthryl group, or a tolyl group, still more preferably a hydrogen atom, a methyl group, or a phenyl group. The substituents may be coupled to each other to form a ring.

n stands for preferably 2 or 3, more preferably 2.

(X—Y) represents a monoanionic bidentate ligand. It is presumed that this ligand does not directly contribute to emission properties but can control emission properties of a molecule. The "3–n" may be 0, 1, or 2. The monoanionic bidentate ligands usable in the light emitting material can be selected from those known in the art. For example, monoanionic bidentate ligands are described in Lamansky, et al., PCT application WO02/15645, page 89-90, but the present invention is not limited to them. Preferred monoanionic bidentate ligands include acetylacetonate (acac) and picolinate (pic), and derivatives thereof. In the invention, acetylacetonate is preferred as the monoanionic bidentate ligand from the standpoints of stability of the complex and high emission quantum efficiency.

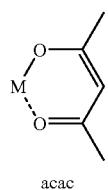

acac

The compound represented by the formula (PQ-1) is preferably a compound represented by the following formula (PQ-2).

(PQ-2)

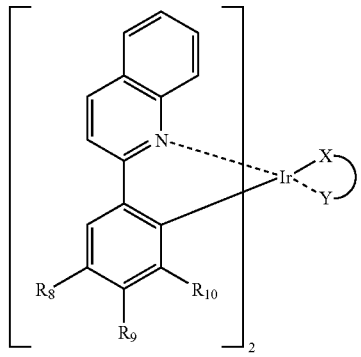

(in the formula (PQ-2), $R^8$ to $R^{10}$ each represents a hydrogen atom or a substituent, with the proviso that the substituents may be coupled to each other to form a ring, and X—Y represents a monoanionic bidentate ligand).

$R^8$ to $R^{10}$ and X—Y have the same meanings as $R^8$ to $R^{10}$ and X—Y in the formula (PQ-1), respectively and the preferred ranges of them are also the same.

The following are specific examples of the compound represented by the formula (PQ-1) but the invention is not limited to them.

FR-1

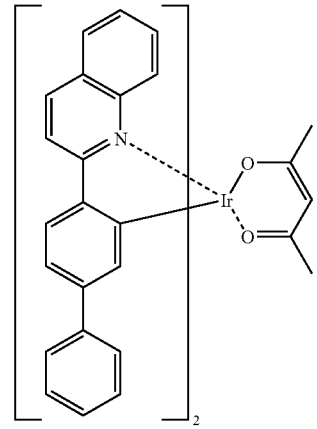

FR-2

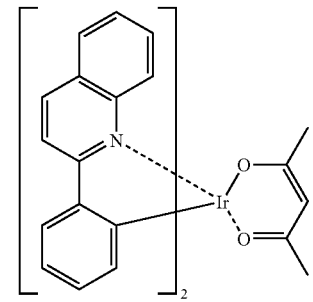

FR-3

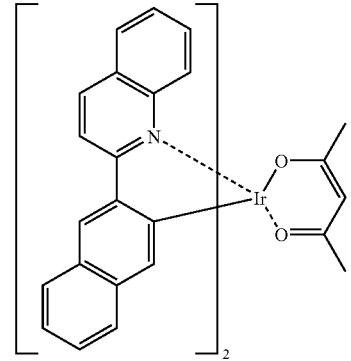

FR-4

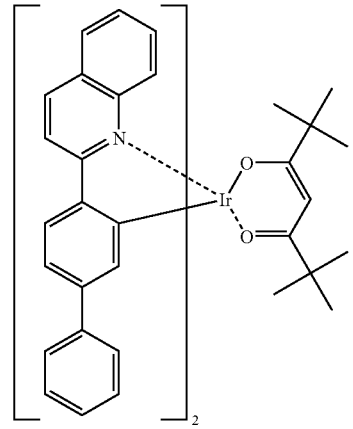

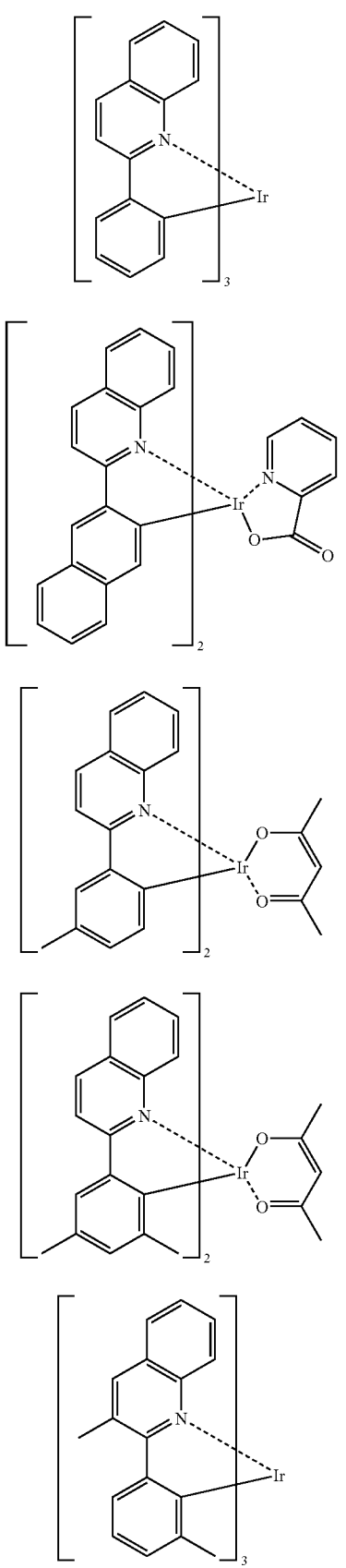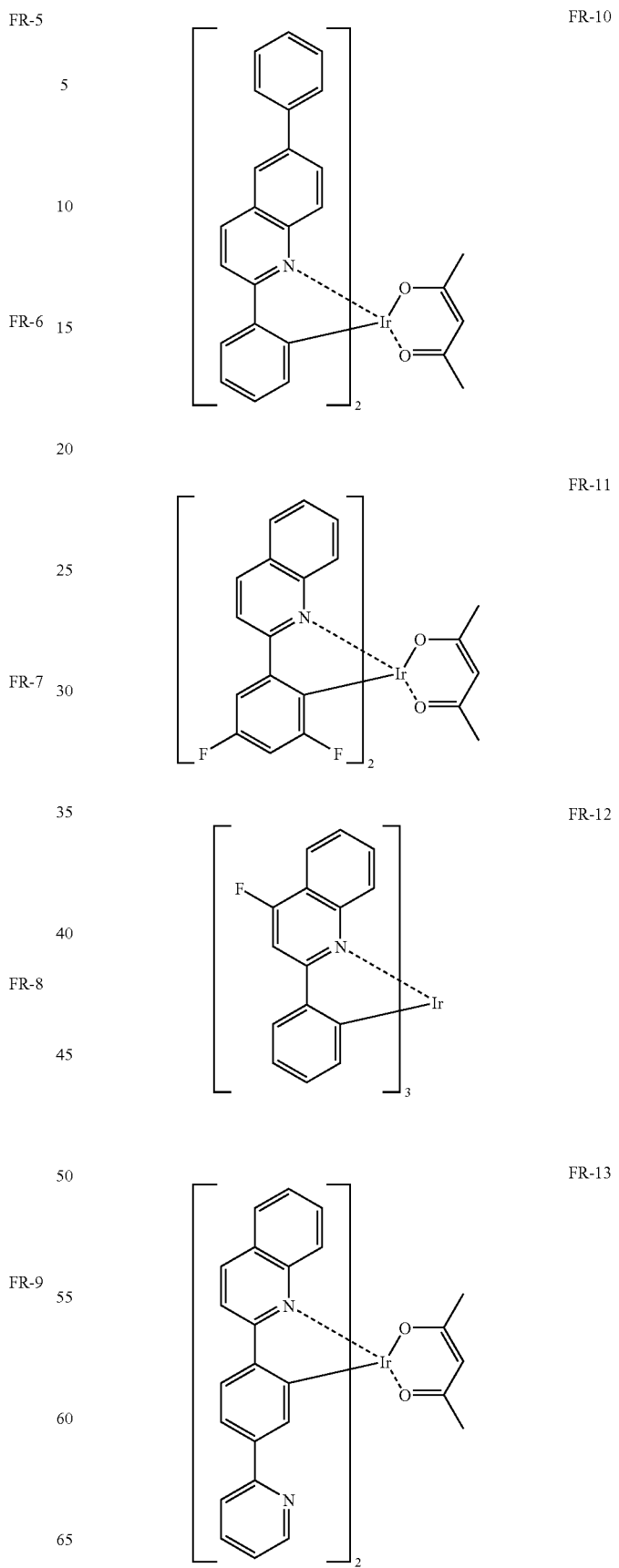

FR-14
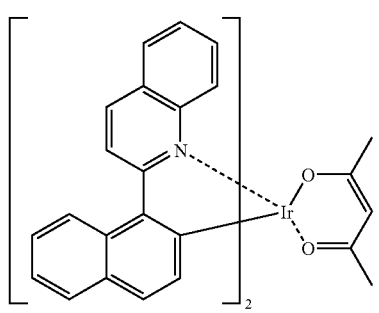
FR-15
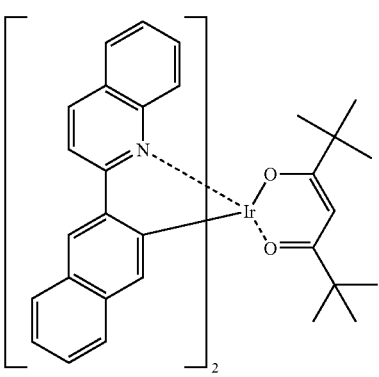
FR-16
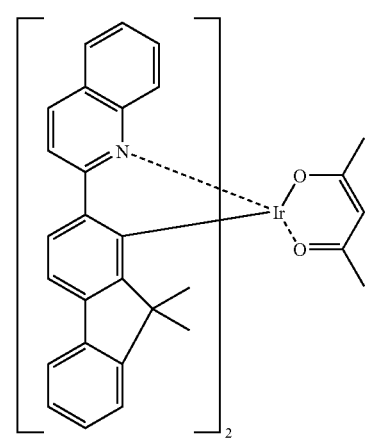
FR-17
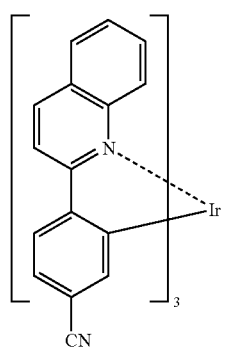
FR-18
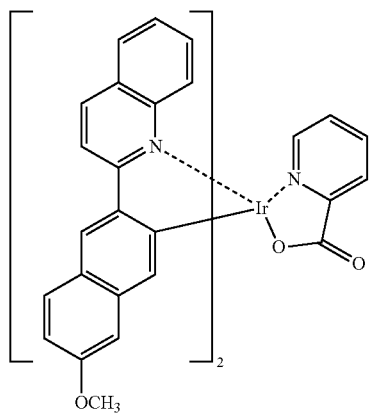
FR-19
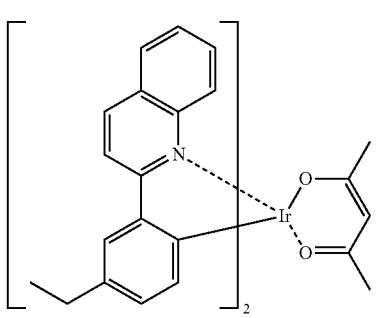
FR-20
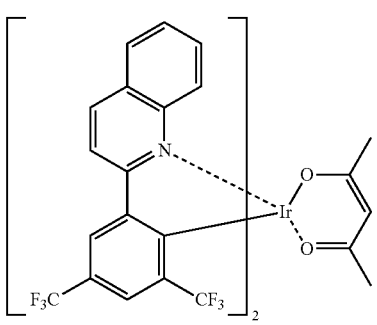
FR-21
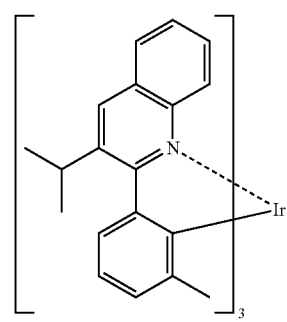

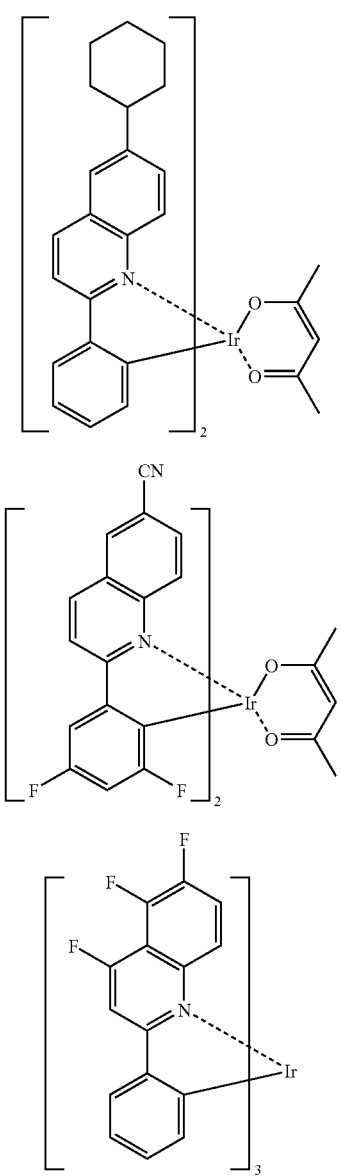

The compounds exemplified as the compound represented by the formula (PQ-1) can be synthesized by various processes as described in, for example, Japanese Patent No. 3929632. For example, FR-2 can be synthesized by using 2-phenylquinoline as a starting material in accordance with the process described in Japanese Patent No. 3929632, p18, lines 2 to 13. FR-3 can be synthesized by using 2-(2-naphthyl)quinoline as a starting material in accordance with the process described in Japanese Patent No. 3929632, p18, lines 14 to p19, line 8.

In the invention, when the compound represented by the formula (PQ-1) is incorporated in the light emitting layer, the content of the compound in the light emitting layer is preferably from 0.1 to 30 mass %, more preferably from 2 to 20 mass %, still more preferably from 5 to 15 mass %.

[Organic Electroluminescent Device]

The device of the invention will next be described in detail.

The organic electroluminescent device of the invention has a light emitting layer between a pair of electrodes and it has a layer containing the compound represented by the formula (I).

In the organic electroluminescent device of the invention, the light emitting layer and the layer containing the compound represented by the formula (I) are organic layers. The device may contain a plurality of organic layers further.

It is preferred from the property of the electroluminescent device, at least one of the anode and cathode is transparent or semi-transparent.

Although no particular limitation is imposed on the organic layers, the organic layers may have, in addition to the light emitting layer, a hole injection layer, a hole transport layer, an electron injection layer, an electron transport layer, a hole blocking layer, an electron blocking layer, an exciton blocking layer, and a protective layer. These layers each may have another function in combination.

In the invention, the organic layers are preferably stacked in the order of a hole transport layer, a light emitting layer, and an electron transport layer from the anode side. Further, the device has a charge blocking layer or the like between the hole transport layer and the light emitting layer, or between the light emitting layer and the electron transport layer. The device has, on the other hand, may have a hole injection layer between the anode and the hole transport layer. It may have between the cathode and the electron transport layer, an electron injection layer. Each layer may be composed of a plurality of layers.

FIG. 1 illustrates one example of the constitution of the organic electroluminescent device of the invention. An organic electroluminescent device 10 of the invention illustrated in FIG. 1 has a light emitting layer 6 between an anode 3 and a cathode 9 on a supporting substrate 2. Described specifically, between the anode 3 and the cathode 9, a hole injection layer 4, a hole transport layer 5, the light emitting layer 6, a hole blocking layer 7, and an electron transport layer 8 are stacked one after another in the order of mention.

The members constituting the electroluminescent device of the invention will next be described in detail.

<Substrate>

The substrate to be used in the invention is preferably one which does not scatter or attenuate light emitted from the organic layer. Specific examples include inorganic materials such as zirconia-stabilized yttrium (YSZ) and glass; and organic materials, e.g., polyesters such as polyethylene terephthalate, polybutylene phthalate, and polyethylene naphthalate, polystyrene, polycarbonate, polyethersulfone, polyarylate, polyimide, polycycloolefin, norbornene resin, and poly(chlorotrifluoroethylene).

For example, when glass is used as the substrate, non-alkali glass is preferred as its material quality in order to decrease ions eluted from the glass. When soda-lime glass is used, that subjected to barrier coating with silica or the like is preferred. On the other hand, when the organic material is used for the substrate, it has preferably excellent heat resistance, size stability, solvent resistance, electrical insulation, and workability.

No particular limitation is imposed on the shape, structure, size or the like of the substrate and it may be selected as needed, depending on the intended use, purpose or the like of the electroluminescent device. In general, a plate-like substrate is preferred as the substrate. The substrate may have a single layer structure or a multilayer structure. Further, the substrate may be formed from a single member or two or more members.

Although the substrate may be either colorless and transparent or colored and transparent, the former is preferred because such a substrate does not scatter or attenuate light emitted from the organic light emitting layer.

The substrate may be provided with a moisture permeation preventive layer (gas barrier layer) on the surface or back surface of the substrate.

As a material of the moisture permeation preventive layer (gas barrier layer), inorganic substances such as silicon nitride and silicon oxide are preferably employed. The moisture permeation preventive layer (gas barrier layer) can be formed using, for example, high frequency sputtering. When a thermoplastic substrate is used, a hard coat layer, an undercoat layer, or the like is provided thereon as needed.

<Anode>

No particular limitation is imposed on the shape, structure, size, and the like of the anode insofar as it has a function of supplying holes to the organic layers as an electrode. It can be selected from known electrode materials as needed, depending on the intended use or purpose of the electroluminescent device. As described above, the anode is usually provided as a transparent anode.

Preferred examples of the material for the anode include metals, alloys, metal oxides, and conductive compounds, and mixtures thereof. Specific examples of the anode material include conductive metal oxides such as tin oxides (ATO and FTO) doped with antimony or fluorine, tin oxide, zinc oxide, indium oxide, indium tin oxide (ITO), and indium zinc oxide (IZO); metals such as gold, silver, chromium, and nickel; mixtures or laminates of these metals and the conductive metal oxides; inorganic conductive materials such as copper iodide and copper sulfide; organic conductive materials such as polyaniline, polythiophene, and polypyrrole; and laminates of these inorganic or organic conductive materials with ITO. Among these, the conductive metal oxides are preferred, with ITO being especially preferred from the viewpoints of productivity, high conductivity, transparency and the like.

The anode can be formed on the substrate in accordance with a process selected appropriately from among wet processes such as printing and coating; physical processes such as vacuum deposition, sputtering, and ion plating; and chemical processes such as CVD and plasma CVD, in consideration of the suitability of it to a material constituting the anode. For example, when ITO is selected as a material for the anode, the anode may be formed in accordance with direct current sputtering, high-frequency sputtering, vacuum deposition, ion plating, or the like.

In the organic electroluminescent device of the invention, the formation position of the anode is not particularly limited and it can be selected as needed, depending on the intended use or purpose of the electroluminescent device. The anode may be formed preferably on the substrate. In this case, the anode may be formed on the entire surface on one side of the substrate or it may be formed on a part of the surface.

Patterning for forming the anode may be carried out by chemical etching utilizing photolithography or the like or physical etching utilizing laser or the like. Further, it may also be carried out by vacuum deposition, sputtering or the like through overlapped masks or by a lift-off process or a printing process.

The thickness of the anode may be selected as needed, depending on the material constituting the anode and cannot be determined in a wholesale manner, but it is usually from approximately 10 nm to 50 µm, preferably from 50 nm to 20 µm.

The resistivity of the anode is preferably $10^3$ $\Omega/\square$ or less, more preferably $10^2$ $\Omega/\square$ or less. When the anode is transparent, it may be either colorless and transparent or colored and transparent. For extracting luminescence from the transparent anode side, a light transmittance of the anode is preferably 60% or greater, more preferably 70% or greater.

In addition, a transparent anode is described in detail in *Developments of Transparent Conductive Films* supervised by Yutaka Sawada, published by C.M.C.(1999), which can be applied to the invention. When a plastic base material having low heat resistance is used, a transparent electrode using ITO or IZO and prepared by forming the film at a temperature as low as 150° C. or less is preferred.

<Cathode>

It is usually only necessary that the cathode has a function of injecting electrons to the organic layers as an electrode. No particular limitation is imposed on the shape, structure, size or the like of the cathode and it can be selected as needed from among known electrode materials, depending on the intended use or purpose of the electroluminescent device.

Materials constituting the cathode include, for example, metals, alloys, metal oxides, and electroconductive compounds, and mixtures thereof. Specific examples include alkali metals (such as Li, Na, K, and Cs), alkaline earth metals (such as Mg and Ca), gold, silver, lead, aluminum, sodium-potassium alloy, lithium-aluminum alloy, magnesium-silver alloy, and rare earth metals such as indium and ytterbium. They may be used singly, but it is preferred to use two or more of them in combination from the standpoint of satisfying both stability and electron injection property.

Of these, alkali metals and alkaline earth metals are preferred as the material constituting the cathode from the standpoint of an electron injection property, while materials composed mainly of silver or aluminum are preferred because they have excellent storage stability.

More specifically, the material constituting the cathode is a simple metal or an alloy containing from 0.01 to 10 mass % of an alkali metal or an alkaline earth metal, or a mixture thereof (such as lithium alloy or magnesium alloy).

The materials of the cathode are described in detail in Japanese Patent Laid-Open Nos. 15595/1990 and 121172/1993 and materials described therein can also be used in the invention.

Although no particular limitation is imposed on a cathode formation process, the cathode can be formed in accordance with a known process. It can be formed in accordance with a process selected as needed from, for example, wet processes such as printing and coating, physical processes such as vacuum deposition, sputtering, and ion plating; and chemical processes such as CVD and plasma CVD in consideration of the suitability of the process to a material constituting the cathode. For example, when a metal or the like is selected as a material of the cathode, the cathode is formed by sputtering one or more metals at the same time or sequentially.

Patterning for forming the cathode may be carried out either chemical etching utilizing photolithography or the like or physical etching utilizing laser or the like. Further, it may also be carried out by vacuum deposition, sputtering or the like through overlapped masks or by a lift-off process or a printing process.

In the invention, the formation position of the cathode is not particularly limited. It may be formed on the entire surface of the organic layer or may be formed on a part thereof.

It is also possible to insert a dielectric layer made of a fluoride, oxide or the like of an alkali metal or an alkaline earth metal between the cathode and the organic layers with a thickness of 0.1 to 5 nm. This dielectric layer may be regarded as a kind of an electron injection layer.

The dielectric layer may be formed, for example, by vacuum deposition, sputtering, or ion plating.

The thickness of the cathode may be selected as needed, depending on the material constituting the cathode and cannot be determined in a wholesale manner, but it is usually from approximately 10 nm to 5 μm, preferably from 50 nm to 1 μm.

The cathode may be either transparent or opaque. The transparent cathode can be formed by forming a material for the cathode into a film as thin as from 1 nm to 10 nm, and then stacking a transparent conductive material such as ITO or IZO thereover.

<Organic Layer>

The organic layer in the invention will next be described.

The organic layer includes a light emitting layer. Examples of the organic layer other than a light emitting layer include, as described above, a hole transport layer, an electron transport layer, a hole blocking layer, an electron blocking, a hole injection layer, and an electron injection layer.

—Formation of Organic Layer—

In the organic electroluminescent device of the invention, each organic layer can be formed preferably by any of dry film formation processes such as vapor deposition and sputtering, transfer process and printing process.

Organic layers can be formed by coating a solution containing materials for forming the layers by means of a spin-coating method and so on. Formation of layers by coating has an advantage in forming a device having a large area.

—Light Emitting Layer—

The light emitting layer has a function of, at the time of electric field application, accepting holes from the anode, hole injection layer, or hole transport layer, accepting electrons from the cathode, electron injection layer, or electron transport layer, and providing a recombination site of holes and electrons, thereby emitting light.

The light emitting layer in the invention may be composed only of a light emitting material or may be a mixed layer of a host material and a light emitting material. The light emitting material may be either a fluorescent material or a phosphorescent material. One or more dopants can be used. The host material is preferably a charge transport material. One or more host materials may be used. For example, the host material may be a mixture of an electron transporting host material and a hole transporting host material. Further, the light emitting layer may contain a material that has no electron transport property and therefore does not emit light. The light emitting layer is preferably composed of the host material and, as the light emitting material, the compound represented by the formula (I).

The light emitting layer may be a single layer or a multilayer having two or more layers. When the light emitting layer is a multilayer, the compound represented by the formula (I) may be contained in two or more light emitting layers. In addition, these light emitting layers may emit lights of different colors, respectively.

The host material used in combination with the compound represented by the formula (I) in the invention may be either a hole transporting host material or an electron transporting host material, but the hole transporting host material is preferred.

(Fluorescent Material)

Examples of the fluorescent material which can be used in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, fused aromatic compounds, perinone derivatives, oxadiazole derivatives, oxazine derivatives, aldazine derivatives, pyrralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne derivatives, various metal complexes typified by complexes of 8-quinolinol derivatives or complexes of pyrromethene derivatives, polymer compounds such as polythiophene, polyphenylene, and polyphenylenevinylene, and organosilane derivatives.

(Phosphorescent Material)

Examples of the phosphorescent material usable in the invention include, in addition to the compounds represented by the formula (I), phosphorescent compounds described in Patent Documents such as U.S. Pat. Nos. 6,303,238B1 and 6,097,147, WO00/57676, WO00/70655, WO01/08230, WO01/39234A2, WO01/41512 A1, WO02/02714A2, WO02/15645A1, WO02/44189A1, WO05/19373A2, Japanese Patent Laid-Open Nos. 2001-247859, 2002-302671, 2002-117978, 2003-133074, 2003-235076, 2003-123982, and 2002-170684, EP1211257, and Japanese Patent Laid-Open Nos. 2002-226495, 2002-234894, 2001-247859, 2001-298470, 2002-173674, 2002-203678, 2002-203679, 2004-357791, 2006-256999, 2007-19462, 2007-84635, and 2007-96259. Of these phosphorescent materials, Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes are more preferred. Especially preferred are Ir complexes, Pt complexes, and Re complexes, of which Ir complexes, Pt complexes, and Re complexes containing at least one coordination mode of a metal-carbon bond, a metal-nitrogen bond, a metal-oxygen bond, and a metal-sulfur bond are still more preferred. Furthermore, Ir complexes, Pt complexes, and Re complexes containing a tridentate or higher ligand are especially preferred from the standpoints of luminous efficiency, drive durability, and chromaticity.

The content of the phosphorescent material in the light emitting layer is preferably 0.1 mass % or greater but not greater than 50 mass %, more preferably 0.2 mass % or greater but not greater than 50 mass %, still more preferably 0.3 mass % or greater but not greater than 40 mass %, most preferably 20 mass % or greater but not greater than 30 mass %, each based on the total mass of the light emitting layer.

The content of the phosphorescent material(s) usable in the invention (the compound represented by the formula (I) and/or a phosphorescent material used in combination therewith) is preferably 0.1 mass % or greater but not greater than 50 mass %, more preferably 1 mass % or greater but not greater than 40 mass %, most preferably 5 mass % or greater but not greater than 30 mass % based on the total mass of the light emitting layer. In particular, within a content range of 5 mass % or greater but not greater than 30 mass %, the chromaticity of light emitted from the organic electroluminescent device does not depend largely on the concentration of the phosphorescent material(s).

It is most preferred that the organic electroluminescent device of the invention contains from 5 to 30 mass % of at least one of the compound (I) (compound represented by the formula (I)) based on the total mass of the light emitting layer.

(Host Material)

The host material is a main compound that is involved in injection and transport of charges in the light emitting layer and does not substantially emit light. The term "not substantially emit light" means that the amount of luminescence from the compound that does not substantially emit light is preferably 5% or less, more preferably 3% or less, still more preferably 1% or less, each of the total amount of luminescence from the whole device.

In the invention, the light emitting layer preferably contains the host material.

In the invention, the host material may be either a hole transporting host material or an electron transporting host material, but the hole transporting host material can be used.

Although no particular limitation is imposed on the concentration of the host material in the light emitting layer, the host material is preferably a main component (a component whose content is the largest) in the light emitting layer; it is contained more preferably in an amount of 50 mass % or greater but not greater than 99.9 mass %, still more preferably 50 mass % or greater but not greater than 99.8 mass %, especially preferably 60 mass % or greater but not greater than 99.7 mass %, most preferably 70 mass % or greater but not greater than 95 mass %.

The host material has a glass transition point of preferably 60° C. or greater but not greater than 500° C., more preferably 70° C. or greater but not greater than 300° C., still more preferably 90° C. or greater but not greater than 250° C.

The fluorescence wavelength of the host material, in film form, contained in the light emitting layer in the invention is preferably 400 nm or greater but not greater than 650 nm, more preferably 420 nm or greater but not greater than 600 nm, still more preferably 440 nm or greater but not greater than 550 nm.

Examples of the host material contained in the light emitting layer in the invention include materials having a carbazole skeleton, a diarylamine skeleton, an indole skeleton, a pyridine skeleton, a pyrazine skeleton, a triazine skeleton, or an arylsilane skeleton, and materials exemplified later in the description of hole injection layer, hole transport layer, electron injection layer, or electron transport layer.

As the host material to be used in the invention, for example, the compounds described in columns [0113] to [0161] of Japanese Patent Laid-Open No. 2002-100476 and the compounds described in the columns [0087] to [0098] of Japanese Patent Laid-Open No. 2004-214170 are preferred. The host material is not however limited to them.

The host material to be used in the invention is preferably a compound represented by the following formula (V). Compared with compounds such as mCP conventionally used as a host material of organic electroluminescent devices, the compound represented by the formula (V) has a higher molecular polarity and can provide a uniform film having high compatibility by using it in combination with the compound represented by the formula (I). This enables to suppress associated light emission between complexes, provide a sharp spectrum, and improve the color purity.

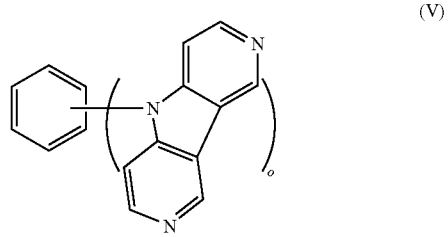

(V)

In the formula (V), o stands for an integer from 1 to 3, preferably 2. When o stands for 2 or 3, a partial structure bound to a benzene ring is desirably substituted in the meta-position relative to another partial structure.

In the invention, when the compound represented by the formula (V) is contained in the light emitting layer, the compound represented by the formula (V) is contained in the light emitting layer in an amount of preferably from 30 to 99 mass %, more preferably from 40 to 97 mass %, especially preferably from 50 to 95 mass %.

When the compound represented by the formula (V) is introduced into a layer other than the light emitting layer (for example, a charge transport layer), it is contained in the layer preferably in an amount of from 10 to 100 mass %, more preferably from 30 to 100 mass %.

As another preferred mode of the host material to be used in the invention, compounds represented by the following formulae (4-1) and (4-2) can be mentioned.

In the invention, when the compound represented by the formula (4-1) or (4-2) is contained in the light emitting layer, the compound represented by the formula (4-1) or (4-2) is contained in the light emitting layer in an amount of preferably from 30 to 99 mass %, more preferably from 40 to 97 mass %, especially preferably from 50 to 95 mass %. When the compound represented by the formula (4-1) or (4-2) is contained in a plurality of organic layers, it is preferably contained in each of the layers in an amount within the above range.

The compound represented by the formula (4-1) or (4-2) may be contained singly in any of the organic layers. Alternatively, two or more compounds represented by the formula (4-1) or (4-2) may be contained in combination at a desired ratio.

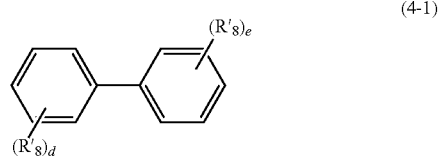

(4-1)

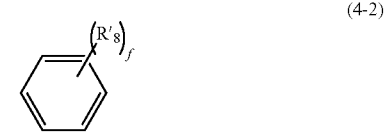

(4-2)

(in the formulae (4-1) and (4-2), d and e each stands for an integer from 0 to 3, with the proviso that at least one of them is 1 or greater, f stands for an integer from 1 to 4, and $R'_8$s each represents a substituent, with the proviso that when d, e, and f each stands for 2 or greater, $R'_8$s may be the same or different and at least one of $R'_8$s represents a carbazole group represented by the following formula (5)).

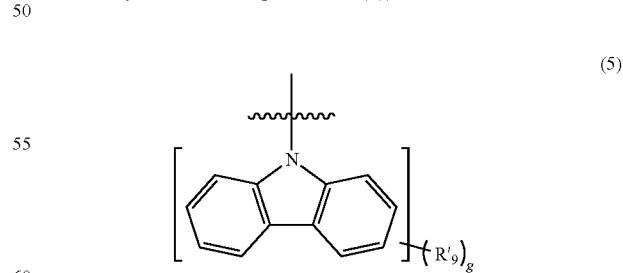

(5)

(in the formula (5), $R'_9$s each independently represents a substituent and g stands for an integer from 0 to 8).

$R'_8$s each independently represents a substituent and specific examples include halogen atoms, alkoxy groups, a cyano group, a nitro group, alkyl groups, aryl groups, heterocyclic groups, and substituents represented by the formula (5).

When R'₈s each does not represent the substituent represented by the formula (5), it is preferably an alkyl group having 10 or less carbon atoms or a substituted or unsubstituted aryl group having 10 or less carbon atoms, more preferably an alkyl group having 6 or less carbon atoms.

R'₉s each independently represents a substituent and specific examples include halogen atoms, alkoxy groups, a cyano group, a nitro group, alkyl groups, aryl groups, and heterocyclic groups. Of these, alkyl groups having 10 or less carbon atoms and substituted or unsubstituted aryl group having 10 or less carbon atoms are preferred, with alkyl groups having 6 or less carbon atoms being more preferred.

g stands for an integer from 0 to 8. It is preferably from 0 to 4, more preferably 0 or 1 from the standpoint of not excessively blocking a carbazole skeleton involved in charge transport. From the standpoint of synthesis ease, when the carbazole has a substituent, it is preferred to have the substituent symmetrical relative to the nitrogen atom.

In the formula (4-1), the sum of d and e is preferably 2 or greater in order to keep a charge transport ability. Further, it is preferred that R'₈ is substituted in the meta position relative to the other benzene ring, because since the steric hindrance between substituents adjacent to each other is large in the case of an ortho substitution, the linkage easily cleaves and durability deteriorates. In the case of para substitution, on the other hand, the molecule approximates a rigid rod shape and tends to cause crystallization so that device deterioration easily occurs under high temperature conditions. Specifically, compounds represented by the following structure are preferred.

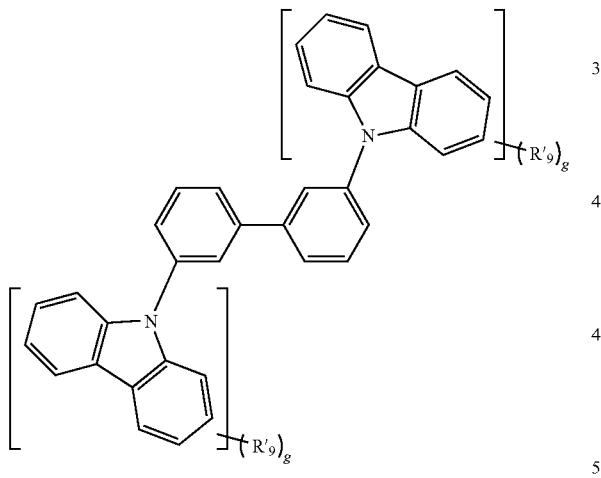

In the formula (4-2), f stands for preferably 2 or greater in order to keep the charge transport ability. When f stands for 2 or 3, meta-substitution between R'₈s is preferred from the same standpoint. Specifically, it is preferably a compound represented by the following structure.

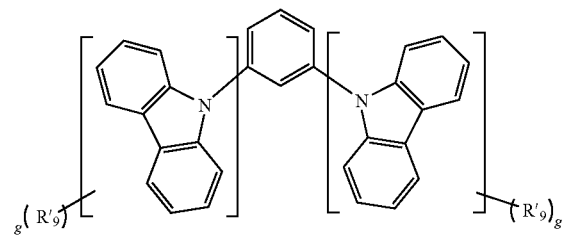

When the compound of the formula (4-1) or (4-2) has hydrogen atoms, the hydrogen atoms each may be an isotope thereof (such as deuterium atom). In this case, all the hydrogen atoms contained in the compound may be replaced with hydrogen isotopes or the compound may be a mixture of the compound containing hydrogen isotopes partially. Preferably, R'₉ of the formula (5) is substituted with a deuterium, with the following structures being especially preferred.

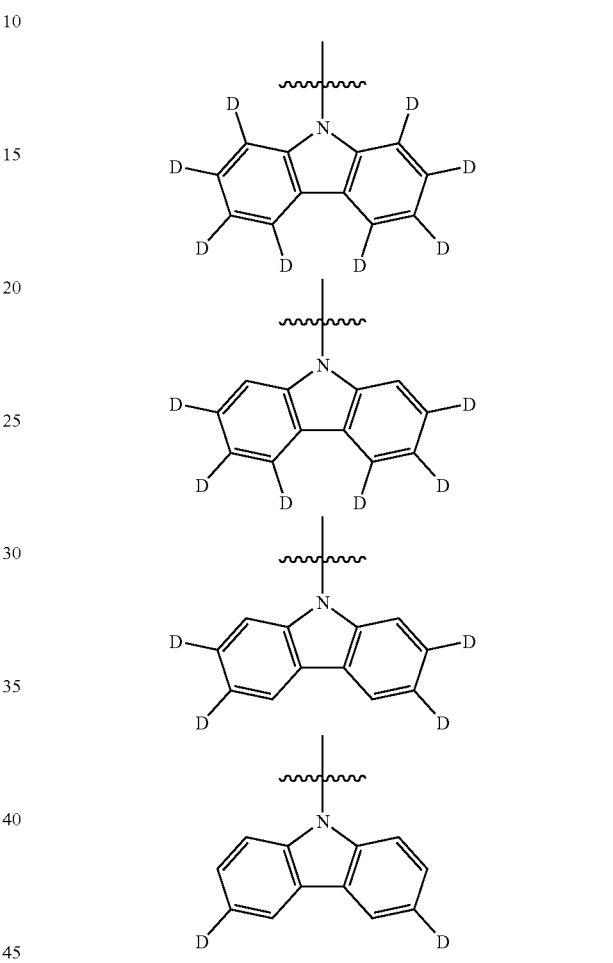

Further, the atom constituting the substituent may include an isotope thereof.

The compound represented by the formula (4-1) or (4-2) can be synthesized by using various known synthesis processes in combination. It is the most common to prepare a carbazole compound by carrying out an aza-Cope rearrangement reaction of a condensate between an aryl hydrazine and a cyclohexane derivative, followed by dehydroaromatization (L. F. Tietze and Th. Eicher, *Precision Organic Synthesis*, translated by Takano and Ogasawara, published by Nankodo, p339). For a coupling reaction between the resulting carbazole compound and an aryl halide compound in the presence of a palladium catalyst, processes described in *Tetrahedron Letters*, 39, 617(1998); 39, 2367(1998); and 40, 6393(1999) can be used. No particular limitation is imposed on the reaction temperature and reaction time and conditions described in the above-described literatures can be employed. Some of commercially available compound such as mCP can also be used preferably.

In the invention, it is preferred to form a thin layer of the compound represented by the formula (4-1) or (4-2) by using vapor deposition, but wet process such as application of a solution is preferred. The compound has a molecular weight of preferably 2000 or less, more preferably 1200 or less, especially preferably 800 or less from the standpoints of deposition suitability and solubility. From the viewpoint of deposition suitability, the compound has a molecular weight of preferably 250 or greater, especially preferably 300 or greater, because too small molecular weight decreases vapor pressure and prevents occurrence of a change from a gas phase to a solid phase, making it difficult to form an organic layer.

The compound represented by the formula (4-1) or (4-2) is preferably a compound having the following structure or having the following structure in which one or more of the hydrogen atoms have been substituted with a deuterium atom.

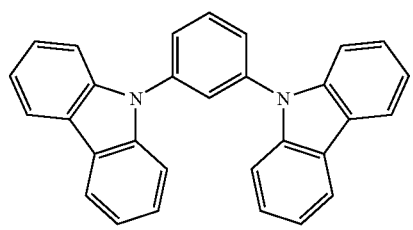

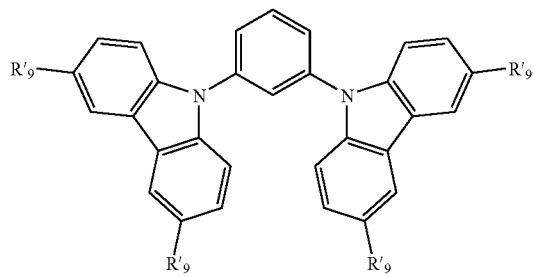

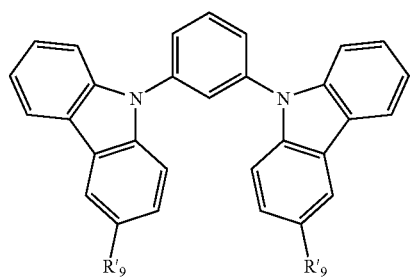

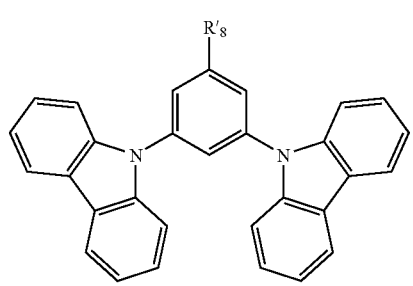

-continued

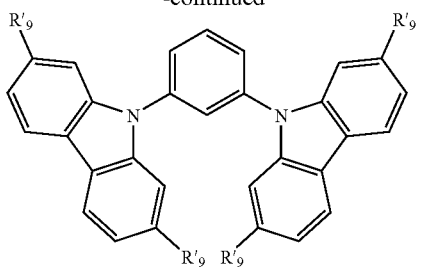

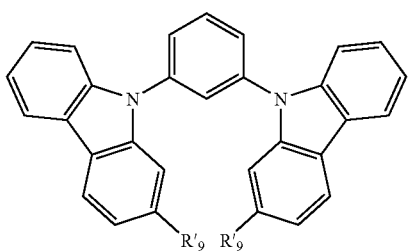

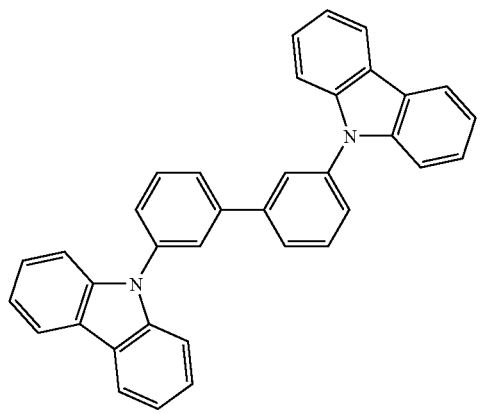

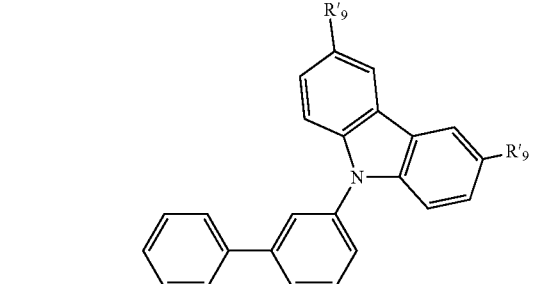

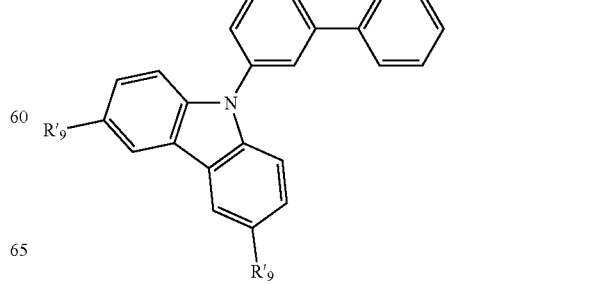

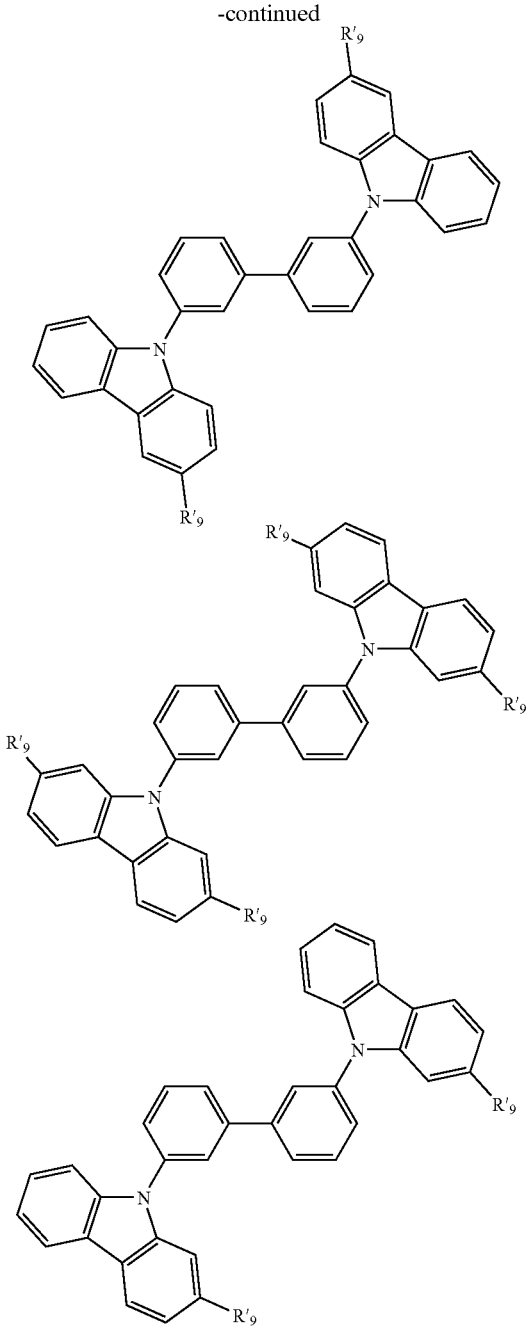
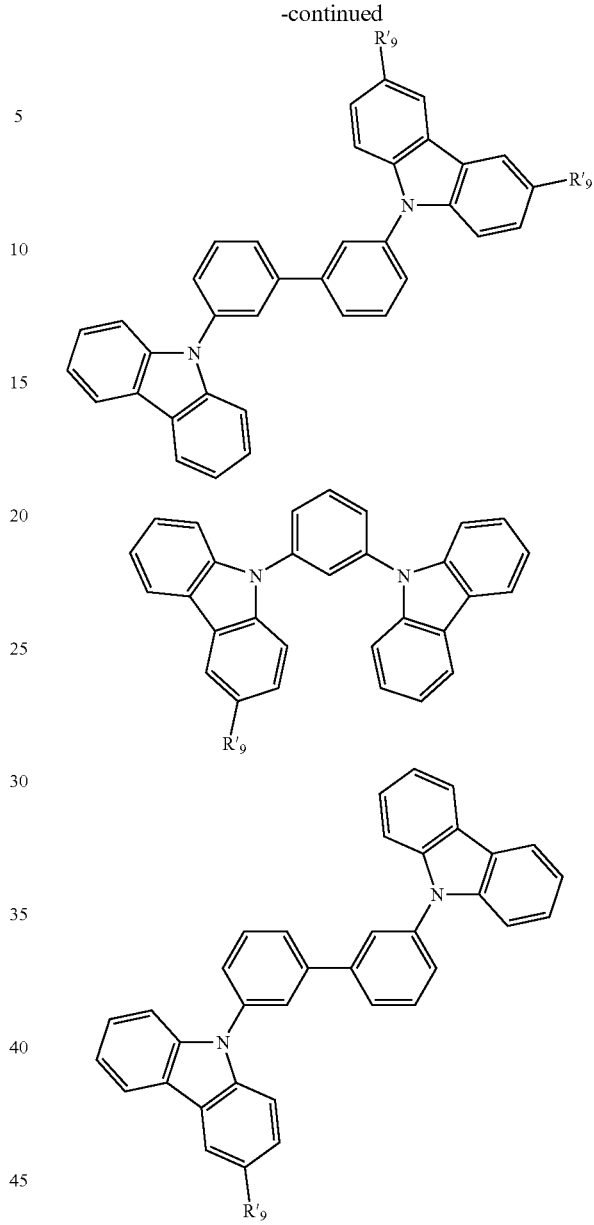
The following are specific examples of the compound represented by the formula (4-1) or (4-2) in the invention, but the present invention is not limited to them.
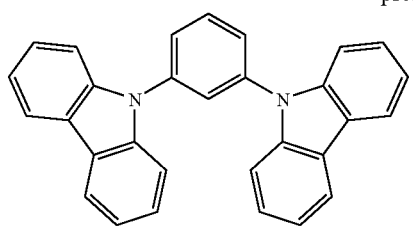
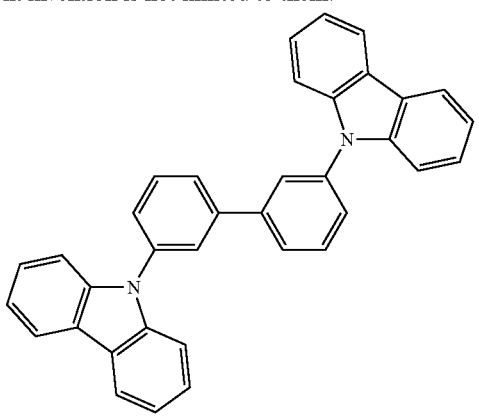

-continued
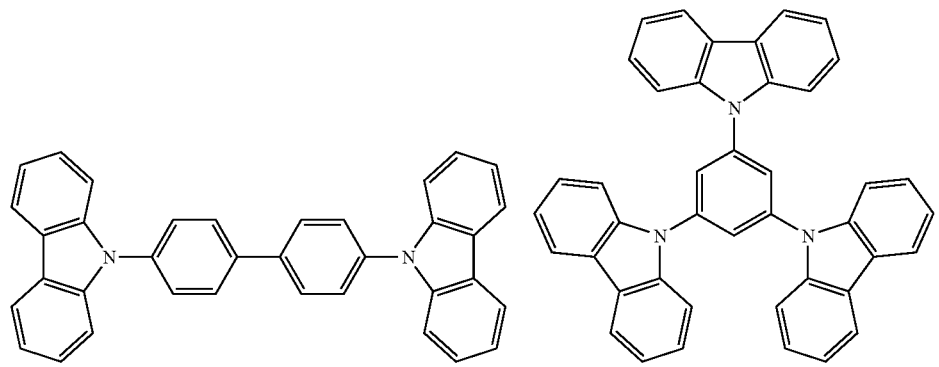
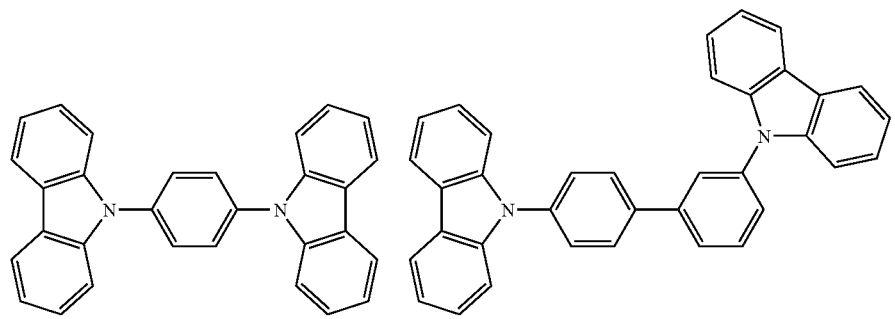
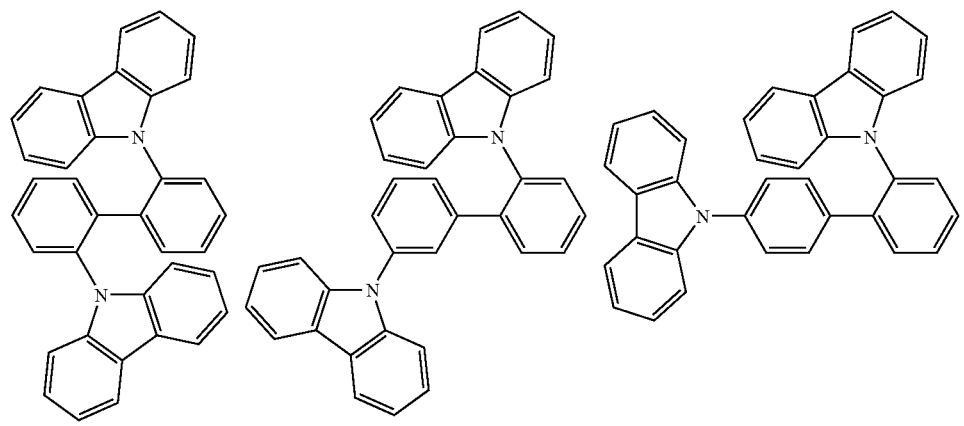
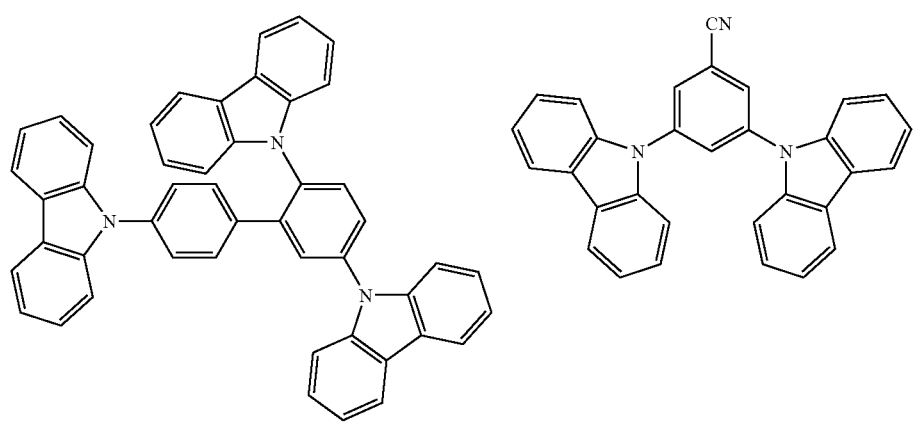

-continued
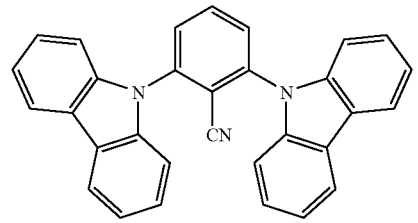
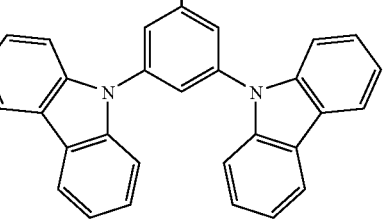
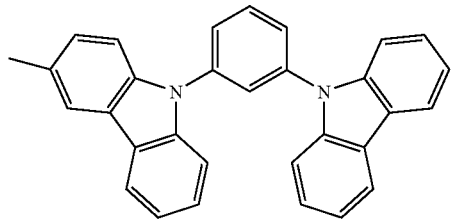
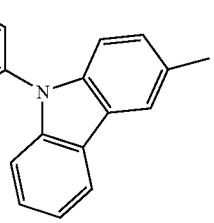
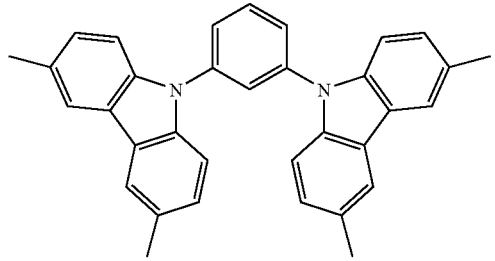
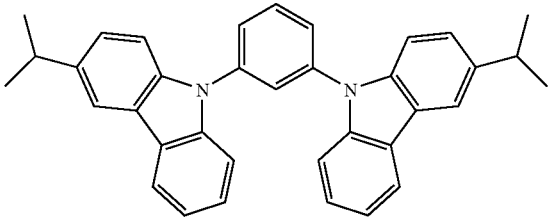
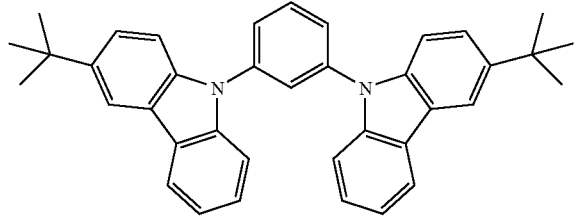
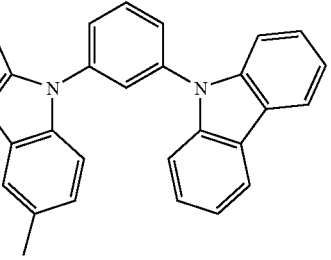
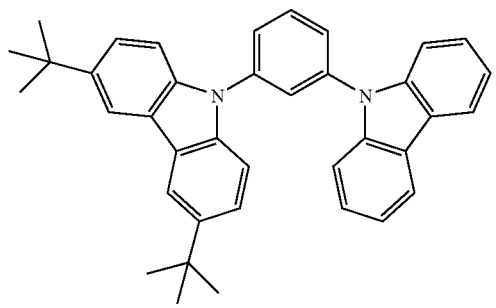
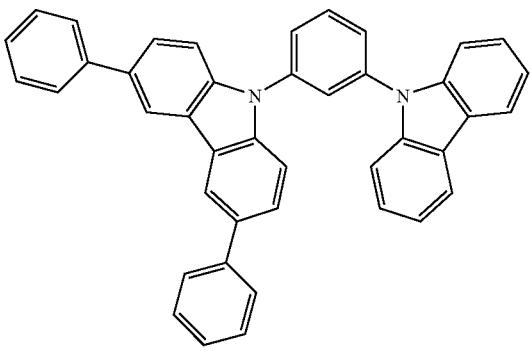
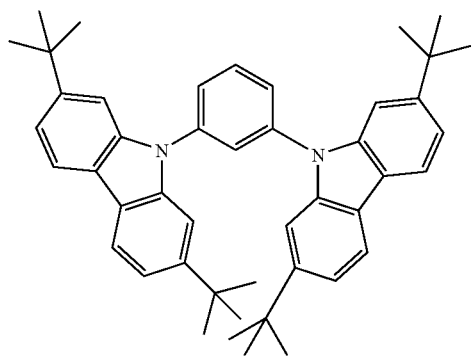
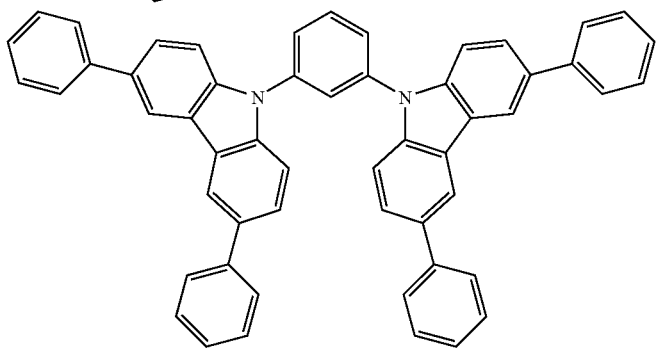

-continued
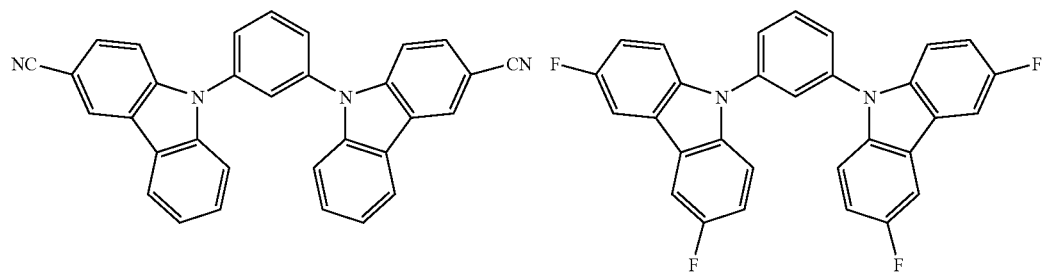
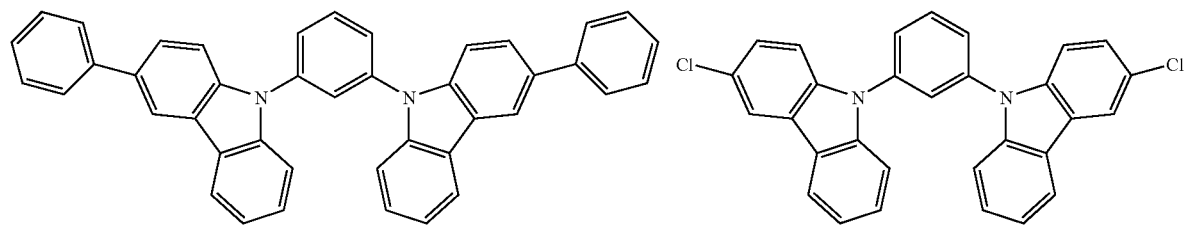
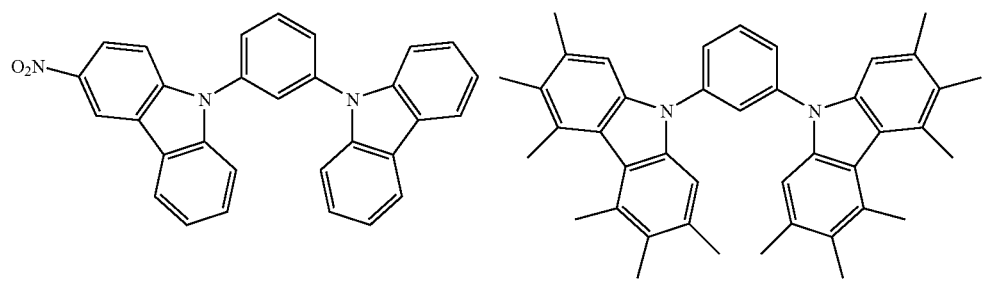
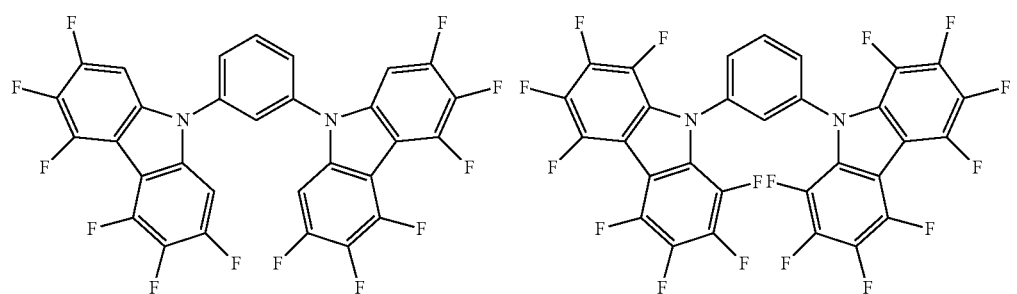
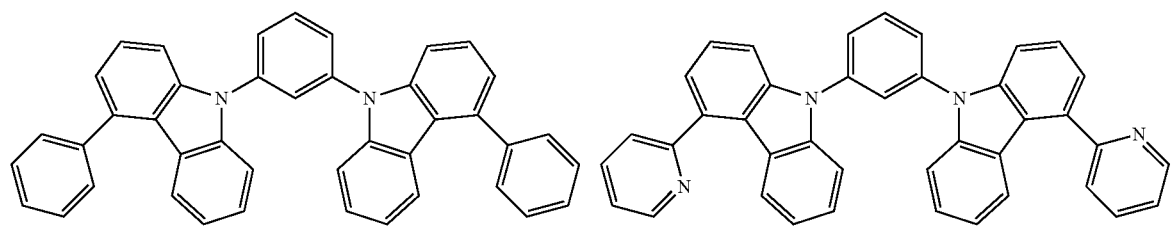
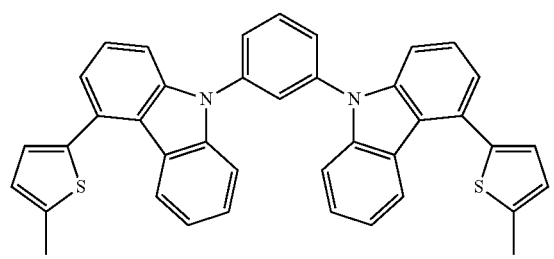

-continued
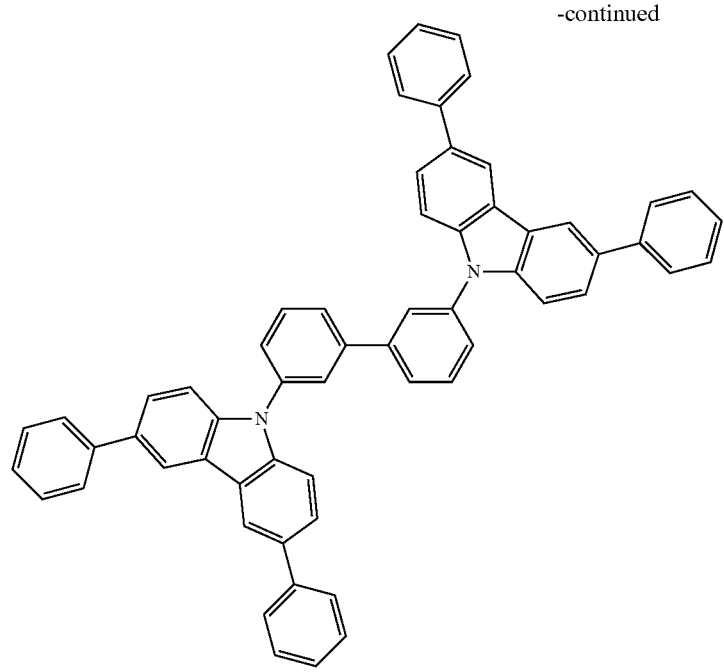
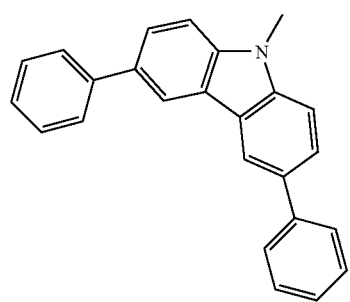
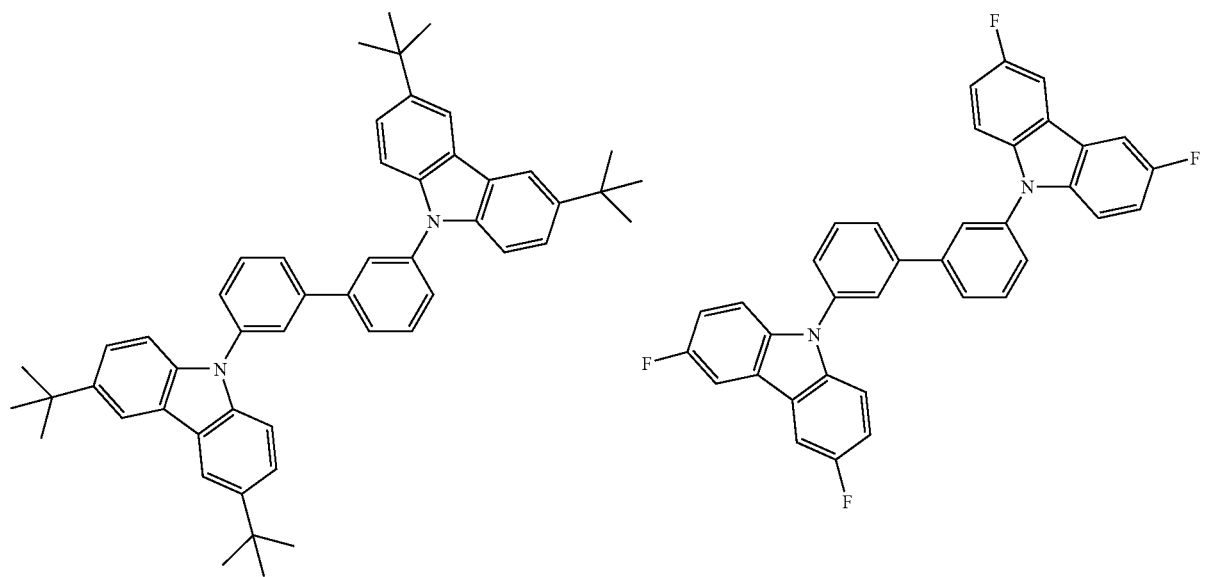

97
98
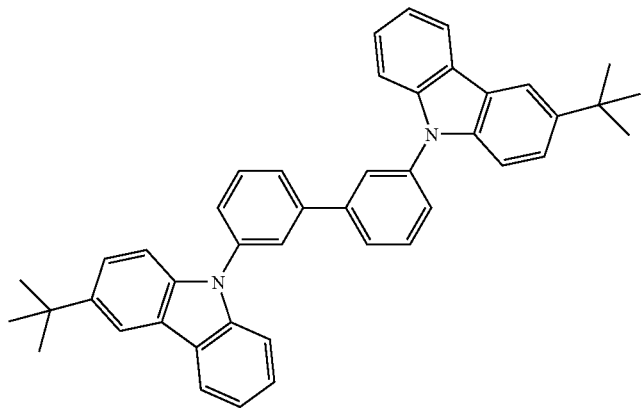
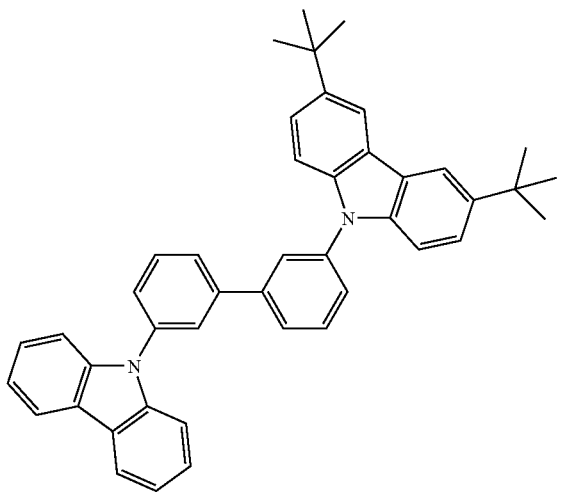
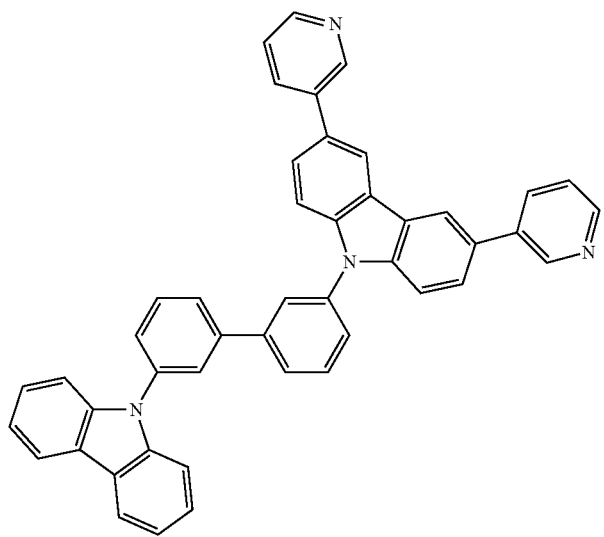
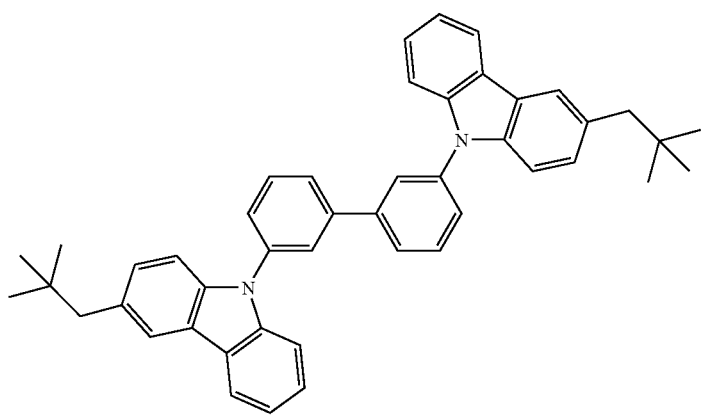

-continued
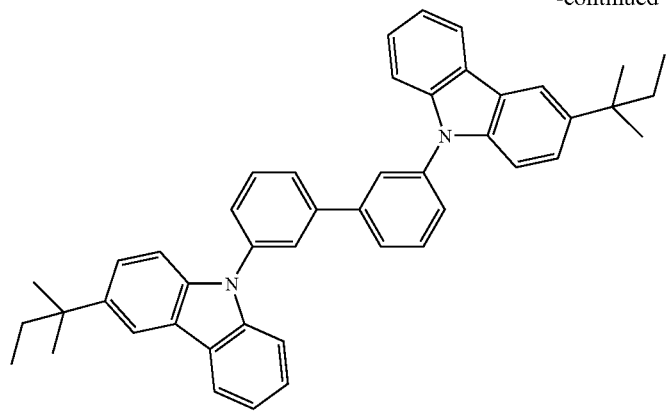
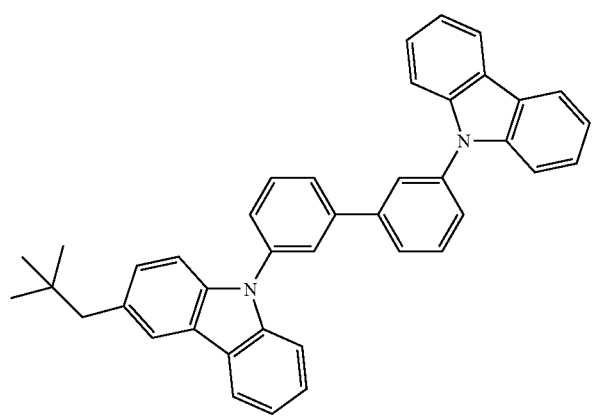
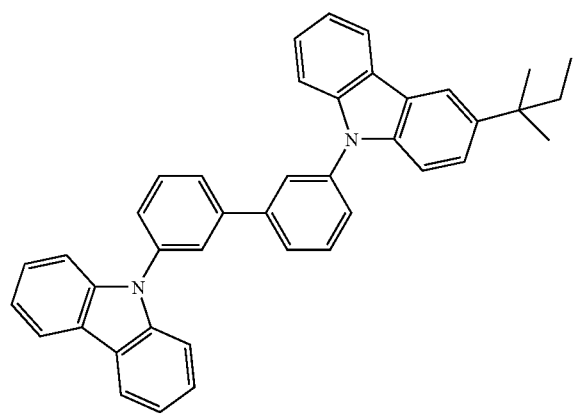

-continued
101
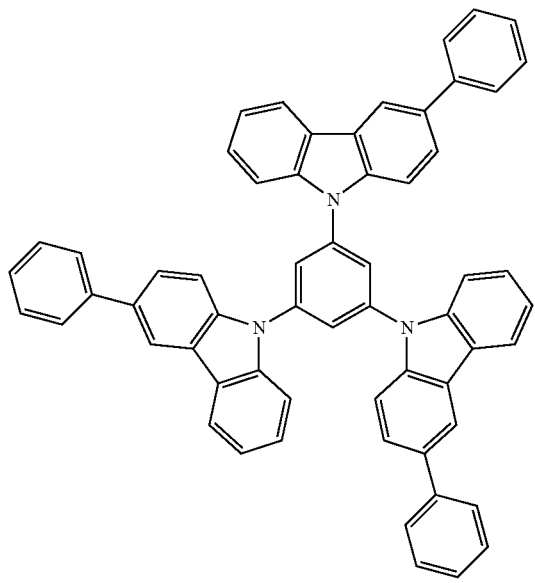
102
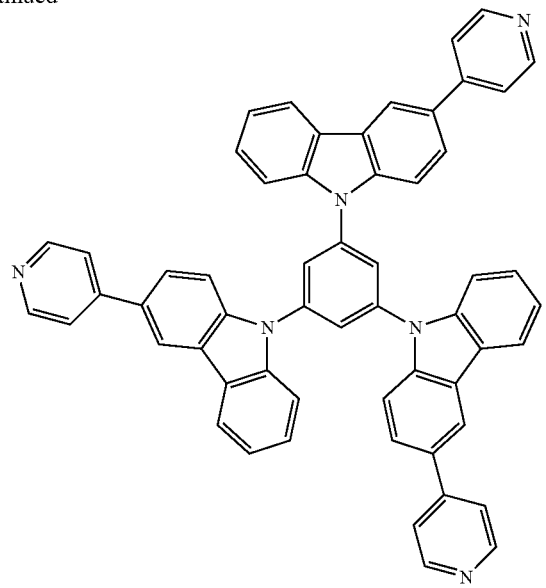
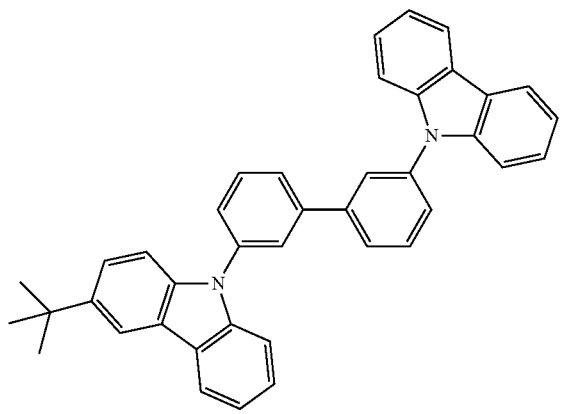
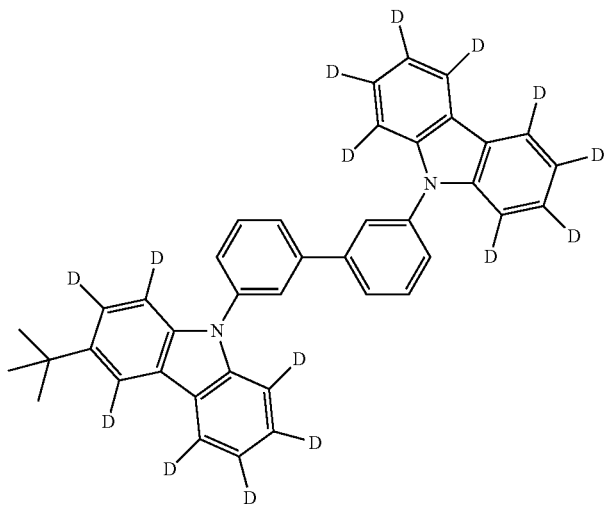
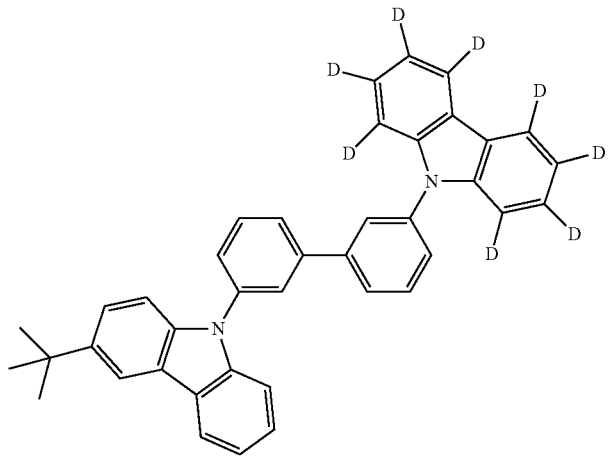
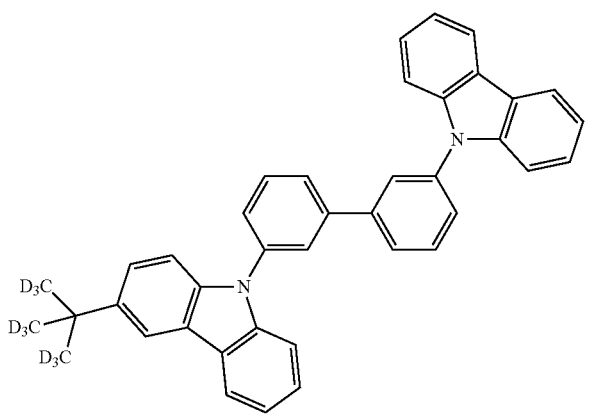

-continued
103
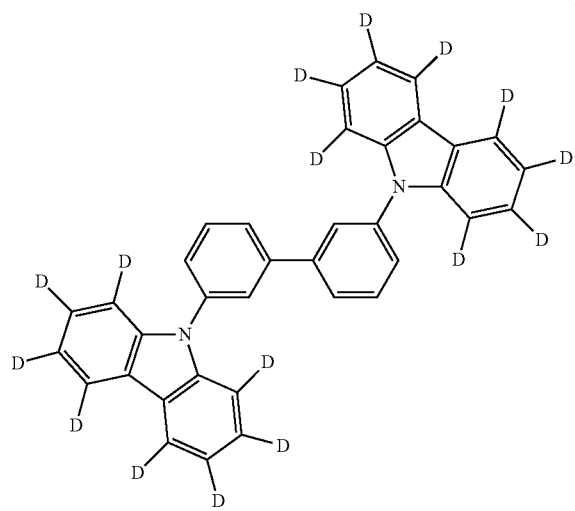
104
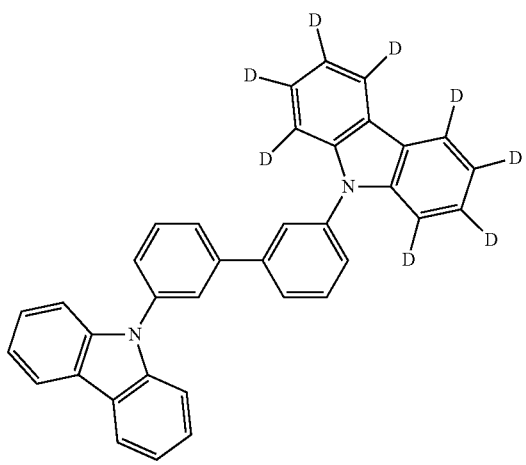
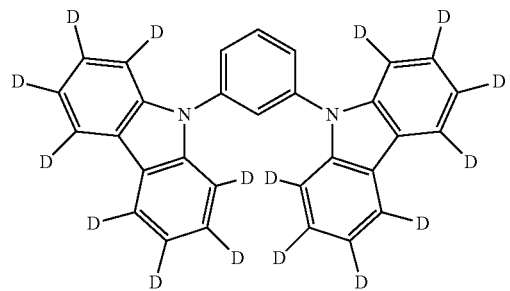
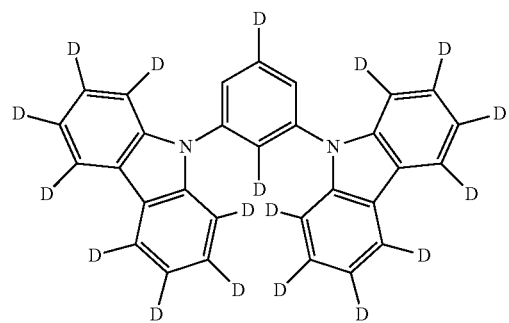
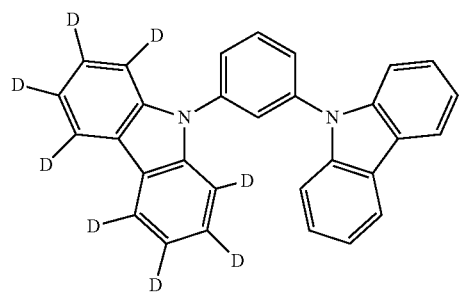
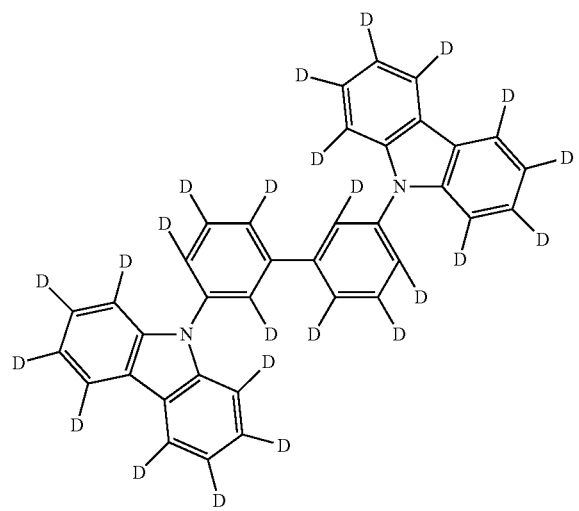

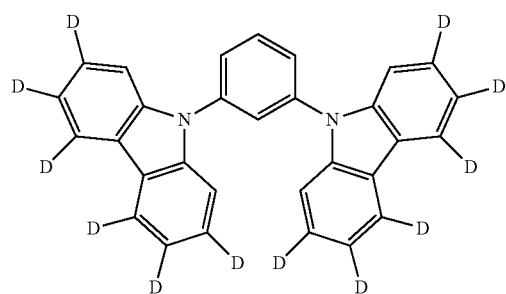

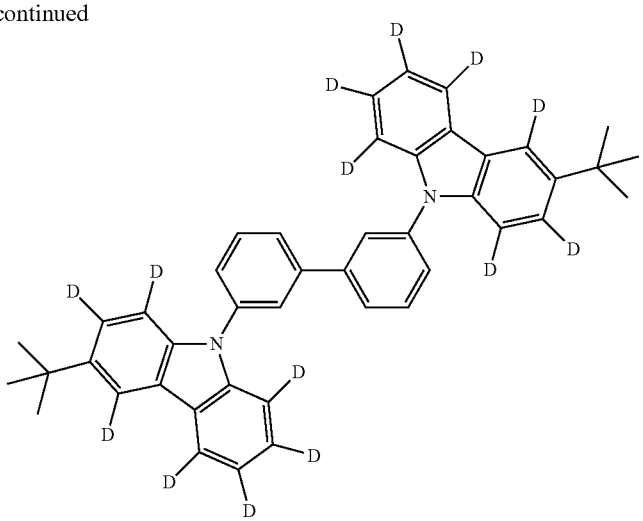

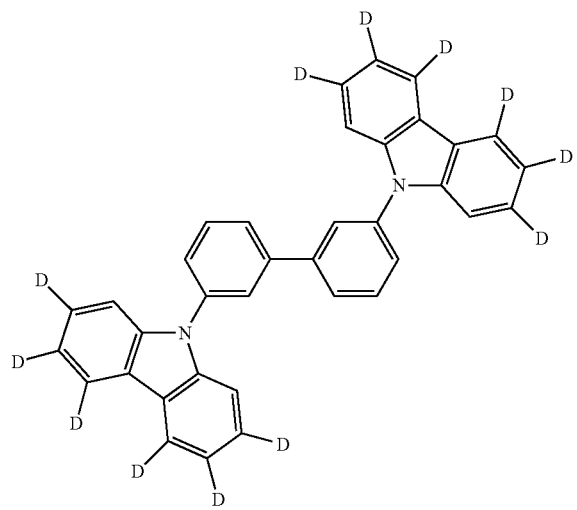 [SMILES: [2H]c1cc2c(c([2H])c1[2H])c1c([2H])c([2H])c([2H])cc1n2-c1cccc(-c2cccc(-n3c4cc([2H])c([2H])c([2H])c4c4c([2H])c([2H])c([2H])cc43)c2)c1]

It is preferred that the organic electroluminescent device further contains a compound represented by the following formula (VI).

It is possible to reduce a drive voltage further by properly using the compound represented by the formula (VI) together with the light emitting material, thereby properly controlling the interaction between their material molecules and equalizing the energy gap interaction between adjacent molecules uniform.

The compound represented by the formula (VI) to be used in the organic electroluminescent device is excellent in chemical stability so that it does not undergo a quality change such as decomposition of the material during operation of the device. It is therefore possible to prevent deterioration in efficiency of the organic electroluminescent device or reduction in the life of the device due to the decomposition product of the material.

The compound represented by the formula (VI) will next be described.

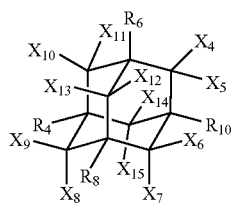
(VI)

In the formula (VI), $R_4$, $R_6$, $R_8$, $R_{10}$, and $X_4$ to $X_{15}$ each independently represents a hydrogen atom, an alkyl group, or an aryl group.

The alkyl group represented by $R_4$, $R_6$, $R_8$, $R_{10}$, and $X_4$ to $X_{15}$ in the formula (VI) may be substituted with an adamantane structure or an aryl structure. The alkyl group has preferably from 1 to 70 carbon atoms, more preferably from 1 to 50 carbon atoms, still more preferably from 1 to 30 carbon atoms, still more preferably from 1 to 10 carbon atoms, especially preferably from 1 to 6 carbon atoms. The alkyl group is most preferably a linear $C_{2-6}$ one.

Examples of the alkyl group represented by $R_4$, $R_6$, $R_8$, $R_{10}$, and $X_4$ to $X_{15}$ in the formula (VI) include an n-$C_{50}H_{101}$ group, an n-$C_{30}H_{61}$ group, a 3-(3,5,7-triphenyladamantan-1-yl)propyl group (31 carbon atoms), a trityl group (19 carbon atoms), a 3-(adamantan-1-yl)propyl group (13 carbon atoms), a 9-decaryl group (10 carbon atoms), a benzyl group (7 carbon atoms), a cyclohexyl group (6 carbon atoms), an n-hexyl group (6 carbon atoms), an n-pentyl group (5 carbon atoms), an n-butyl group (4 carbon atoms), an n-propyl group (3 carbon atoms), a cyclopropyl group (3 carbon atoms), an ethyl group (2 carbon atoms), and a methyl group (one carbon atom).

The aryl group represented by $R_4$, $R_6$, $R_8$, $R_{10}$, and $X_4$ to $X_{15}$ in the formula (VI) may be substituted with an adamantane or alkyl structure. It has preferably from 6 to 30 carbon atoms, more preferably from 6 to 20 carbon atoms, still more preferably from 6 to 15 carbon atoms, especially preferably from 6 to 10 carbon atoms, most preferably 6 carbon atoms.

Examples of the aryl group represented by $R_4$, $R_6$, $R_8$, $R_{10}$, and $X_4$ to $X_{15}$ in the formula (VI) include a 1-pyrenyl group (16 carbon atoms), a 9-anthracenyl group (14 carbon atoms), a 1-naphthyl group (10 carbon atoms), a 2-naphthyl group (10 carbon atoms), a p-t-butylphenyl group (10 carbon atoms), a 2-m-xylyl group (8 carbon atoms), a 5-m-xylyl group (8 carbon atoms), an o-tolyl group (7 carbon atoms), a m-tolyl group (7 carbon atoms), a p-tolyl group (7 carbon atoms), and a phenyl group (6 carbon atoms).

$R_4$, $R_6$, $R_8$, and $R_{10}$ in the formula (VI) may be any of a hydrogen atom, an alkyl group, or an aryl group, but preferably at least one of them, more preferably at least two of them, especially preferably three or four of them are each an aryl group because a high glass transition point is preferred as described above.

$X_4$ to $X_{15}$ in the formula (VI) each may be any of a hydrogen atom, an alkyl group, or an aryl group, but it is preferably a hydrogen atom or an aryl group, especially preferably a hydrogen atom.

The molecular weight of the compound represented by the formula (VI) in the invention is preferably 2000 or less, more preferably 1200 or less, especially preferably 1000 or less from the standpoint of deposition suitability and solubility because the organic electroluminescent device is fabricated using a vacuum deposition process or solution application process. The molecular weight is preferably 250 or greater, more preferably 350 or greater, especially preferably 400 or greater because from the standpoint of deposition suitability, when the molecular weight is too small, vapor pressure decreases and a change from a gas phase to a solid phase does not occur, making it difficult to form an organic layer.

The compound represented by the formula (VI) is preferably in solid form at room temperature (25° C.), more preferably within a range of from room temperature (25° C.) to 40° C., especially preferably within a range of from room temperature (25° C.) to 60° C.

Even when the compound represented by the formula (VI) does not form a solid at room temperature (25° C.), it can be made to form a solid phase at normal temperature by using another material in combination.

The intended use of the compound represented by the formula (VI) is not limited and the compound may be contained in any of the organic layers. In the invention, the compound represented by the formula (VI) is introduced preferably into any one of the light emitting layer, hole injection layer, hole transport layer, electron transport layer, electron injection layer, exciton blocking layer and charge blocking layer which will be described later, or into a plurality of these layers; more preferably into any one of the light emitting layer, hole injection layer, hole transport layer, electron transport layer, and electron injection layer or into a plurality of these layers; especially preferably into any of the light emitting layer, hole injection layer and hole transport layer or into a plurality of these layers; most preferably into the light emitting layer.

When the compound represented by the formula (VI) is used in the organic layers, the content of the compound represented by the formula (VI) should be limited so as not to suppress the charge transport property. The compound represented by the formula (VI) in the invention is contained preferably in an amount of from 0.1 to 70 mass %, more preferably from 0.1 to 30 mass %, especially preferably from 0.1 to 25 mass %.

When the compound represented by the formula (VI) is contained in two or more of the organic layers, the content of it in each of these layers is preferably controlled to fall within the above range.

One of the compounds represented by the formula (VI) may be contained in any of the organic layers or two or more of the compounds represented by the formula (VI) may be contained in any of the organic layers at any ratio.

The following are specific examples of the compound represented by the formula (VI), but it is not limited to them.

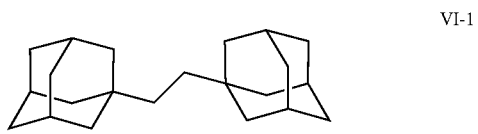

VI-1

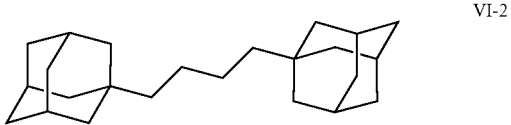

VI-2

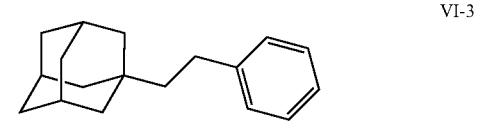

VI-3

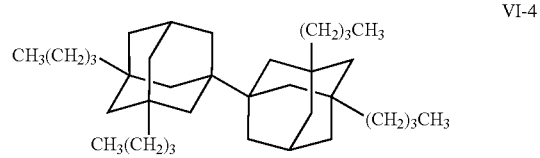

VI-4

VI-1: molecular weight: 298.5, melting point: 289° C.
VI-2: molecular weight: 326.6, melting point: 130-132° C.
VI-3: molecular weight: 240.4, melting point: 61-62° C.
VI-4: molecular weight: 494.9, melting point: 73-74° C.

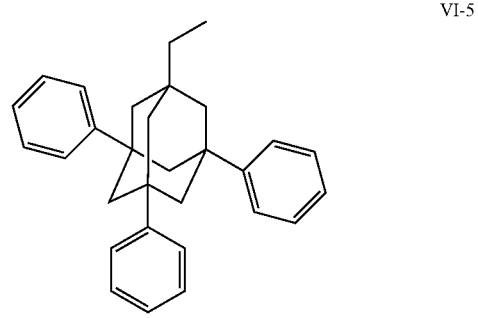

VI-5

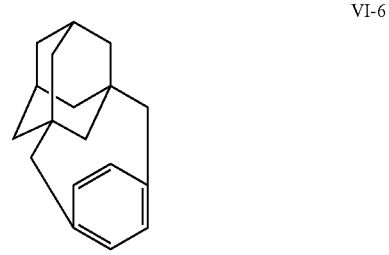

VI-6

VI-7
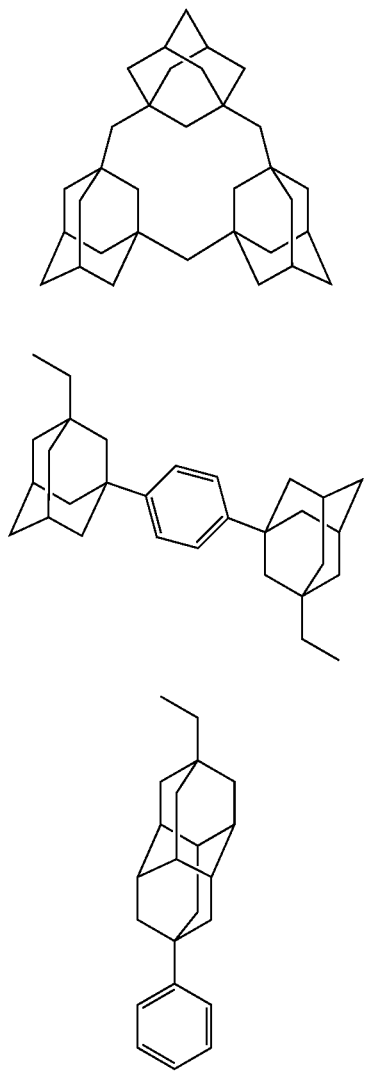
VI-8
VI-9
VI-5: molecular weight: 392.58, melting point: 192° C.
VI-6: molecular weight: 266.4, melting point: 95° C.
VI-7: molecular weight: 486.8, melting point: 178° C.
VI-8: molecular weight: 402.7, melting point: 105-106° C.
VI-9: molecular weight: 292.46
VI-10
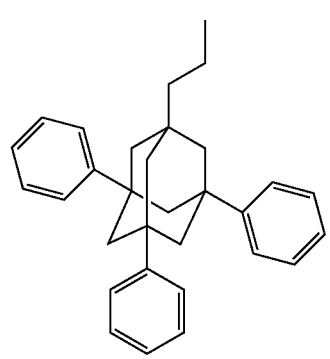
VI-11
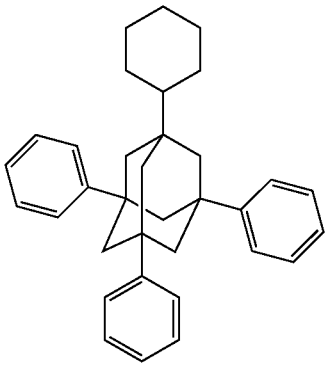
VI-12
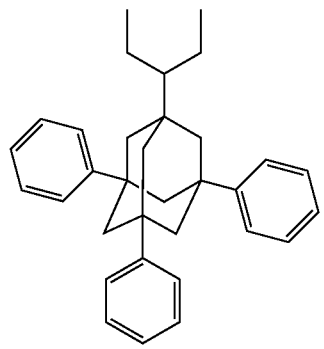
VI-13
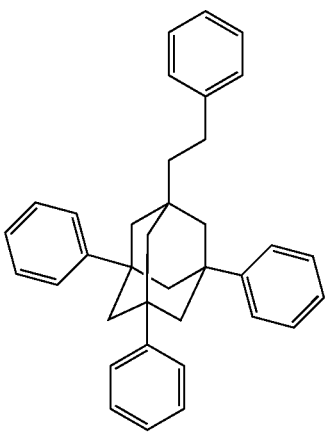
VI-14
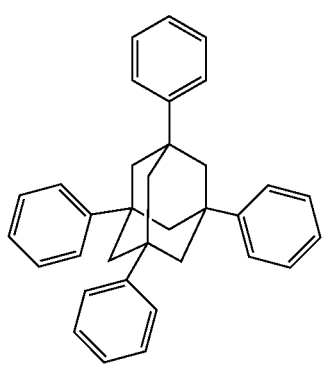
VI-10: molecular weight: 406.6
VI-11: molecular weight: 446.7
VI-12: molecular weight: 434.7
VI-13: molecular weight: 468.7
VI-14: molecular weight: 440.6

The compound represented by the formula (VI) can be synthesized by properly combining adamantane or halogenated adamantane with an alkyl halide or alkyl magnesium halide (Grignard reagent). For example, a halogenated adamantane and an alkyl halide can be coupled by using indium (Document 1). It is also possible to convert an alkyl halide into a corresponding alkyl copper reagent and couple it with a Grignard reagent of an aromatic compound (Document 2). It is also possible to couple an alkyl halide and a proper aryl boric acid in the presence of a palladium catalyst (Document 3).

Document 1: *Tetrahedron Lett.*, 39, 9557-9558(1998)
Document 2: *Tetrahedron Lett.*, 39, 2095-2096(1998)
Document 3: *J. Am. Chem. Soc.*, 124, 13662-13663(2002)

An adamantane skeleton having an aryl group can be synthesized by using adamantane or a halogenated adamantane and a corresponding arene or aryl halide in proper combination.

In the above-described preparation processes, when defined substituents change under the condition of a certain synthesis process or they are inappropriate to perform the process, the compound can be prepared more easily by protecting or deprotecting functional groups (e.g., T. W. Greene, *Protective Groups in Organic Synthesis*, John Wiley & Sons Inc. (1981)). Further, if necessary, it is also possible to change the order of reaction steps such as introduction of a substituent as needed.

Although the thickness of the light emitting layer is not particularly limited, usually it is preferably from 1 nm to 500 nm, more preferably from 5 to 200 nm, still more preferably from 10 to 100 nm.

The organic electroluminescent device of the invention preferably contains an anode as the electrode, has a charge transport layer between the light emitting layer and the anode, and contains a carbazole compound in the charge transport layer.

(Charge Transport Layer)

The term "charge transport layer" means a layer in which transfer of charges occurs when a voltage is applied to the organic electroluminescent device. More specifically, it may be a hole injection layer, a hole transport layer, an electron blocking layer, a light emitting layer, a hole blocking layer, an electron transport layer, or an electron injection layer, preferably a hole injection layer, a hole transport layer, an electron blocking layer, or a light emitting layer. When the charge transport layer formed by the process of application is a hole injection layer, a hole transport layer, an electron blocking layer, or a light emitting layer, a high-efficiency organic electroluminescent device can be manufactured at a low cost. The charge transport layer is more preferably a hole injection layer, a hole transport layer, or an electron blocking layer.

—Hole Injection Layer, Hole Transport Layer—

The hole injection layer or hole transport layer is a layer having a function of accepting holes from an anode or an anode side and transporting them to a cathode side. Specifically, the hole injection layer or hole transport layer is preferably a layer containing a carbazole derivative, a triazole derivative, an oxazole derivative, an oxadiazole derivative, an imidazole derivative, a polyarylalkane derivative, a pyrazoline derivative, a pyrazoline derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, a porphyrin compound, an organic silane derivative, carbon, or the like.

The hole injection layer or hole transport layer preferably contains a carbazole compound.

In the invention, the carbazole compound is preferably a carbazole compound represented by the following formula (a):

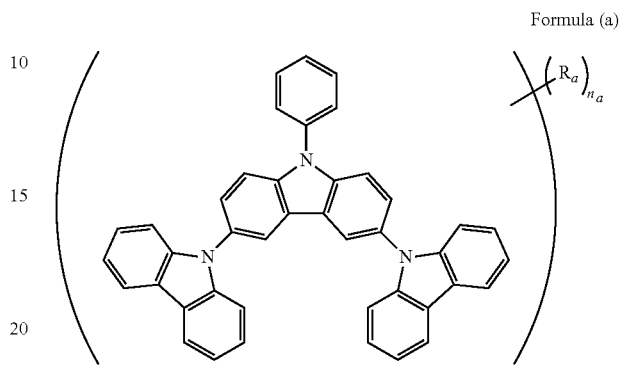

Formula (a)

(in the formula (a), $R_a$ represents a substituent substitutable on the hydrogen atom of the skeleton, with the proviso that when there are a plurality of Rs, they may be the same or different, and $n_a$ stands for an integer from 0 to 8).

When the compound represented by the formula (a) is used in the hole transport layer, the content of the compound represented by the formula (a) therein is preferably from 50 to 100 mass %, more preferably from 80 to 100 mass %, especially preferably from 95 to 100 mass %.

When the compound represented by the formula (a) is used in two or more organic layers, the content of the compound in each of the layers is preferably within the above-described range.

One of the compounds represented by the formula (a) may be contained in any of the organic layers or a combination, at any ratio, of two or more of the compounds represented by the formula (a) may be contained in any of the organic layers.

In the invention, when the compound represented by the formula (a) is contained in the hole transport layer, the thickness of the hole transport layer containing the compound represented by the formula (a) is preferably from 1 to 500 nm, more preferably from 3 to 200 nm, still more preferably from 5 to 100 nm. The hole transport layer is preferably provided adjacent to the light emitting layer.

The hole transport layer may have a single layer structure comprised of one or more of the above-described materials or a multilayer structure comprised of a plurality of layers having the same composition or different compositions.

Specific examples of the substituent represented by $R_a$ include halogen atoms, alkoxy groups, a cyano group, a nitro group, alkyl groups, aryl groups, and aromatic heterocyclic groups. Of these, alkyl groups having 10 or less carbon atoms and substituted or unsubstituted aryl groups having 10 or less carbon atoms are preferred, with alkyl groups having 6 or less carbon atoms being more preferred. $n_a$ stands for preferably from 0 to 4, more preferably from 0 to 2.

In the invention, the hydrogen atoms constituting the formula (a) may include an isotope of hydrogen (such as deuterium atom). In this case, all the hydrogen atoms contained in the compound may be replaced with hydrogen isotopes or the compound may be a mixture of the compound containing hydrogen isotopes partially.

The compounds represented by the formula (a) can be synthesized by using various known synthesis processes in combination. It is the most common to prepare a carbazole compound by carrying out an aza-Cope rearrangement reaction of a condensate between an aryl hydrazine and a cyclohexane derivative, followed by dehydroaromatization (L. F. Tietze and Th. Eicher, *Precision Organic Synthesis*, translated by Takano and Ogasawara, published by Nankodo, p339). For a coupling reaction between the resulting carbazole compound and an aryl halide compound in the presence of a palladium catalyst, processes described in *Tetrahedron Letters*, 39, 617(1998); 39, 2367(1998); and 40, 6393(1999) can be used. No particular limitation is imposed on the reaction temperature and reaction time and conditions described in the above-described literatures can be employed.

In the invention, it is preferred to form a thin layer of the compound represented by the formula (a) by using vapor deposition, but wet process such as application of a solution is also preferred. The compound has a molecular weight of preferably 2000 or less, more preferably 1200 or less, especially preferably 800 or less from the standpoints of deposition suitability and solubility. From the viewpoint of deposition suitability, the compound has a molecular weight of preferably 250 or greater, especially preferably 300 or greater, because too small molecular weight decreases vapor pressure and prevents occurrence of a change from a gas phase to a solid phase, making it difficult to form an organic layer.

The following are specific examples of the compound represented by the formula (a) in the invention, but the compound is not limited to them in the invention.

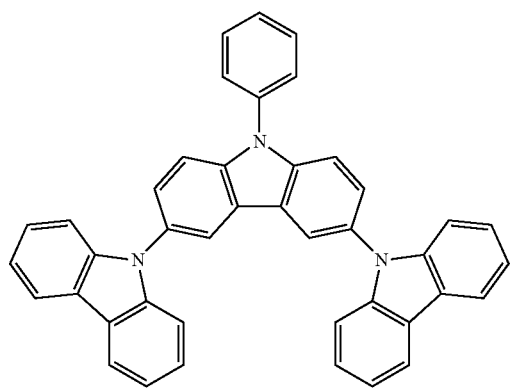

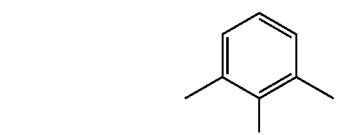

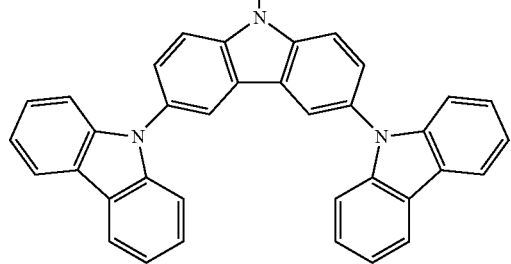

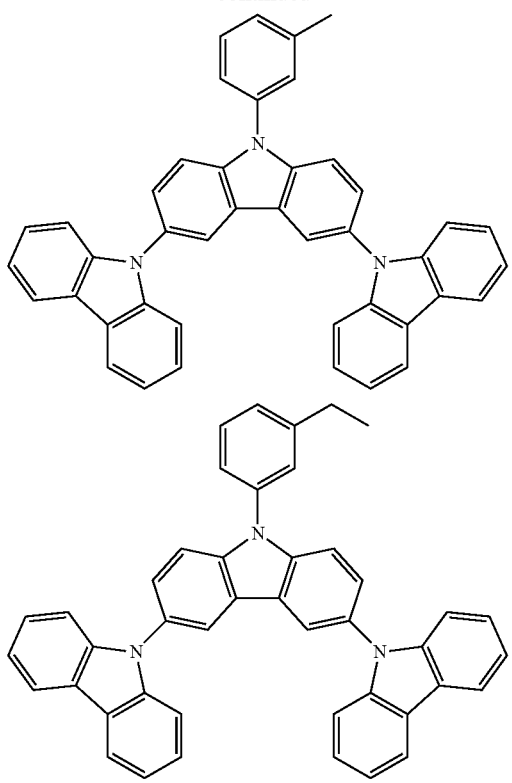

-continued

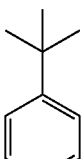

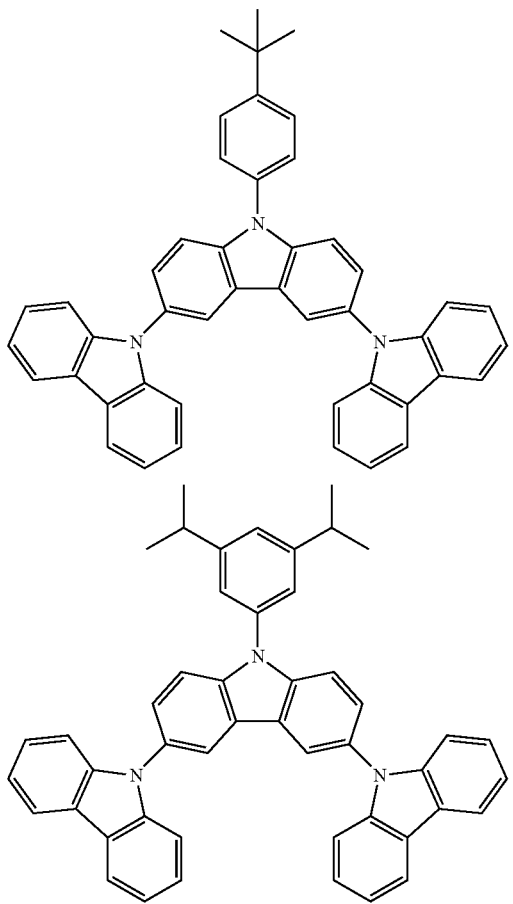

115
-continued
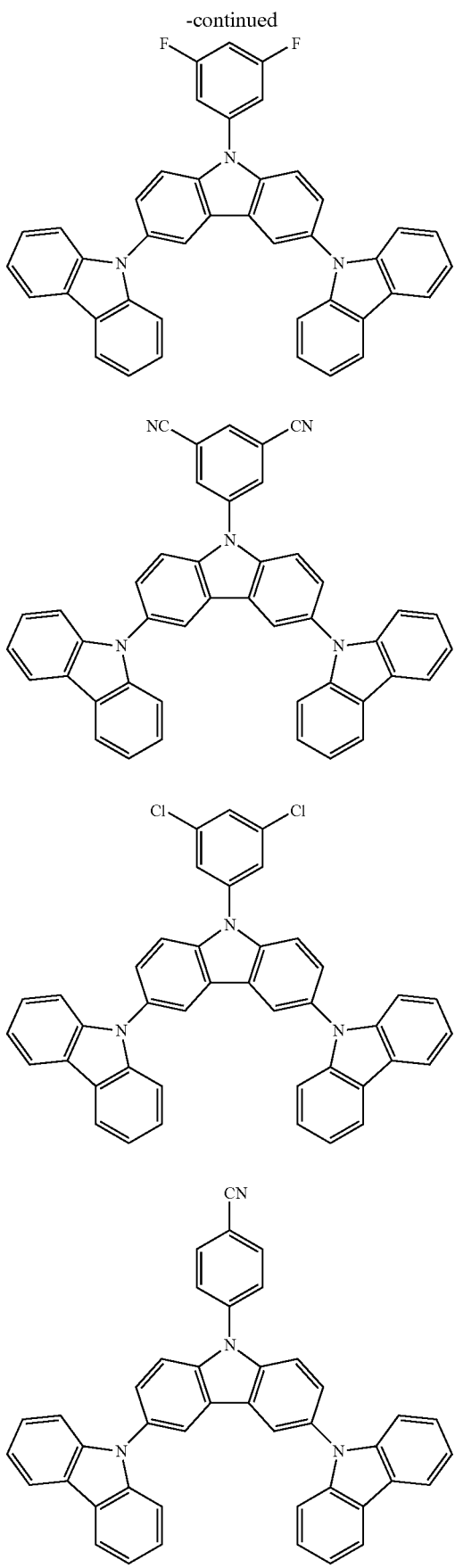
116
-continued
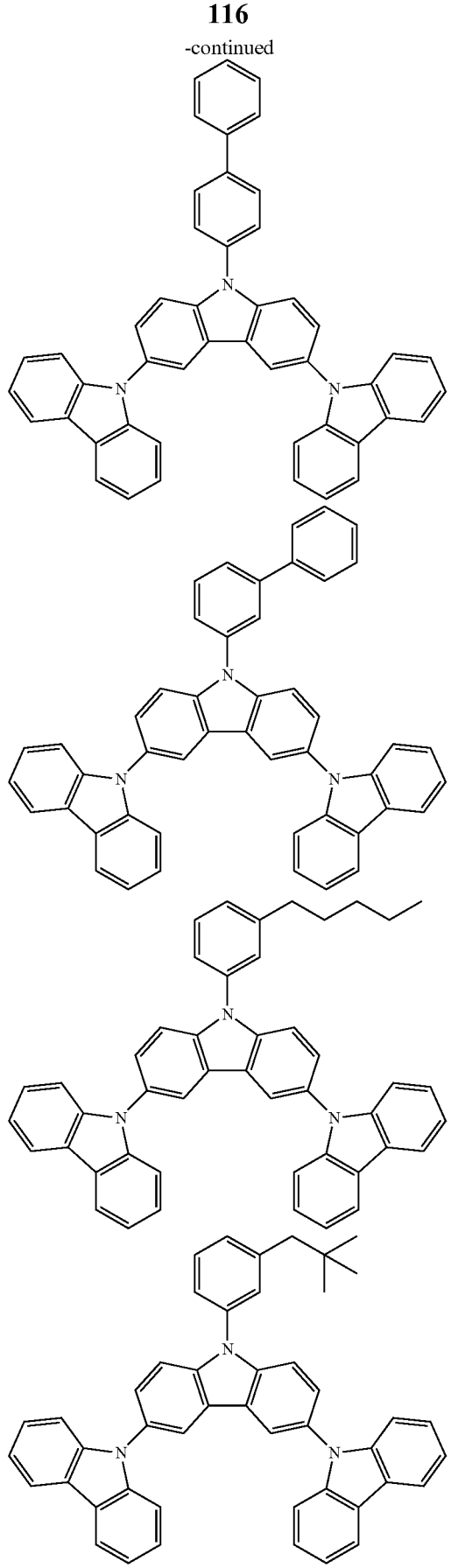

117
-continued
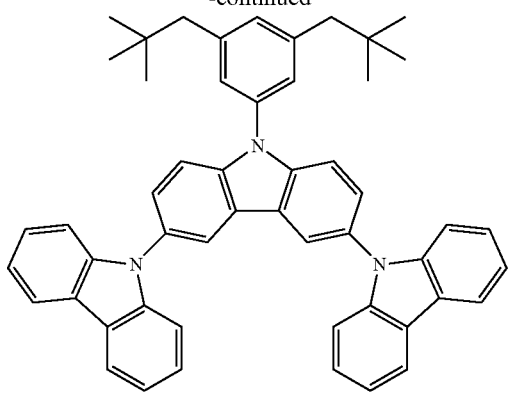
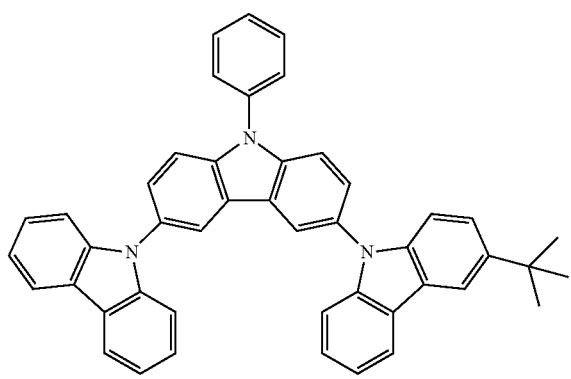
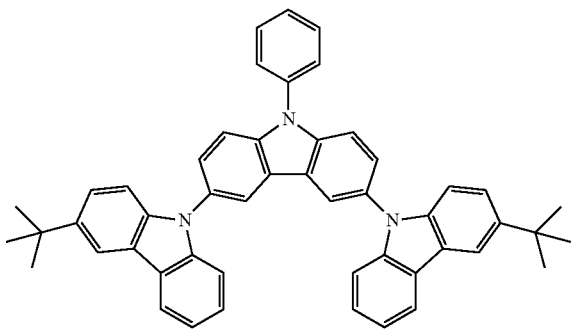
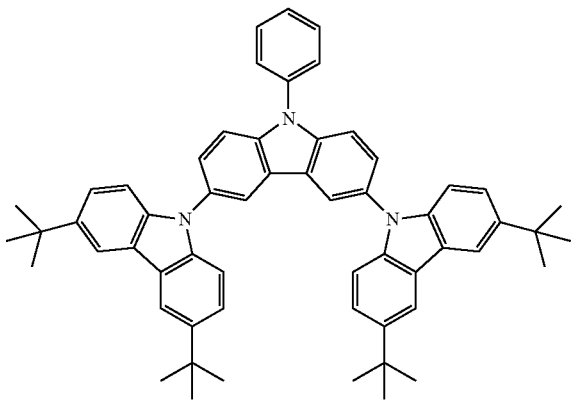
118
-continued
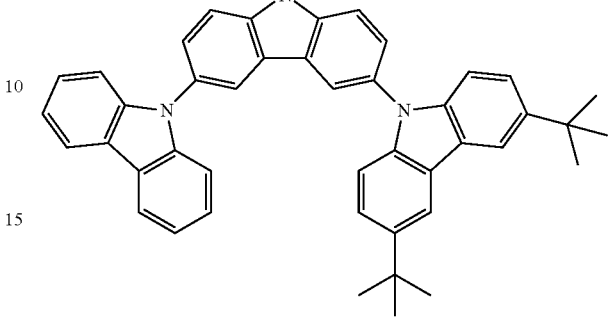
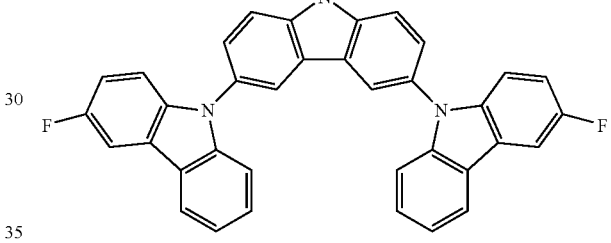
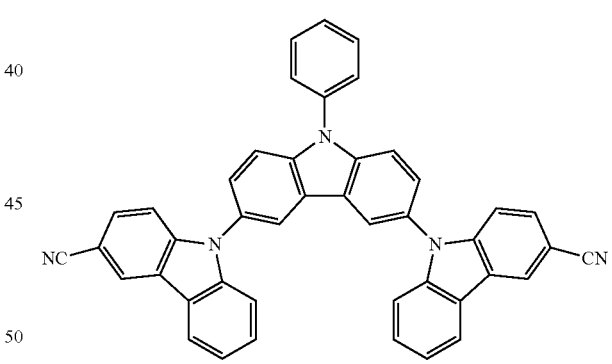
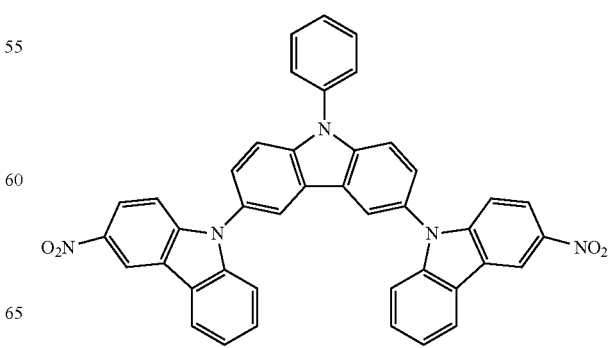

119
-continued
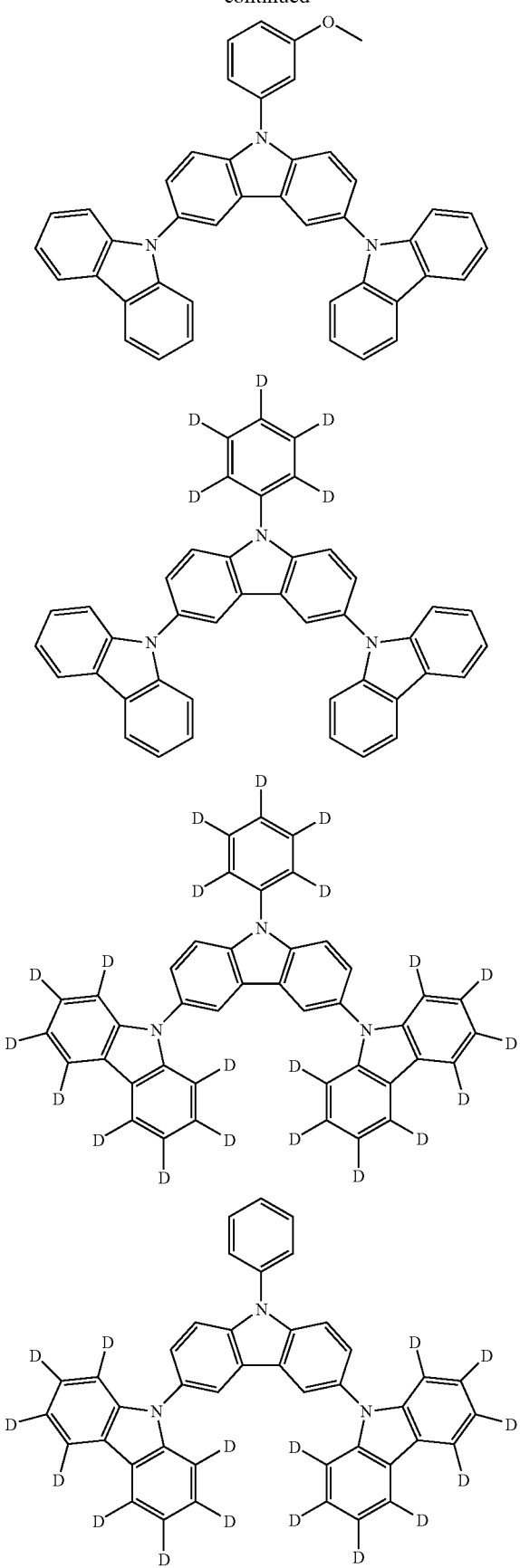
120
-continued
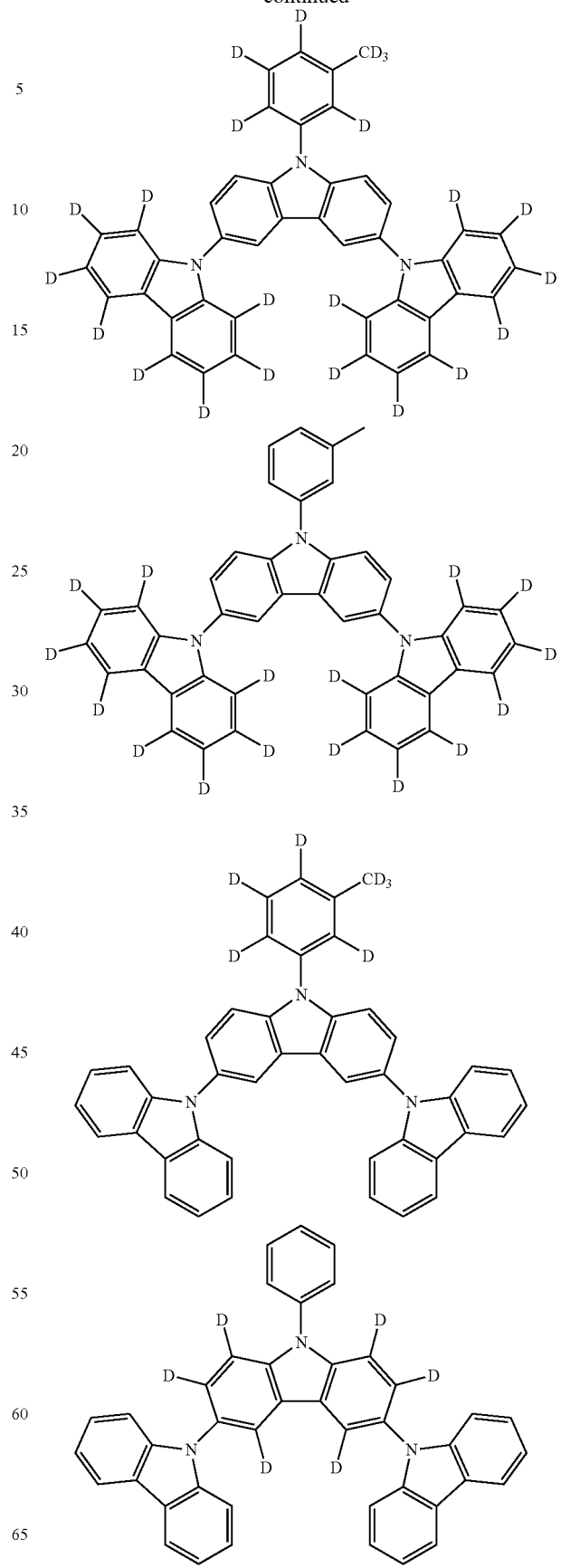

The thickness of the hole injection layer or hole transport layer is preferably 500 nm or less from the standpoint of reducing a drive voltage.

The thickness of the hole transport layer is preferably from 1 nm to 500 nm, more preferably from 5 nm to 200 nm, still more preferably from 5 nm to 100 nm. The thickness of the hole injection layer is preferably from 0.1 nm to 500 nm, more preferably from 0.5 nm to 300 nm, still more preferably from 1 nm to 200 nm.

The hole injection layer and the hole transport layer each may have a single layer structure comprised of one or more of the above-described materials or a multilayer structure comprised of two or more layers having the same composition or different compositions.

—Electron Injection Layer, Electron Transport Layer—

The electron injection layer and electron transport layer are layers having a function of accepting electrons from a cathode or cathode side and transporting them to an anode side. Specific examples of a material which the electron injection layer or electron transport layer contains therein include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic ring tetracarboxylic anhydrides such as naphthalene tetracarboxylic anhydride and perylene tetracarboxylic anhydride, phthalocyanine derivatives, phenanthrene derivatives, phenanthroline derivatives, various complexes typified by complexes of a 8-quinolinol derivative, metal phthalocyanine, and complexes having benzoxazole or benzothiazole as a ligand, and organosilane derivatives.

The thickness of the electron injection layer or electron transport layer is preferably 100 nm or less from the standpoint of reducing a drive voltage.

The thickness of the electron transport layer is preferably from 1 nm to 100 nm, more preferably from 5 nm to 50 nm, still more preferably from 10 nm to 30 nm. The thickness of the electron injection layer is preferably from 0.1 nm to 100 nm, more preferably from 0.2 nm to 80 nm, still more preferably from 0.5 nm to 50 nm.

The electron injection layer and the electron transport layer each may have a single layer structure comprised of one or more of the above-described materials or a multilayer structure comprised of two or more layers having the same composition or different compositions.

—Hole Blocking Layer—

The hole blocking layer is a layer having a function of preventing holes, which have been transported from the anode side to the light emitting layer, from passing through to the cathode side. In the invention, the hole blocking layer can be provided as an organic layer adjacent to the light emitting layer on the cathode side.

Examples of an organic compound constituting the hole blocking layer include aluminum complexes such as aluminum(III) bis(2-methyl-8-quinolinato)-4-phenylphenolate (which will hereinafter be abbreviated as "BAlq"), carbazole derivatives, triazole derivatives, and phenanthroline derivatives such as 2,9-dimethyl-4,7-diphenyl-1,10-phenanthroline (which will hereinafter be abbreviated as "BCP").

The thickness of the hole blocking layer is preferably from 1 nm to 500 nm, more preferably from 5 nm to 200 nm, still more preferably from 10 nm to 100 nm.

The hole blocking layer may have a single layer structure comprised of one or more of the above-described materials or a multilayer structure comprised of two or more layers having the same composition or different compositions.

—Electron Blocking Layer—

The electron blocking layer is a layer having a function of preventing electrons, which have been transported from the cathode side to the light emitting layer, from passing through to the anode side. In the invention, the electron blocking layer can be provided as an organic layer adjacent to the light emitting layer on the anode side.

Examples of an organic compound constituting the electron blocking layer include those exemplified above as the hole transport material.

The thickness of the electron blocking layer is preferably from 1 nm to 500 nm, more preferably from 5 nm to 200 nm, still more preferably from 10 nm to 100 nm.

The electron blocking layer may have a single layer structure comprised of one or more of the above-described materials or a multilayer structure comprised of two or more layers having the same composition or different compositions.

<Protective Layer>

In the invention, the entirety of the organic EL device may be protected with a protective layer.

Materials contained in the protective layer are not limited insofar as they have a function of preventing substances such as water and oxygen, which promote deterioration of the device, from entering the device.

Specific examples include metals such as In, Sn, Pb, Au, Cu, Ag, Al, Ti, and Ni, metal oxides such as MgO, SiO, $SiO_2$, $Al_2O_3$, GeO, NiO, CaO, BaO, $Fe_2O_3$, $Y_2O_3$, and $TiO_2$, metal nitrides such as $SiN_x$ and $SiN_xO_y$, metal fluorides such as $MgF_2$, LiF, $AlF_3$, and $CaF_2$, polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, copolymers available by copolymerizing a mixture of tetrafluoroethylene and at least one comonomer, fluorine-containing copolymers having, in the main chain thereof, a cyclic structure, water-absorbing substances having a water absorption rate of 1% or greater, and moisture-proof substances having a water absorption rate of 0.1% or less.

Although the formation process of the protective layer is not particularly limited, vacuum deposition, sputtering, reactive sputtering, MBE (molecular beam epitaxy, cluster ion beam, ion plating, plasma polymerization (high frequency excitation ion plating), plasma CVD, laser CVD, heat CVD, gas source CVD, coating process, printing process, or transfer process can be employed for the formation.

(Sealing Container)

The whole device of the invention may be sealed with a sealing container. A moisture absorbent or an inert liquid may be sealed in a space between the sealing container and the device. Although the moisture absorbent is not particularly limited, examples include barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieves, zeolite, and magnesium oxide. Although the inert liquid is not particularly limited, examples include paraffins, liquid paraffins, fluorine-based solvents such as perfluoroalkane, perfluoroamine, and perfluoroether, chlorine-based solvents, and silicone oils.

The device of the invention can emit light by applying thereto a direct current (alternating current components may be contained as needed) voltage (usually from 2 volts to 15 volts) or direct current between the anode and the cathode.

As the driving method of the device of the invention, driving methods described in Japanese Patent Laid-Open Nos. 148687/1990, 301355/1994, 29080/1993, 134558/1995, 234685/1996, and 241047/1996, Japanese Patent No. 2784615, U.S. Pat. Nos. 5,828,429 and 6,023,308 and the like can be employed.

The device of the invention is suited for use in display devices, displays, backlights, electron photographs, light sources for illumination, recording, exposure, or reading, signs, signboards, interiors, optical communications, and the like.

The light emitting apparatus of the invention will next be described referring to FIG. 2.

The light emitting apparatus of the invention comprises the organic electroluminescent device.

Figure 2:
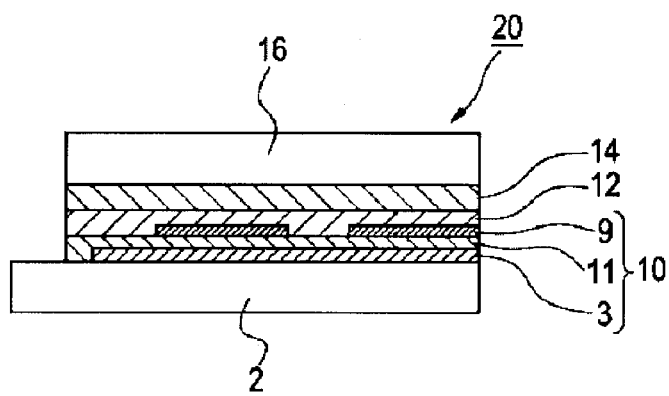
FIG. 2 is a schematic cross-sectional view illustrating an exemplary embodiment of a light emitting apparatus of the invention.

FIG. 2 is a schematic cross-sectional view illustrating one example of the light emitting apparatus of the invention.

A light emitting apparatus 20 of FIG. 2 has a transparent substrate (support substrate) 2, an organic electroluminescent device 10, a sealing container 16, and the like. The organic electroluminescent device 10 is formed by successively stacking, over the substrate 2, an anode (first electrode) 3, an organic layer 11, a cathode (second electrode) 9. Over the cathode 9, a protective layer 12 is stacked and the protective layer 12 has thereon the sealing container 16 via an adhesion layer 14. It is to be noted that a part of each of the electrode 3 and 9, a partition, insulating layer, and the like are omitted.

As the adhesion layer 14, a photosetting adhesive or thermosetting adhesive can be used. For example, a thermosetting adhesion sheet can also be used.

The intended use of the light emitting apparatus of the invention is not particularly limited and it can be used, for example, for illumination apparatuses and display apparatuses such as TV, personal computer, mobile phone, and electronic paper.

The illumination apparatus of the invention will next be described referring to FIG. 3.

Figure 3:
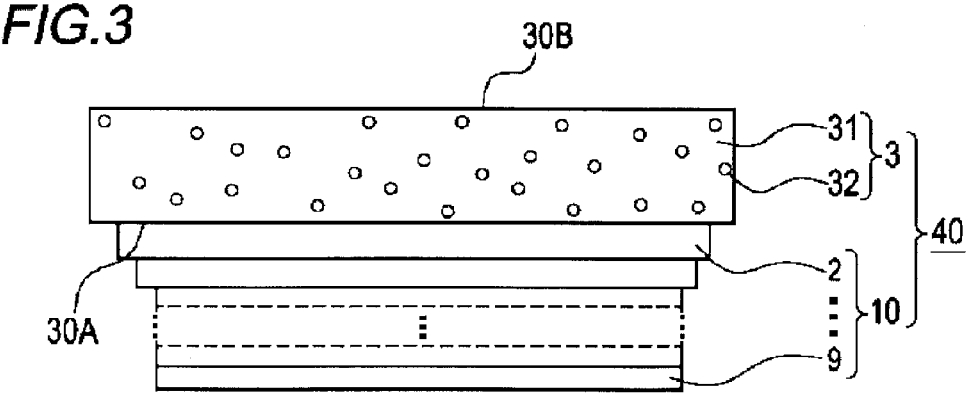
FIG. 3 is a schematic cross-sectional view illustrating an exemplary embodiment of an illumination apparatus of the invention.

FIG. 3 is a schematic cross-sectional view illustrating one example of the illumination apparatus of the invention.

An illumination apparatus 40 is equipped with the above-described organic electroluminescent device 10 and a light scattering member 30. More specifically, in the illumination apparatus 40, the substrate 2 of the organic electroluminescent device 10 is brought into contact with the light scattering member 30.

The light scattering member 30 is not particularly limited insofar as it can scatter light. In FIG. 3, it is a member obtained by dispersing fine particles 32 in a transparent substrate 31. As the transparent substrate 31, for example, a glass substrate can be used. As the fine particles 32, transparent resin fine particles are preferably employed. As each of the glass substrate and transparent resin fine particles, known ones can be used. In such an illumination apparatus 40, when light from the organic electroluminescent device 10 is incident on a light incidence plane 30A of the light scattering member 30, the light scattering member scatters the incident light and the scattered light is emitted as an illumination light from the light emission plane 30B.

The present invention will hereinafter be described in further detail by Examples, but the scope of the invention is not limited by the following specific examples.

Synthesis Example 1

The following Exemplified compound 1 was synthesized.

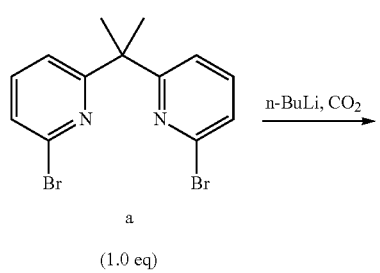

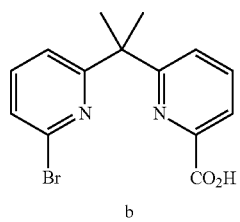

A THF solution of Compound a (20.0 g, 56.2 mmol, 1.0 equivalent) was cooled to −78° C. in a nitrogen atmosphere and while stirring, the resulting solution was added dropwise to butyllithium (36.9 mL, 59.0 mmol, 1.05 equivalents) gradually. After stirring for 30 minutes as was, the resulting mixture was raised to room temperature while feeding the mixture with a carbon dioxide gas that was caused to pass through a calcium chloride tube. Then, a saturated aqueous solution of ammonium chloride was added to the reaction mixture, followed by extraction with ethyl acetate. The organic phases were combined, dried, and concentrated. The residue thus obtained was purified by a silica gel column to obtain 6.99 g (yield: 82%) of Compound b as a mixture with the raw materials.

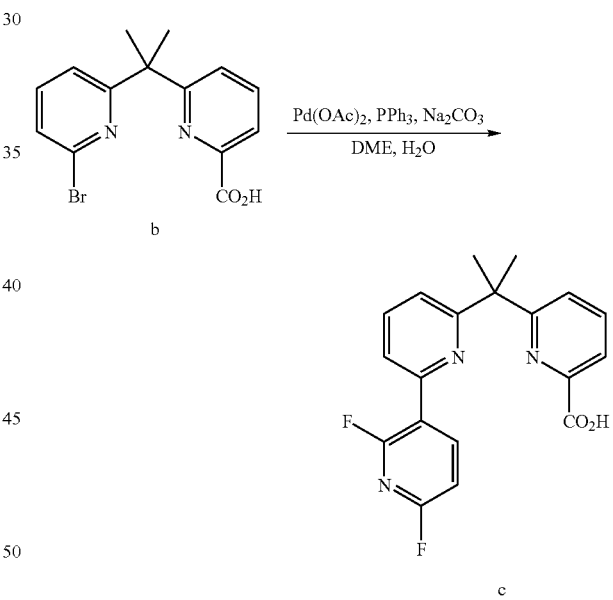

A mixture composed of Compound b (7.2 g, 8.6 mmol, 1.0 equivalent), 2,6-difluoropyridyl-3-boric acid (5.3 g, 33.6 mmol, 1.5 equivalents), palladium acetate (126 mg, 0.56 mmol, 5.0 mol %), triphenylphosphine (590 mg, 2.2 mmol, 0.2 equivalent), sodium carbonate (19.0 g, 179 mmol, 8.0 equivalents), dimethoxyethane (70.0 mL), and water (70.0 mL) was stirred at 80° C. for 4.5 hours in a nitrogen atmosphere. The reaction mixture was cooled to room temperature and filtered, followed by extraction with ethyl acetate. The organic phases were combined, dried, and concentrated. The residue thus obtained was purified by a column to obtain 7.1 g (100%) of Compound c as a colorless oil.

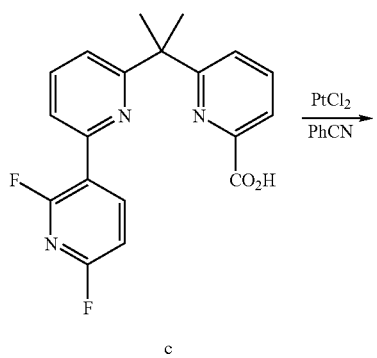

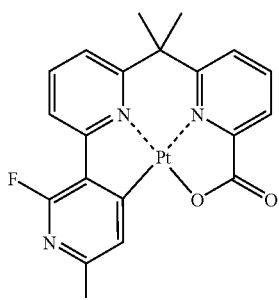

Exemplified compound 1

Platinum dichloride (5.3 g, 19.8 mmol, 1.0 equivalent) and Compound c (7.0 g, 19.8 mmol, 1.0 equivalent) were stirred for 4.5 hours in benzonitrile (120 mL) in a nitrogen atmosphere under heating and refluxing conditions. The reaction mixture was allowed to cool to room temperature. The solid thus precipitated was collected by filtration and washed with methanol to obtain 5.2 g of a platinum complex (Exemplified compound 1) as a yellow powder. Yield: 48%.

$^1$H-NMR (400 MHz, CD$_2$Cl$_2$): δ 1.96(s,6H), 7.02(s,J(Pt—H)=52.0 Hz,1H), 7.45(dd,J=2.8,9.2 Hz,1H), 7.95-7.83(m, 4H), 8.10(t,J=9.0 Hz,1H).

(ESI-MS C$_{19}$H$_{13}$O$_2$N$_3$F$_2$Pt; Calculated: 549.07 (M+H$^+$); found: 549.00 (M+H$^+$))

In a similar manner to that described above, Exemplified compounds 6-22 and Comparative compound ref-2 and ref-7 were synthesized. The followings are NMR data of Exemplified compounds 8-9, 11, 13-17, and 19.

Exemplified Compound 8

$^1$H-NMR (400 MHz, CD$_2$Cl$_2$) δ: 1.92(s,6H), 2.41(s,3H), 2.45(s,3H), 7.01(s,J(Pt—H)=52.0 Hz,1H), 7.25(s,1H), 7.61 (d,J=14.4 Hz,1H), 7.73(s,1H), 7.74(d,J=14.4 Hz,1H).

(ESI-MS C$_{21}$H$_{17}$O$_2$N$_3$F$_2$Pt; Calculated: 577.10 (M+H$^+$); Found: 577.11 (M+H$^+$))

Exemplified Compound 9

$^1$H-NMR (400 MHz, CD$_2$Cl$_2$) δ: 1.95(s,6H), 7.04(s,1H), 7.25(dd,J=2.1,6.9 Hz,1H), 7.65(d,J=6.3 Hz,1H), 7.84(d, J=6.3 Hz,1H), 7.95(d,J=5.7 Hz,1H), 8.11(t,J=6.0 Hz,1H).

(ESI-MS C$_{19}$H$_{11}$O$_2$N$_3$F$_3$Pt; Calculated: 567.06 (M+H$^+$); Found: 566.99 (M+H$^+$))

Exemplified Compound 11

$^1$H-NMR (400 MHz, CD$_2$Cl$_2$) δ: 1.96(s,6H), 7.03(s,1H), 7.44(m,1H), 7.60(d,J=6.9 Hz,1H), 7.68(d,J=5.4 Hz,1H), 7.94 (m,2H).

(ESI-MS C$_{19}$H$_{11}$O$_2$N$_3$F$_3$Pt; Calculated: 567.06 (M+H$^+$); Found: 567.12 (M+H$^+$))

Exemplified Compound 13

$^1$H-NMR (400 MHz, CD$_2$Cl$_2$) δ: 1.90(s,6H), 2.01(m,8H), 3.39(m,8H), 6.45(s,1H), 6.63(s,1H), 6.96(m,3H).

(ESI-MS C$_{27}$H$_{27}$O$_2$N$_5$F$_2$Pt; Calculated: 687.19 (M+H$^+$); Found: 687.19 (M+H$^+$))

Exemplified Compound 14

$^1$H-NMR (400 MHz, CD$_2$Cl$_2$) δ: 1.90(s,6H), 2.04(m,4H), 3.42(m,4H), 6.44(s,1H), 6.92(m,2H), 7.52(d,J=9.3 Hz,1H), 7.63(d,J=7.2 Hz,1H).

(ESI-MS C$_{23}$H$_{19}$O$_2$N$_4$F$_3$Pt; Calculated: 636.12 (M+H$^+$); Found: 636.13 (M+H$^+$))

Exemplified Compound 15

$^1$H-NMR (400 MHz, CD$_2$Cl$_2$) δ: 1.43(m,6H), 2.79(m,4H), 7.08(s,1H), 7.25(d,J=7.8 Hz,1H), 8.06-7.92(m,4H), 8.20(t, J=7.8 Hz,1H).

(ESI-MS C$_{22}$H$_{19}$O$_2$N$_3$F$_2$Pt; Calculated: 589.10(M+H$^+$); Found: 589.11 (M+H$^+$))

Exemplified Compound 16

$^1$H-NMR (400 MHz, CD$_2$Cl$_2$) δ: 0.42(d,J=12.6 Hz,6H), 0.44(s,J=12.6 Hz,6H), 1.08(sep, J=6.6 Hz,2H), 2.32(t,J=6.9 Hz,4H), 7.14(s,J(Pt—H)=51.0 Hz,1H), 7.61(m,1H), 8.00-7.93(m,4H), 8.15(t,J=7.8 Hz,1H).

(ESI-MS C$_{25}$H$_{25}$O$_2$N$_3$F$_2$Pt; Calculated: 633.16 (M+H$^+$); Found: 633.14 (M+H$^+$)

Exemplified Compound 17

$^1$H-NMR (400 MHz, CD$_2$Cl$_2$) δ: 1.49(s,18H), 6.42(d, J=7.2 Hz,1H), 6.69(d,J=7.2 Hz,1H), 6.72(s,1H), 7.33(t,J=6.3 Hz,1H), 7.48(d,J=5.8 Hz,1H), 7.65(m,3H), 7.83(m,2H).

(ESI-MS C$_{30}$H$_{28}$O$_2$N$_4$F$_2$Pt; Calculated: 710.19 (M+H$^+$); Found: 710.20 (M+H$^+$)

Exemplified Compound 19

$^1$H-NMR (400 MHz, CD$_2$Cl$_2$) δ: 6.53(m,4H), 6.85(d,J=7.2 Hz,1H), 6.92(s,1H), 7.34-7.18(m,8H), 7.79(t,J=8.0 Hz,1H), 8.00-7.94(m,2H).

(ESI-MS C$_{29}$H$_{17}$O$_2$N$_3$F$_2$Pt; Calculated: 673.10 (M+H$^+$); Found: 673.10 (M+H$^+$))

Synthesis Example 2

The following Exemplified compound 2 was synthesized.

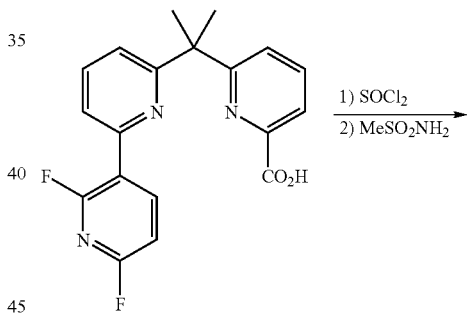

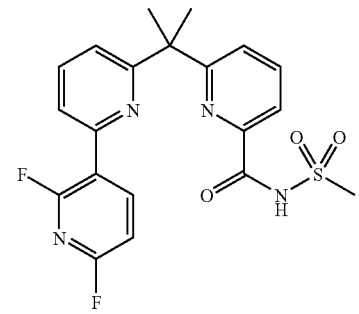

Compound c (1.0 g, 2.5 mmol, 1.0 equivalent) was dissolved in thionyl chloride (10 mL) and the resulting solution was heated and refluxed for 1.5 hours. After the reaction mixture was allowed to cool, the thionyl chloride was distilled off. The residue thus obtained was dissolved in methylene chloride (10 mL), followed by cooling to 0° C. Methanesulfonylamine (285 mg, 3.0 mmol, 1.2 equivalents) was added in portions to the resulting solution and the mixture was raised to room temperature. Water was added to the reaction mixture, followed by extraction with ethyl acetate. The organic phases were combined, dried, and concentrated. The residue thus obtained was purified by a column to obtain 980 mg (90%) of Compound d as a viscous liquid.

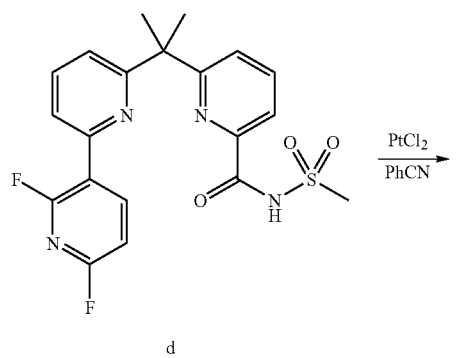

d

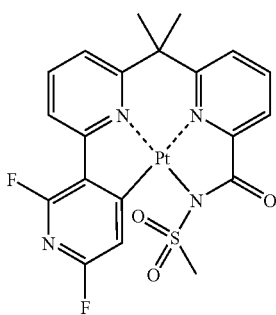

Exemplified compound 2

Platinum dichloride (325 mg, 1.22 mmol, 1.0 equivalent) and Compound d (530 mg, 1.22 mmol, 1.0 equivalent) were stirred in benzonitrile (10 mL) for 1.5 hours in a nitrogen atmosphere under heating and reflux conditions. The reaction mixture was allowed to cool to room temperature. The solid thus precipitated was collected by filtration and washed with methanol to obtain 530 mg of a platinum complex (Exemplified compound 2) as a yellow powder. Yield: 70%.

$^1$H-NMR (300 MHz, CD$_2$Cl$_2$) δ: 1.22(br,2H), 1.47(br,2H), 1.92(br,2H), 2.61(br,2H), 2.99(br,2H), 7.48(m,J(Pt—H)=60.0 Hz,2H), 7.56-7.53(m,2H), 7.95(t,J=9.0 Hz,2H), 8.08(d,J=9.0 Hz,2H).

(ESI-MS C$_{20}$H$_{16}$O$_3$S$_1$N$_4$F$_2$Pt; Calculated: 626.06 (M+H$^+$); Found: 626.05 (M+H$^+$))

Synthesis Example 3

The following Exemplified compound 3 was synthesized.

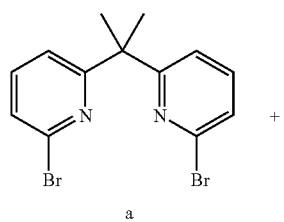

a

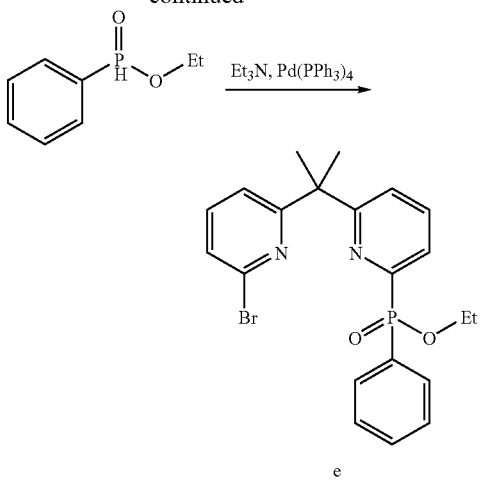

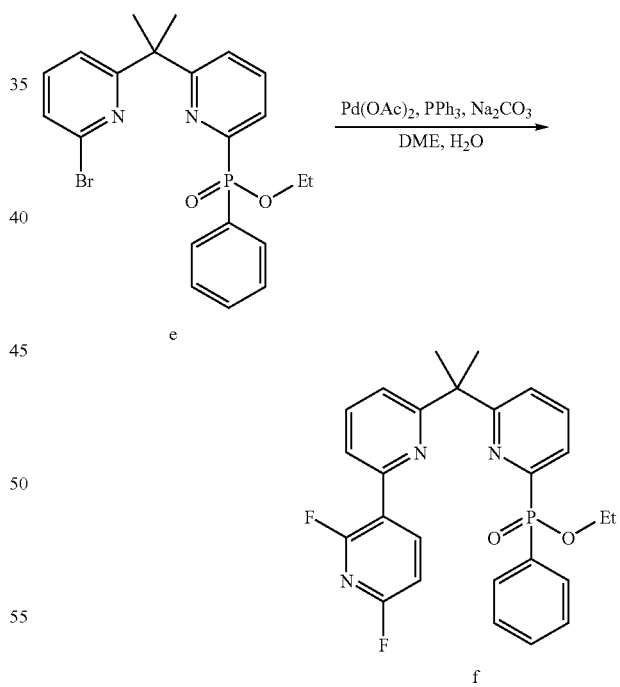

A triethylamine solution (10 mL) of Compound a (6.0 g, 16.8 mmol, 1.0 equivalent), ethyl phenyl hypophosphite (2.6 mL, 16.8 mmol, 1.0 equivalent), and tetrakistriphenylphosphine palladium (970 mg, 0.84 mmol, 0.05 equivalent) was heated for 1.5 hours at 100° C. After the reaction mixture was allowed to cool, a saturated aqueous solution of ammonium chloride was added to the reaction mixture, followed by extraction with ethyl acetate. The organic phases were combined, dried, and concentrated. The residue thus obtained was purified by a column to obtain 4.0 g (53%) of Compound e as a viscous liquid.

A mixture composed of Compound e (3.8 g, 8.5 mmol, 1.0 equivalent), 2,6-difluoropyridyl-3-boric acid (2.0 g, 12.8 mmol, 1.5 equivalents), palladium acetate (95 mg, 0.42 mmol, 5.0 mol %), triphenylphosphine (445 mg, 1.7 mmol, 0.2 equivalent), sodium carbonate (4.5 g, 43.0 mmol, 5.0 equivalents), dimethoxyethane (70.0 mL), and water (70.0 mL) was stirred at 80° C. for 4.5 hours in a nitrogen atmosphere. The reaction mixture was cooled to room temperature and filtered, followed by extraction with ethyl acetate. The organic phases were combined, dried, concentrated. The residue thus obtained was purified by a column to obtain 3.1 g (76%) of Compound f as a colorless oil.

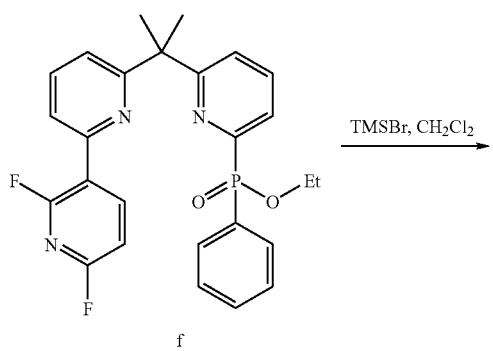

f

Bromotrimethylsilane was added dropwise to a dichloromethane solution (50 mL) of Compound f (3.0 g, 6.3 mmol, 1.0 equivalent) and the resulting mixture was stirred for 10 hours as was. The reaction mixture was extracted with ethyl acetate. The organic phases were combined, dried, and concentrated to obtain 2.5 (87%) of Compound g as a colorless oil.

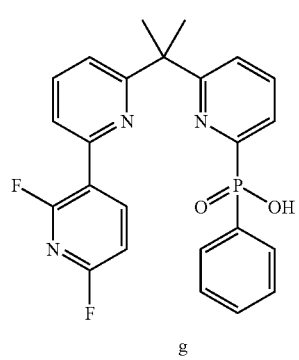

g

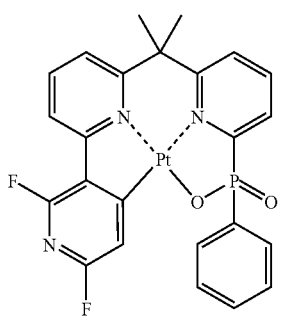

g

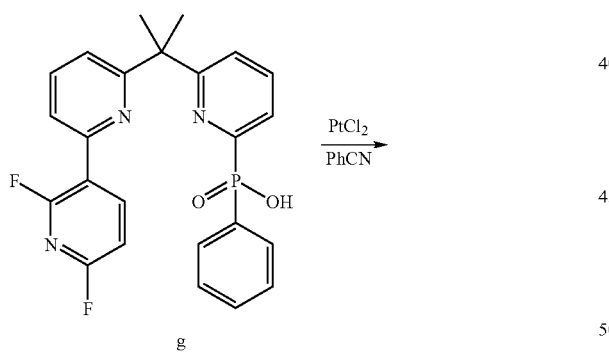

Exemplified compound 3

Platinum dichloride (1.5 g, 5.5 mmol, 1.0 equivalent) and Compound g (2.5 g, 5.5 mmol, 1.0 equivalent) were stirred for 3 hours in benzonitrile (150 mL) in a nitrogen atmosphere under heating and refluxing conditions. The reaction mixture was allowed to cool to room temperature. The solid thus precipitated was collected by filtration and purified by a column to obtain 850 mg of a platinum complex (Exemplified compound 3) as a yellow powder. Yield: 53%.

$^1$H-NMR (300 MHz, $CD_2Cl_2$) δ: 2.13(s,6H), 7.22(br-s,J (Pt—H)=39.0 Hz,1H), 7.41-7.35(m,2H), 7.54-7.44(m,2H), 7.84-7.80(m,2H), 8.08-8.01(m,5H).

(ESI-MS $C_{24}H_{18}O_2P_1N_3F_2Pt$; Calculated: 645.08 $(M+H^+)$; Found: 645.10 $(M+H^+)$)

In a similar manner to that described above, the following Exemplified compounds 4 and 5 were synthesized. In addition, the following Comparative compounds ref-1 and ref-3 to ref-6 and Ir(ppy)$_3$ were prepared.

With respect to the compounds represented by the formula (I) but other than those described above, various compounds represented by the formula (I) can be synthesized by using aromatic boric acids represented by the following formulae or esters thereof instead of the 2,6-difluoropyridylboric acid in Synthesis Examples 1 or 3.

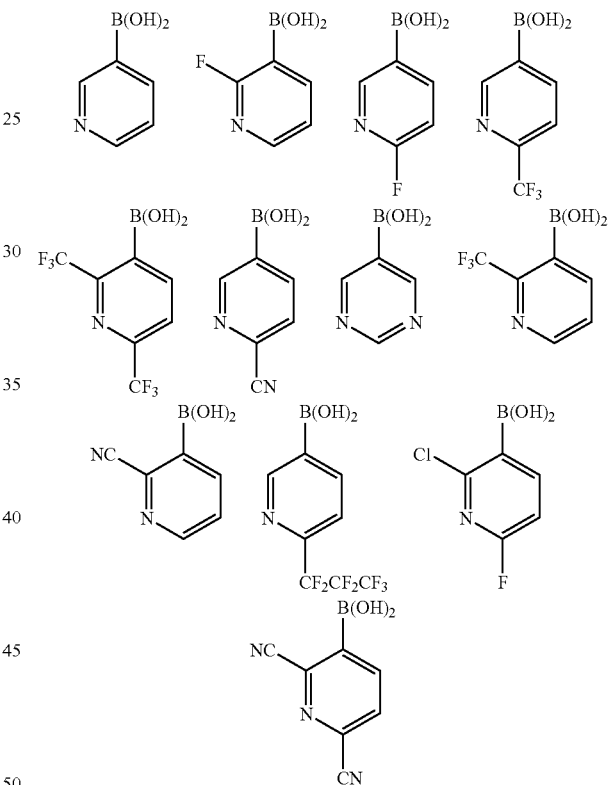

EXAMPLES

Fabrication of Comparative device 1-1

A glass substrate (product of Geomatec having a surface resistivity of 10 Ω/☐) 0.5 mm thick and 2.5 cm square and having an ITO film thereon was put in a cleaning container, ultrasonically cleaned in 2-propanol, and subjected to UV ozone treatment for 30 minutes. On the resulting transparent anode (ITO film), the following organic layers were deposited successively by vacuum deposition.

First layer: DNTPD, film thickness: 160 nm
Second layer: NPD, film thickness: 10 nm
Third layer: H-1 and ref-1 (mass ratio 85:15), film thickness: 60 nm Fourth layer: BAlq, film thickness: 10 nm
Fifth layer: BCP and 1% Li, film thickness: 20 nm On the fifth layer, 1.0 nm of lithium fluoride and 100 nm of metal aluminum were deposited in the order of mention to form a cathode.

Without bringing the resulting product into contact with the atmosphere, it was put in a glove box purged with an argon gas and sealed with a UV-curing adhesive ("XNR5516HV", product of Nagase Ciba) in a stainless-steel sealing can to obtain Comparative device 1-1.

(Fabrication of Invention Devices 1-1 to 1-12, 2-1 to 2-8, 3-1 to 3-5, 4-1 to 4-3, 5-1 to 5-4, and 6-1 to 6-10, and Comparative Devices 1-2 to 1-7, 2-1, 3-1 to 3-2, 4-1 to 4-3, 5-1 to 5-3, and 6-1 to 6-3)

The above-described devices were fabricated in a similar manner to that employed for Comparative device 1-1 except the materials constituting the third layer were changed to Material 1 and Material 2 as listed in the following Table 1. In Table 1, a ratio of Material 1 to Material 2 is 85:15 (mass ratio). The numeral in Material 2 corresponds to a numeral given to Exemplified compound (which will apply similarly to the numeral in each table).

Devices thus obtained were each tested for maximum emission wavelength and drive voltage. In each example, they were measured in the following manners.

(a) Emission Wavelength/Emission Spectrum and CIE Chromaticity

Direct current voltage was applied to each device to make it to emit light by using "Source Measure Unit 2400" manufactured by Toyo Corporation. The luminance of the light was measured using "Luminance Meter BM-8" manufactured by Topcon Corporation. The emission spectrum and emission wavelength were measured using "Spectral Analyzer PMA-11", manufactured by Hamamatsu Photonics.

On the other hand, CIE chromaticity coordinates xy were calculated from the emission spectrum thus measured.

(b) Drive Voltage

Direct current voltage was applied to each device to give its luminance of 360 cd/m² to make it to emit light. The voltage applied at that time was used as an indicator of evaluating a drive voltage.

The results are shown in Table 1. In this table, the drive voltage is expressed as a relative value to the drive voltage of Invention device 1-1 set to 100.

TABLE 1

| No. of Example | Material 1 | Material 2 | Maximum emission wavelength (nm) | Voltage 360 cd/m², relative value |
|---|---|---|---|---|
| Invention device 1-1 | H-1 | 1 | 467 | 100 |
| Invention device 1-2 | H-1 | 2 | 462 | 98 |
| Invention device 1-3 | H-1 | 3 | 468 | 101 |
| Invention device 1-4 | H-1 | 5 | 461 | 102 |
| Invention device 1-5 | H-1 | 6 | 513 | 94 |
| Invention device 1-6 | H-1 | 7 | 477 | 91 |
| Invention device 1-7 | H-1 | 11 | 461 | 105 |
| Invention device 1-8 | H-1 | 14 | 460 | 95 |
| Invention device 1-9 | H-1 | 15 | 467 | 101 |
| Invention device 1-10 | H-1 | 16 | 464 | 99 |
| Invention device 1-11 | H-1 | 20 | 482 | 86 |
| Invention device 1-12 | H-2 | 21 | 480 | 89 |
| Comparative device 1-1 | H-1 | ref-1 | 478 | 161 |
| Comparative device 1-2 | H-1 | ref-2 | 482 | 148 |
| Comparative device 1-3 | H-1 | ref-3 | 467 | 152 |
| Comparative device 1-4 | H-1 | ref-4 | 482 | 130 |
| Comparative device 1-5 | H-1 | ref-5 | 600 | 183 |
| Comparative device 1-6 | H-1 | Ir(ppy)$_3$ | 514 | 170 |
| Comparative device 1-7 | H-1 | ref-6 | 469 | 168 |
| Invention device 2-1 | H-2 | 2 | 462 | 95 |
| Invention device 2-2 | H-2 | 4 | 461 | 99 |
| Invention device 2-3 | H-2 | 5 | 460 | 99 |
| Invention device 2-4 | H-2 | 8 | 465 | 102 |
| Invention device 2-5 | H-2 | 12 | 466 | 92 |
| Invention device 2-6 | H-2 | 13 | 458 | 87 |
| Invention device 2-7 | H-2 | 17 | 465 | 90 |
| Invention device 2-8 | H-2 | 19 | 473 | 102 |
| Comparative device 2-1 | H-2 | ref-2 | 482 | 145 |
| Invention device 3-1 | H-3 | 3 | 469 | 98 |
| Invention device 3-2 | H-3 | 8 | 464 | 102 |
| Invention device 3-3 | H-3 | 9 | 451 | 93 |
| Invention device 3-4 | H-3 | 10 | 448 | 104 |
| Invention device 3-5 | H-3 | 22 | 475 | 91 |
| Comparative device 3-1 | H-3 | ref-3 | 467 | 148 |
| Comparative device 3-2 | H-3 | ref-1 | 478 | 159 |
| Invention device 4-1 | H-4 | 4 | 460 | 114 |
| Invention device 4-2 | H-4 | 9 | 451 | 107 |
| Invention device 4-3 | H-4 | 18 | 470 | 104 |
| Comparative device 4-1 | H-4 | ref-3 | 467 | 170 |
| Comparative device 4-2 | H-4 | ref-5 | 599 | 201 |
| Invention device 5-1 | H-5 | 7 | 477 | 100 |
| Invention device 5-2 | H-5 | 10 | 450 | 113 |
| Invention device 5-3 | H-5 | 20 | 478 | 90 |
| Invention device 5-4 | H-5 | 22 | 472 | 95 |
| Comparative device 5-1 | H-5 | ref-2 | 484 | 155 |
| Comparative device 5-2 | H-5 | ref-4 | 482 | 135 |
| Comparative device 5-3 | H-5 | Ir(ppy)$_3$ | 515 | 177 |
| Invention device 6-1 | H-7 | 1 | 467 | 104 |
| Invention device 6-2 | H-7 | 10 | 449 | 108 |
| Comparative device 6-1 | H-7 | ref-1 | 477 | 165 |
| Comparative device 6-2 | H-7 | ref-6 | 468 | 172 |
| Comparative device 6-3 | H-7 | ref-7 | 458 | 174 |
| Invention device 6-3 | H-8 | 1 | 467 | 101 |
| Invention device 6-4 | H-9 | 1 | 466 | 99 |
| Invention device 6-5 | H-10 | 1 | 466 | 98 |
| Invention device 6-6 | H-11 | 1 | 467 | 100 |
| Invention device 6-7 | H-8 | 10 | 449 | 103 |
| Invention device 6-8 | H-9 | 10 | 450 | 101 |
| Invention device 6-9 | H-10 | 10 | 450 | 100 |
| Invention device 6-10 | H-11 | 10 | 449 | 101 |

The results of Table 1 show that the invention devices can be driven at a lower voltage than that of the comparative devices having a similar maximum emission wavelength.

As can be found from the comparison between Invention devices 6-1 and 6-2 and Invention devices 6-3 to 6-10, the devices can be driven at a lower voltage by using the material represented by the formula (4-1) or (4-2) as the material of the light emitting layer.

(Fabrication of Invention Devices 7-1 to 7-9 and Comparative Devices 7-1 to 7-9)

In a similar manner to that employed for Comparative device 1-1 except that the materials of the first to fourth layers were changed to those listed in the following Table 2, devices were fabricated.

The drive voltage of each of the resulting devices was measured in a similar manner to that described above.

In Table 2, a ratio of the materials of the third layer was indicated as mass ratio in parentheses. The results are shown in Table 2. The drive voltage indicated in this table is a value relative to that of Invention device 7-1 set to 100.

TABLE 2

| No. of Example | | First layer | Second layer | Third layer | Fourth layer | Voltage 360 cd/m² |
|---|---|---|---|---|---|---|
| Invention devices | 7-1 | DNTPD | NPD | H-1(85), 1(15) | BAlq | 100 |
|  | 7-2 | CuPc | NPD | H-1(85), 1(15) | BAlq | 108 |
|  | 7-3 | DNTPD | HT-1 | H-1(85), 1(15) | BAlq | 109 |
|  | 7-4 | DNTPD | HT-2 | H-1(85), 1(15) | BAlq | 104 |
|  | 7-5 | DNTPD | HT-3 | H-1(85), 1(15) | BAlq | 98 |
|  | 7-6 | DNTPD | NPD | H-1(70), 1(15), VI-5(15) | BAlq | 79 |
|  | 7-7 | DNTPD | NPD | H-1(70), 1(15), VI-14(15) | BAlq | 78 |
|  | 7-8 | DNTPD | NPD | H-1(85), 1(15) | ET-1 | 106 |
|  | 7-9 | DNTPD | HT-4 | H-1(85), 1(15) | BAlq | 85 |
| Comparative devices | 7-1 | DNTPD | NPD | H-1(85), ref-2(15) | BAlq | 148 |
|  | 7-2 | CuPc | NPD | H-1(85), ref-2(15) | BAlq | 155 |
|  | 7-3 | DNTPD | HT-1 | H-1(85), ref-2(15) | BAlq | 178 |
|  | 7-4 | DNTPD | HT-2 | H-1(85), ref-2(15) | BAlq | 180 |
|  | 7-5 | DNTPD | HT-3 | H-1(85), ref-2(15) | BAlq | 145 |
|  | 7-6 | DNTPD | NPD | H-1(70), ref-2(15), VI-5(15) | BAlq | 98 |
|  | 7-7 | DNTPD | NPD | H-1(70), ref-2(15), VI-14(15) | BAlq | 97 |
|  | 7-8 | DNTPD | NPD | H-1(85), ref-2(15) | ET-1 | 160 |
|  | 7-9 | DNTPD | HT-4 | H-1(85), ref-2(15) | BAlq | 121 |

It can be found from the results of Table 2 that even when the materials of the layers other than the third layer were changed, the luminescence devices can provide the drive voltage reducing effect with broad generality.

(Fabrication of Invention Devices 8-1 and 8-2, and Comparative Devices 8-1 and 8-2)

These devices were each fabricated in a similar manner to that employed in Comparative device 1-1 except that the materials constituting the third layer were changed to Material 1 and Material 2 listed in the following Table 3. In Table 3, a ratio of Material 1 to Material 2 is 85:15 (mass ratio). The drive voltage is indicated as a relative value to that of Invention device 1-1 set to 100.

TABLE 3

| No. of Examples | | Material 1 | Material 2 | Maximum emission wavelength (nm) | CIE chromaticity x | CIE chromaticity y | Voltage 360 cd/m² |
|---|---|---|---|---|---|---|---|
| Invention devices | 1-1 | H-1 | 1 | 467 | 0.21 | 0.39 | 100 |
|  | 1-5 | H-1 | 6 | 513 | 0.27 | 0.56 | 94 |
| Comparative devices | 1-2 | H-1 | ref-2 | 482 | 0.28 | 0.37 | 148 |
|  | 1-3 | H-1 | ref-3 | 467 | 0.20 | 0.31 | 152 |
| Invention devices | 8-1 | H-6 | 1 | 467 | 0.17 | 0.24 | 98 |
|  | 8-2 | H-6 | 6 | 512 | 0.22 | 0.32 | 92 |
| Comparative devices | 8-1 | H-6 | ref-2 | 482 | 0.28 | 0.39 | 140 |
|  | 8-2 | H-6 | ref-3 | 467 | 0.19 | 0.32 | 151 |

It can be found from the results of Table 3 that when the material H-6 is used for the light emitting layer, the resulting device has a reduced chromaticity and improved blue color purity without impairing the voltage reduction effect.

(Fabrication of Invention Devices 9-1 to 9-9)

These devices were each fabricated in a similar manner to that employed for Comparative device 1-1 except that the materials constituting the third layer were changed to Materials 1 to 3 shown in the following Table 4. In Table 4, a ratio of Material 1 to Material 2 is 85:15 (mass ratio). The external quantum efficiency is indicated as a relative value to that of Invention device 9-1 (same as Invention device 2-4) set to 100. The drive voltage is indicated as a relative value to that of Invention device 9-2 set to 100.

TABLE 4

| No. of examples | Material 1 | Material 2 | Material 3 | Voltage 360 cd/m² | External quantum efficiency (relative value) |
|---|---|---|---|---|---|
| Invention device 9-1 | H-2(85) | 8(15) | — | 102 | 100 |
| Invention device 9-2 | H-2(80) | 8(15) | FIrpic(5) | 100 | 119 |
| Invention device 9-3 | H-2(80) | 8(15) | D-1(5) | 101 | 145 |
| Invention device 9-4 | H-2(80) | 8(15) | D-2(5) | 100 | 150 |
| Invention device 9-5 | H-2(80) | 8(15) | D-3(5) | 102 | 151 |
| Invention device 9-6 | H-2(80) | 8(15) | D-4(5) | 100 | 146 |
| Invention device 9-7 | H-2(80) | 8(15) | D-5(5) | 99 | 167 |
| Invention device 9-8 | H-2(85) | 20(15) | — | 89 | 78 |
| Invention device 9-9 | H-2(80) | 20(15) | D-6(5) | 90 | 121 |

It can be found from the results of Table 4 that the device has improved luminous efficiency by incorporating, in combination with the compound of the invention, a phosphorescent material having a greater lowest triplet energy in the light emitting layer. The results also suggest that the device has a high luminous efficiency by incorporating a phosphorescent material represented by the formula (C-1) in combination.

(Fabrication of Comparative Device 10-1)

A glass substrate (product of Geomatec having a surface resistivity of 10 Ω/□) 0.5 mm thick and 2.5 cm square and having an ITO film thereon was put in a cleaning container, ultrasonically cleaned in 2-propanol, and subjected to UV ozone treatment for 30 minutes. A hole transport layer 50 nm thick was formed by applying, onto the resulting substrate, a solution obtained by diluting poly(3,4-ethylenedioxythiophene)-polystyrene sulfonate (PEDOT/PSS) into 70% with pure water by using a spin coater. Then, a light emitting layer 30 nm thick was formed by applying, onto the hole transport layer, a methylene chloride solution in which H-1 and ref-1 had been dissolved at a H-1:ref-1 mass ratio of 85:15 by using a spin coater. On the resulting light emitting layer, BAlq [bis(2-methyl-8-quinolinolate)-4-(phenylphenolate)aluminum] was deposited to a thickness of 40 nm. On the resulting organic compound layer, lithium fluoride and aluminum were deposited to thicknesses of 0.5 nm and 150 nm as a cathode buffer layer and a cathode, respectively in a deposition apparatus. Without bringing the resulting product into contact with the atmosphere, it was put in a glove box purged with an argon gas and sealed with a IW-curing adhesive ("XNR5516HV", product of Nagase Ciba) in a stainless-steel sealing can to obtain an organic EL device of Comparative example 10-1.

(Fabrication of Invention Devices 10-1 to 10-16 and Comparative Devices 10-2 to 10-12)

The above-described devices were fabricated in a similar manner to that employed for Comparative device 10-1 except the materials constituting the third layer were changed to Material 1 and Material 2 as listed in the following Table 5. In Table 5, a ratio of Material 1 to Material 2 is 85:15 (mass ratio).

The devices thus obtained were each tested for maximum emission wavelength and drive voltage.

The results are shown in Table 5. In this table, the drive voltage is expressed as a relative value to the drive voltage of Invention device 10-1 set to 100.

TABLE 5

| No. of Example | Material 1 | Material 2 | Maximum emission wavelength (nm) | Voltage (V) 360 cd/m², relative value |
|---|---|---|---|---|
| Invention device 10-1 | H-1 | 1 | 467 | 100 |
| Invention device 10-2 | H-1 | 2 | 462 | 100 |
| Invention device 10-3 | H-1 | 6 | 513 | 97 |
| Invention device 10-4 | H-1 | 8 | 465 | 100 |
| Invention device 10-5 | H-1 | 10 | 446 | 101 |
| Invention device 10-6 | H-1 | 13 | 458 | 94 |
| Invention device 10-7 | H-1 | 16 | 465 | 99 |
| Invention device 10-8 | H-1 | 17 | 465 | 95 |
| Invention device 10-9 | H-2 | 4 | 461 | 100 |
| Invention device 10-10 | H-2 | 5 | 460 | 100 |
| Invention device 10-11 | H-3 | 9 | 451 | 67 |
| Invention device 10-12 | H-5 | 7 | 477 | 100 |
| Invention device 10-13 | H-5 | 20 | 478 | 91 |
| Invention device 10-14 | H-5 | 22 | 472 | 99 |
| Invention device 10-15 | H-7 | 1 | 467 | 100 |
| Invention device 10-16 | H-7 | 10 | 449 | 104 |
| Invention device 10-17 | H-1 | 19 | 473 | 100 |
| Comparative device 10-1 | H-1 | ref-1 | 476 | 154 |
| Comparative device 10-2 | H-1 | ref-2 | 482 | 124 |
| Comparative device 10-3 | H-1 | ref-5 | 600 | 141 |
| Comparative device 10-4 | H-1 | ref-6 | 469 | 135 |
| Comparative device 10-5 | H-1 | ref-7 | 457 | 138 |
| Comparative device 10-6 | H-1 | Ir(ppy)$_3$ | 514 | 146 |
| Comparative device 10-7 | H-2 | ref-2 | 482 | 128 |
| Comparative device 10-8 | H-3 | ref-1 | 478 | 134 |
| Comparative device 10-9 | H-5 | ref-4 | 482 | 125 |
| Comparative device 10-10 | H-5 | Ir(ppy)$_3$ | 515 | 140 |
| Comparative device 10-11 | H-7 | ref-1 | 477 | 139 |
| Comparative device 10-12 | H-7 | ref-7 | 458 | 137 |

The results of Table 5 have revealed that even when the device is fabricated by using the compound of the invention in accordance with the method of application, it exhibits a drive voltage reduction effect.

The following are structures of the compound used in the above Examples.

Exemplified compounds

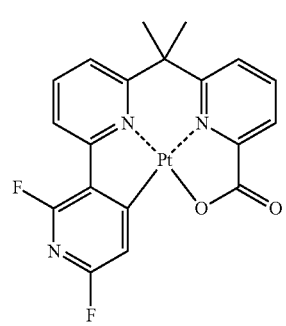

1

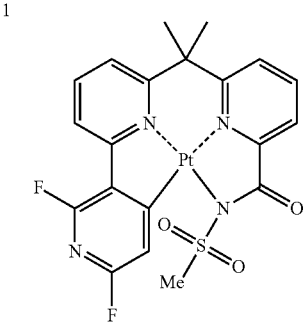

2

-continued
| | |
|---|---|
| 3 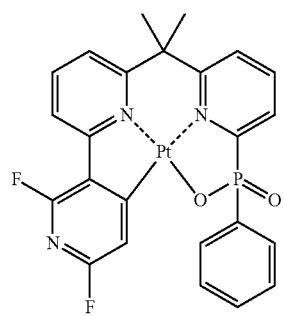 | 4 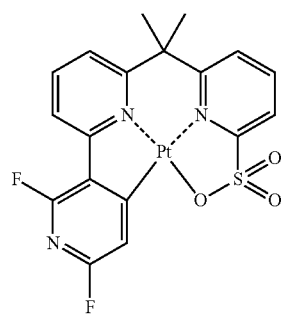 |
| 5 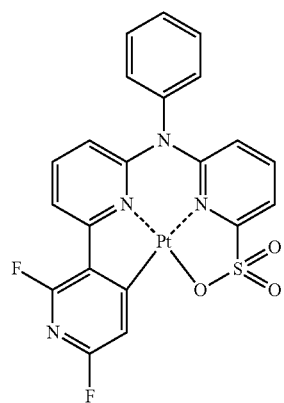 | 6 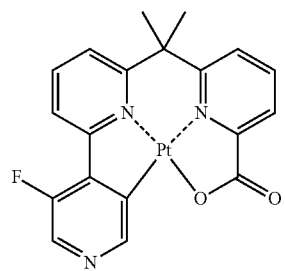 |
| 7 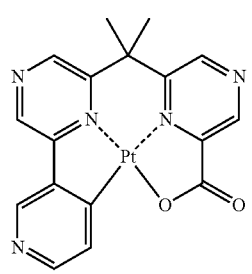 | 8 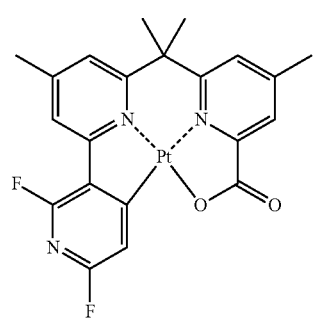 |
| 9 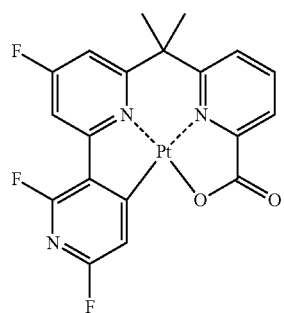 | 10 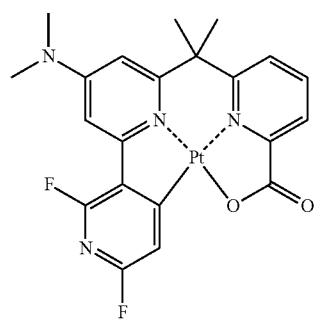 |

-continued
11
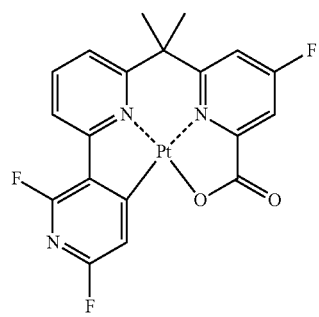
12
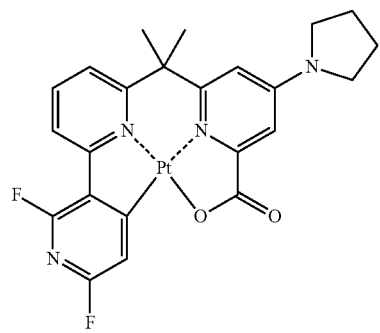
13
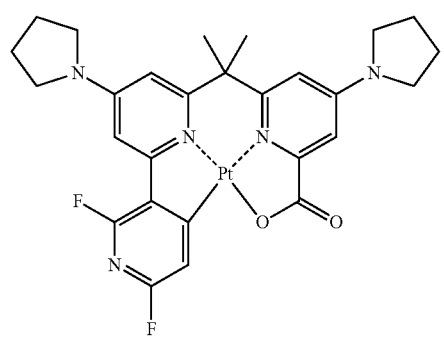
14
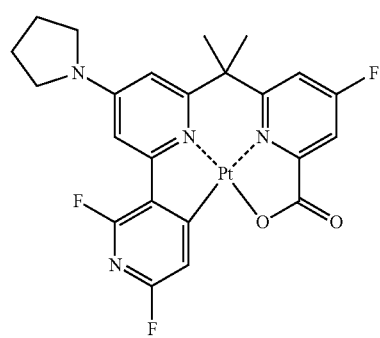
15
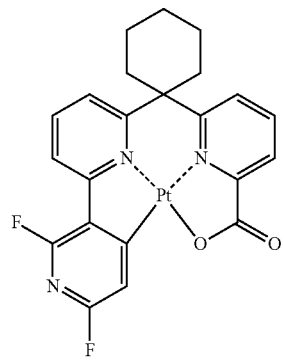
16
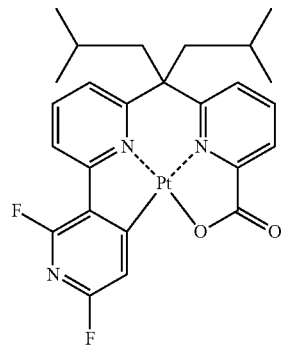
17
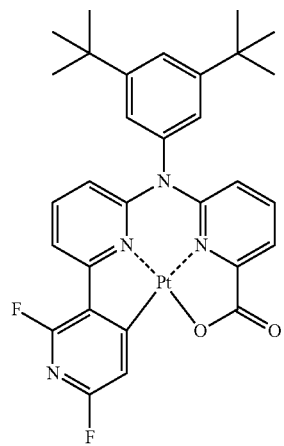
18
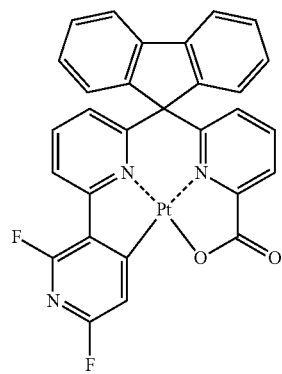

-continued
19
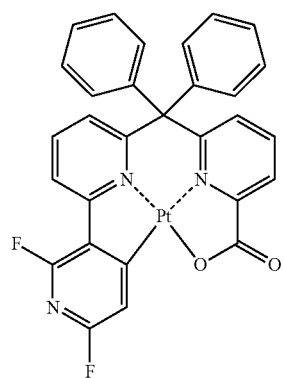
20
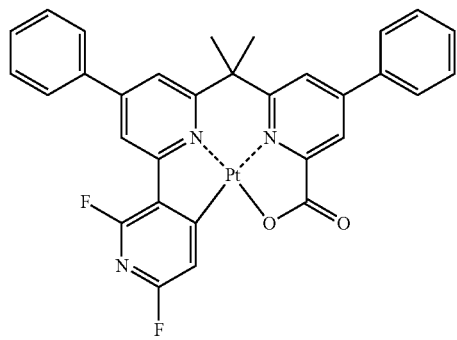
21
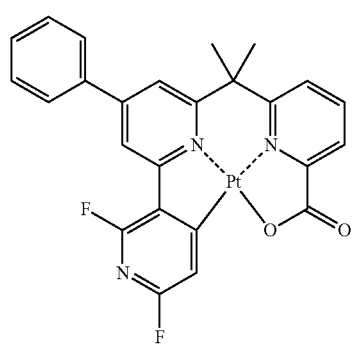
22
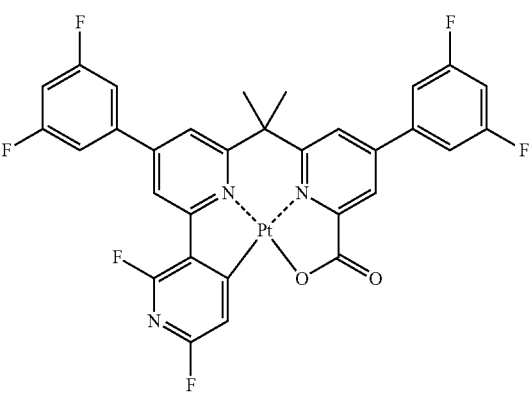
Comparative compounds
ref-1
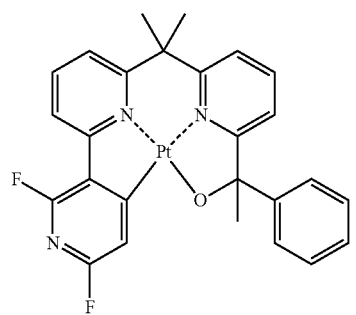
ref-2
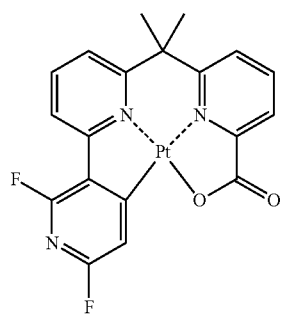
ref-3
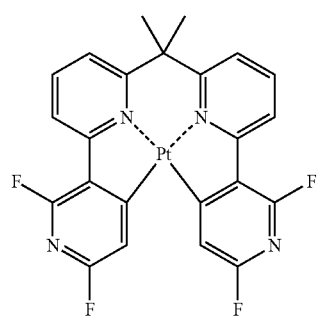
ref-4
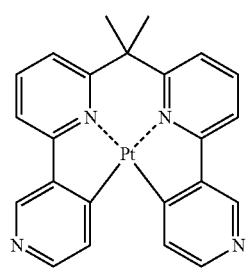

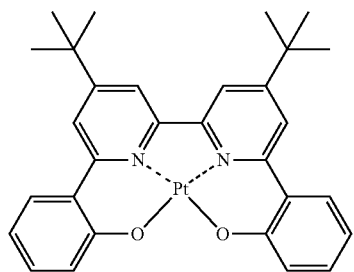
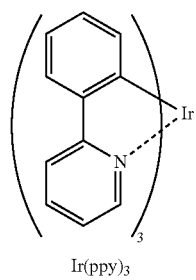
ref-5
Ir(ppy)₃
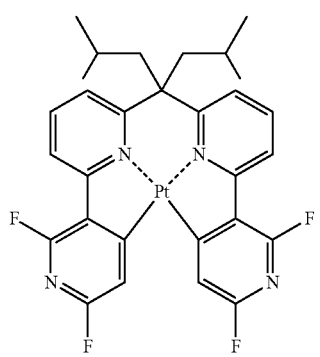
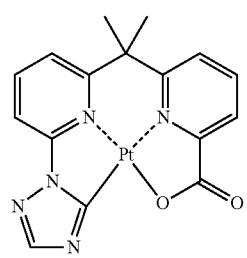
ref-6                ref-7
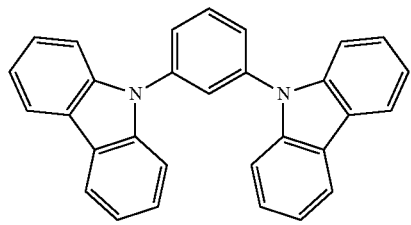
H-1
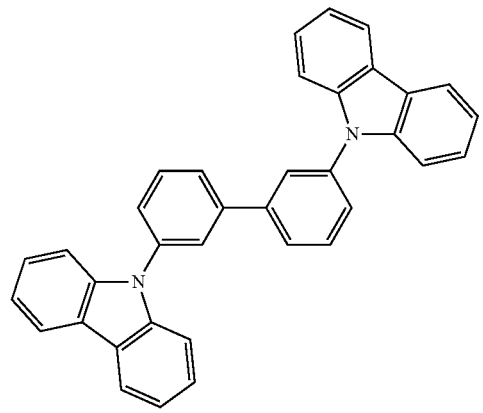
H-2
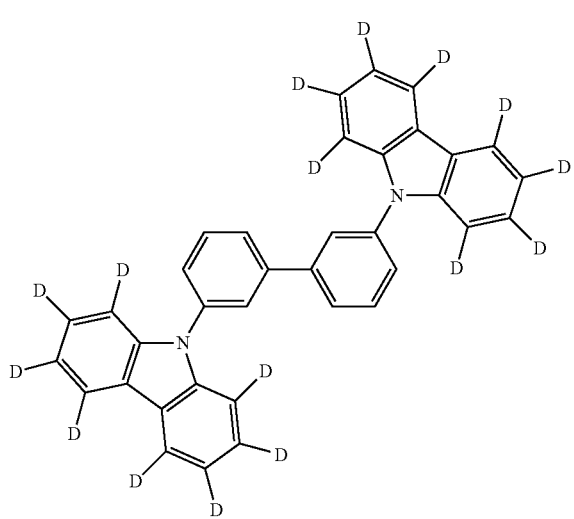
H-3
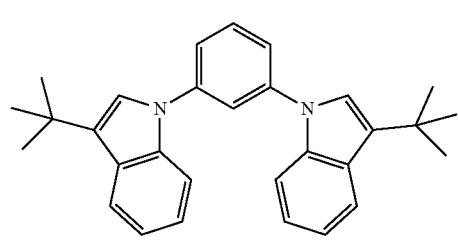
H-4

-continued
H-5
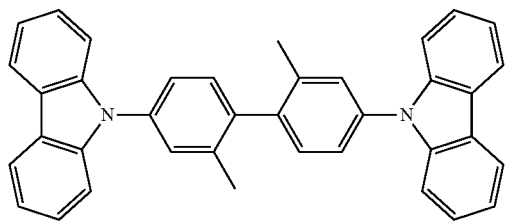
H-6
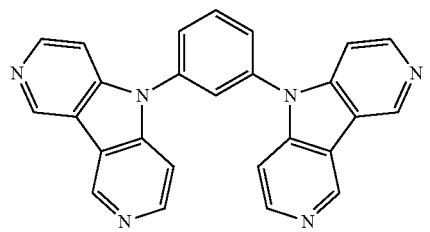
H-7
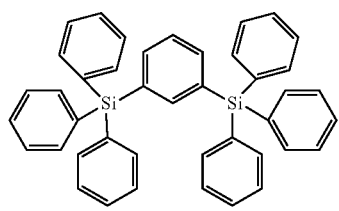
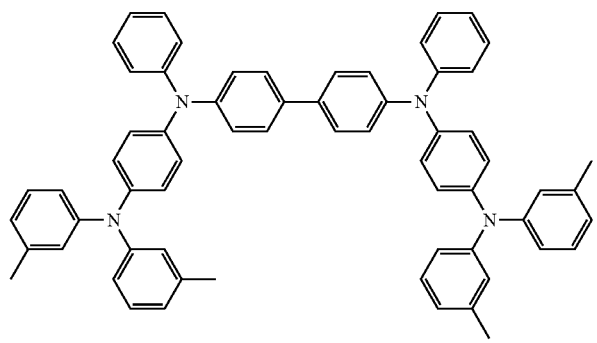
DNTPD
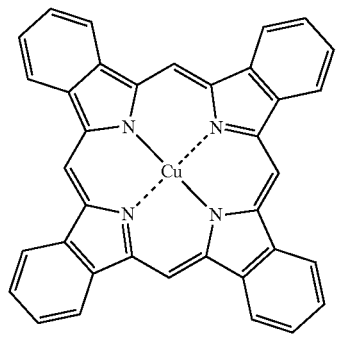
CuPc
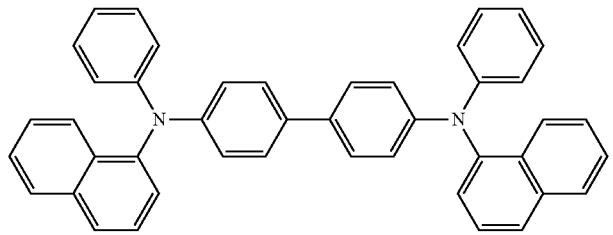
NPD
HT-1
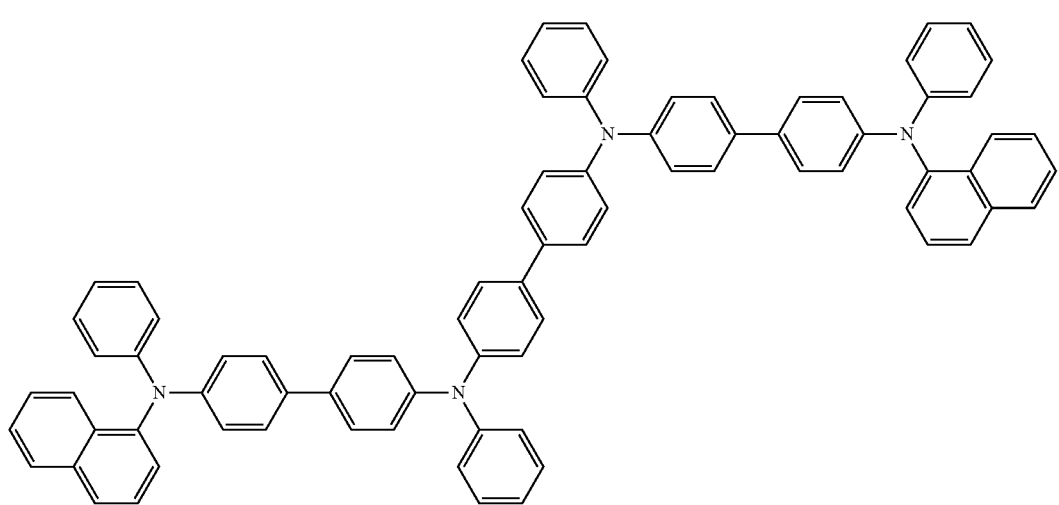

-continued
HT-2
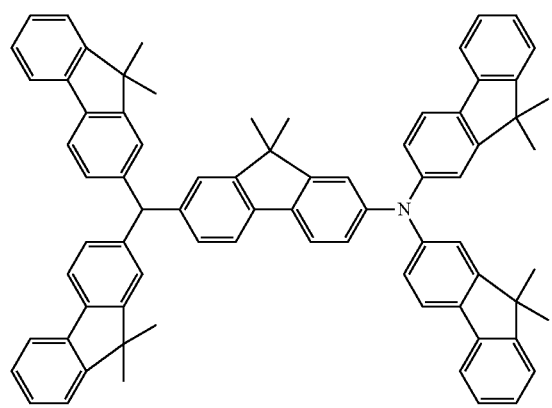
HT-3
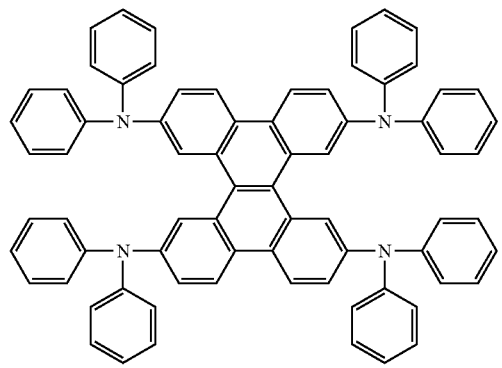
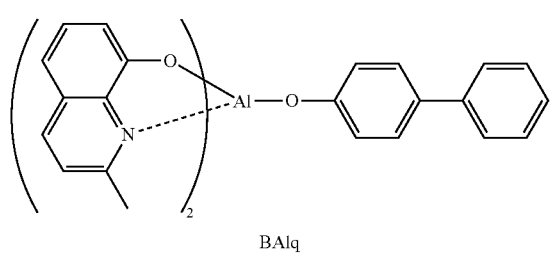
BAlq
ET-1
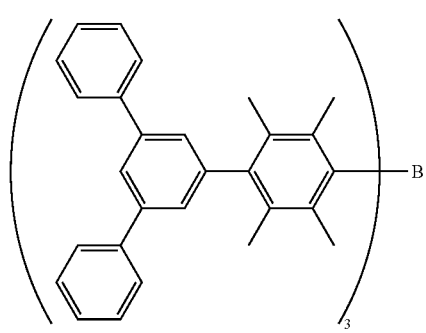
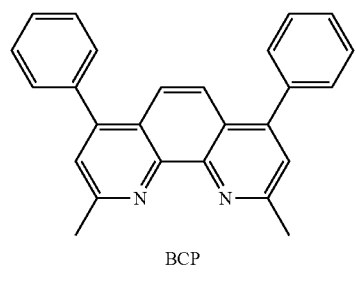
BCP
VI-5
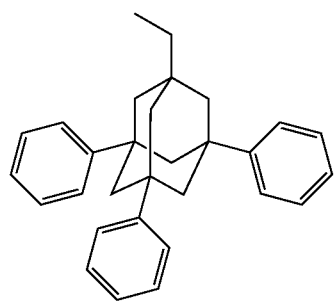
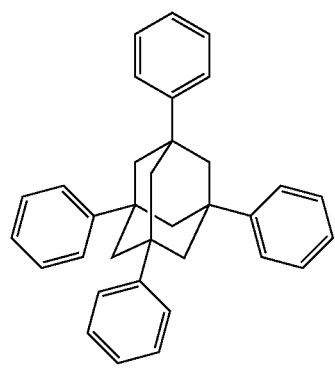
VI-14
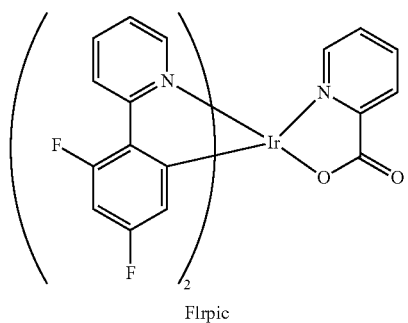
FIrpic -continued
HT-4
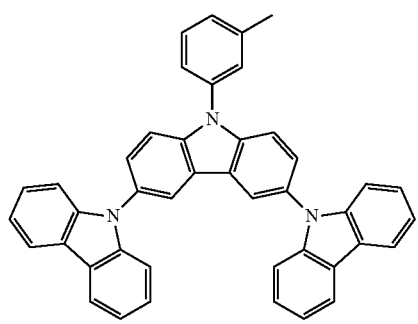
H-8
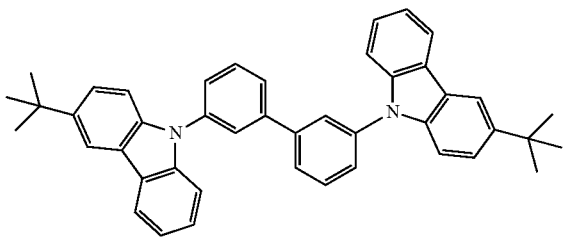
H-9
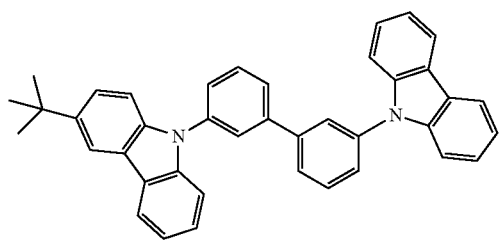
H-10
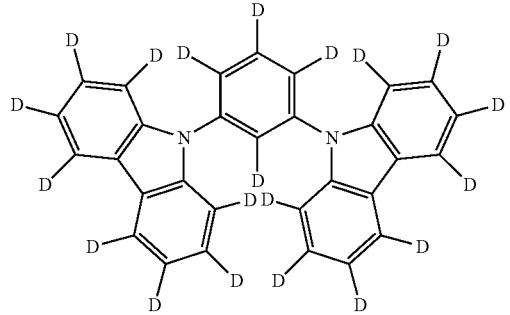
H-11
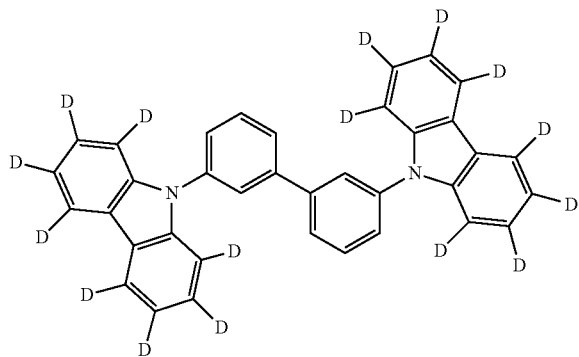
D-1
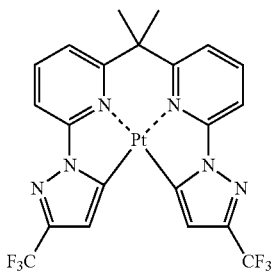
D-2
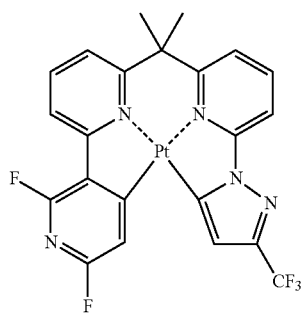
D-3
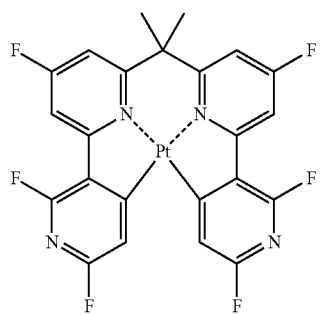

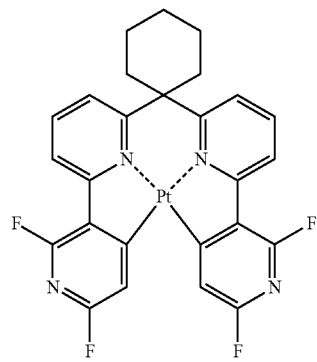

D-4

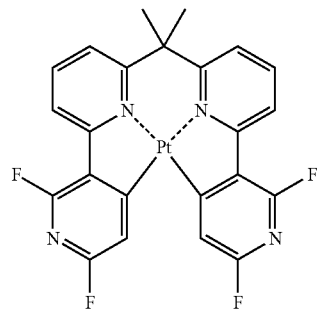

D-5

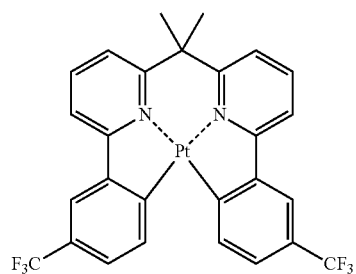

D-6

What is claimed is:

1. An organic electroluminescent device comprising:
a pair of electrodes; and
a light emitting layer between the electrodes,
wherein the organic electroluminescent device has a layer containing a compound represented by formula (III):

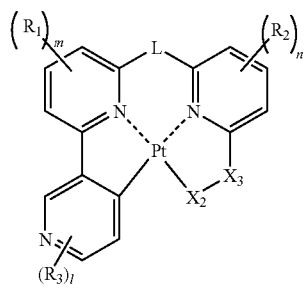

(III)

wherein L represents a divalent linking group, $R_1$, $R_2$ and $R_3$ each independently represents a substituent, and m, n, l each independently represents an integer from 0 to 3, wherein a partial structure of $X_2$ and $X_3$ is either represented by any of the following (ii), (iv) or (v):

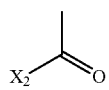

(i)

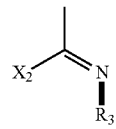

(ii)

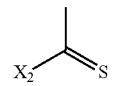

(iii)

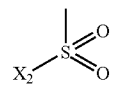

(iv)

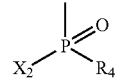

(v)

wherein in (ii) and (v) $X_2$ represents a sulfur atom, a phosphorus atom, an oxygen atom, or a nitrogen atom and in (iv) $X_2$ represents a sulfur atom, a phosphorus atom, or a nitrogen atom, wherein $R_3$ represents a substituent and $R_4$ represents a substituent, and $X_2$ and $R_3$ in (ii) do not form a cyclic structure;

or the partial structure of $X_2$ and $X_3$ is represented by (i) or (iii), wherein in (i) $X_2$ is a phosphorus atom and in (iii) $X_2$ is selected from the group consisting of a phosphorus atom and a nitrogen atom.

2. The organic electroluminescent device according to claim 1, wherein the compound represented by formula (III) is a compound represented by formula (IV):

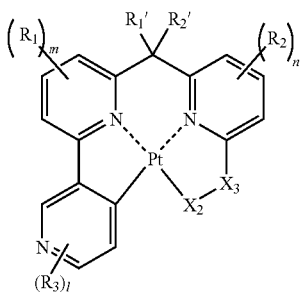

(IV)

wherein $X_2$ and $X_3$ have the same meanings as in formula (III), $R_1$, $R_2$, and $R_3$ each independently represents a substituent, m, n, and l each independently represents an integer from 0 to 3, and $R_1'$ and $R_2'$ each independently represents a hydrogen atom or a substituent.

3. The organic electroluminescent device according to claim 1, wherein the layer containing the compound represented by formula (III) is the light emitting layer.

4. The organic electroluminescent device according to claim 1, wherein the light emitting layer contains a host material.

5. The organic electroluminescent device according to claim 4, wherein the host material is a compound represented by formula (V):

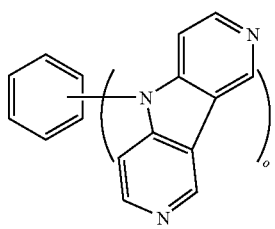

(V)

wherein o stands for an integer from 1 to 3.

6. The organic electroluminescent device according to claim 1, wherein the light emitting layer contains a compound represented by formula (VI):

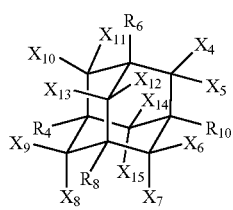

(VI)

wherein $R_4$, $R_6$, $R_8$, $R_{10}$, and $X_4$ to $X_{15}$ each independently represents a hydrogen atom, an alkyl group, or an aryl group.

7. The organic electroluminescent device according to claim 1, wherein the L represents an alkylene group, an arylene group, a heteroarylene group, an imino group, an oxy group, a thio group, a phosphinidene group, or a silylene group.

8. The organic electroluminescent device according to claim 1, wherein L represents an arylimino group or —$CR_1'R_2'$—, wherein $R_1'$ and $R_2'$ each represents an alkyl group, an alkyl halide group, or an aryl group.

9. The organic electroluminescent device according to claim 1, wherein L represents a phenylimino group, a 3,5-di-tert-butylphenylimino group, or —$CR_1'R_2'$—, wherein $R_1'$ and $R_2'$ each represents an alkyl group, an alkyl halide group, or an aryl group.

10. The organic electroluminescent device according to claim 1, wherein $R_1$ and the $R_2$ each independently represents a halogen atom, an alkylamino group, an aryl group, or an alkyl group.

11. The organic electroluminescence device according to claim 1, wherein $R_3$ of $(R_3)_l$ represents a halogen atom.

12. A compound represented by formula (III):

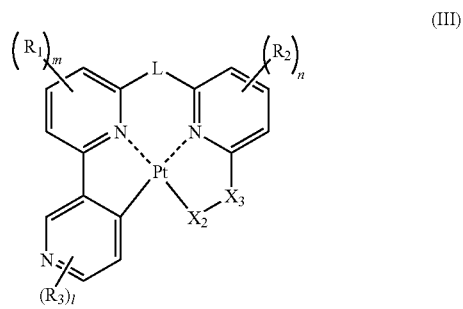

(III)

wherein L represents a divalent linking group, $R_1$, $R_2$ and $R_3$ each independently represents a substituent, and m, n, l each independently represents an integer from 0 to 3, wherein a partial structure of $X_2$ and $X_3$ is either represented by any of the following (ii), (iv) or (v):

(i)

(ii)

(iii)

(iv)

(v)

wherein in (ii) and (v) $X_2$ represents a sulfur atom, a phosphorus atom, an oxygen atom, or a nitrogen atom and in (iv) $X_2$ represents a sulfur atom, a phosphorus atom, or a nitrogen atom, $R_3$ represents a substituent and $R_4$ represents a substituent, and $X_2$ and $R_3$ in (ii) do not form a cyclic structure;

or the partial structure of $X_2$ and $X_3$ is represented by (i) or (iii), wherein in (i) $X_2$ is a phosphorus atom and in (iii) $X_2$ is selected from the group consisting of a phosphorus atom and a nitrogen atom.

13. The compound according to claim 12, wherein the compound represented by formula (III) is represented by formula (IV):

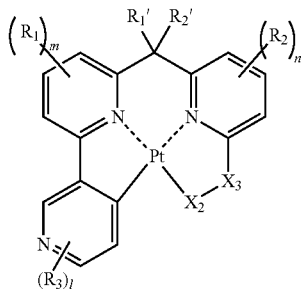

wherein a partial structure of $X_2$ and $X_3$ is either represented by any of (ii), (iv) or (v), wherein in (ii) and (v) $X_2$ represents a sulfur atom, a phosphorus atom, an oxygen atom, or a nitrogen atom and in (iv) $X_2$ represents a sulfur atom, or a phosphorus atom, or a nitrogen atom; or the partial structure of $X_2$ and $X_3$ is represented by (i) or (iii), wherein in (i) $X_2$ is a phosphorus atom and in (iii) $X_2$ is selected from the group consisting of a phosphorus atom and a nitrogen atom, $R_1$, $R_2$, and $R_3$ each independently represents a substituent, m, n, and l each independently stands for an integer from 0 to 3, and $R_1'$ and $R_2'$ each independently represents a hydrogen atom or a substituent.

14. The compound according to claim 12, wherein L represents an alkylene group, an arylene group, a heteroarylene group, an imino group, an oxy group, a thio group, a phosphinidene group, or a silylene group.

15. The compound according to claim 12, wherein L represents an arylimino group or —$CR_1'R_2'$—, wherein $R_1'$ and $R_2'$ each represents an alkyl group, an alkyl halide group, or an aryl group.

16. The compound according to claim 12, wherein L represents a phenylimino group, a 3,5-di-tert-butylphenylimino group, or —$CR_1'R_2'$—, wherein $R_1'$ and $R_2'$ each represents an alkyl group, an alkyl halide group, or an aryl group.

17. The compound according to claim 12, wherein $R_1$ and $R_2$ each independently represents a halogen atom, an alkylamino group, an aryl group, or an alkyl group.

18. The compound according to claim 12, wherein $R_3$ of $(R_3)_l$ represents a halogen atom.

19. A light emitting material comprising a compound according to claim 12.

20. A light emitting layer comprising a compound according to claim 12 as a light emitting material.

21. A light emitting apparatus comprising an organic electroluminescent device according to claim 1.

22. An illumination apparatus comprising an organic electroluminescent device according to claim 1.

23. The organic electroluminescent device according to claim 1, wherein at least one layer between the pair of electrodes is manufactured by a coating method.

* * * * *